US010167292B2

(12) United States Patent
Burns et al.

(10) Patent No.: US 10,167,292 B2
(45) Date of Patent: Jan. 1, 2019

(54) BENZODIAZEPINES AS BROMODOMAIN INHIBITORS

(71) Applicant: Catalyst Therapeutics Pty Ltd, Victoria (AU)

(72) Inventors: Chris Burns, Victoria (AU); Jean-Marc Garnier, Victoria (AU); Phillip Patrick Sharp, Victoria (AU); John Feutrill, Victoria (AU); Anthony Cuzzupe, Victoria (AU)

(73) Assignee: Catalyst Therapeutics Pty Ltd., Victoria (AU)

( * ) Notice: Subject to any disclaimer, the term of this patent is extended or adjusted under 35 U.S.C. 154(b) by 0 days.

(21) Appl. No.: 15/749,950

(22) PCT Filed: Aug. 4, 2016

(86) PCT No.: PCT/AU2016/050703
§ 371 (c)(1),
(2) Date: Feb. 2, 2018

(87) PCT Pub. No.: WO2017/020086
PCT Pub. Date: Feb. 9, 2017

(65) Prior Publication Data
US 2018/0230153 A1 Aug. 16, 2018

(30) Foreign Application Priority Data
Aug. 4, 2015 (AU) .................................. 2015903111

(51) Int. Cl.
*C07D 487/04* (2006.01)
(52) U.S. Cl.
CPC .................................. *C07D 487/04* (2013.01)
(58) Field of Classification Search
CPC .................................................. C07D 487/04
See application file for complete search history.

(56) References Cited

FOREIGN PATENT DOCUMENTS

WO WO 2012/068149 5/2012
WO WO 2012/151512 11/2012

OTHER PUBLICATIONS

Akritopoulou-Zanze, et al., A versatile synthesis of fused triazolo derivatives by sequential Ugi/alkyne-azide cycloaddition reactions, Tetrahedron Letters, 45, 8439-8441 (2004). (Year: 2004).*
Margueron, et al. "The key to development: interpreting the histone code?" Current Opinion in Genetics & Development 2005, vol. 15, pp. 163-176.
Luger, et al. "Crystal structure of the nucleosome core particle at 2.8 A resolution" Nature, Sep. 1997, vol. 389, pp. 251-260.

Dey, et al. "Brd4 Marks Select Genes on Mitotic Chromatin and Directs Postmitotic Transcription" Molecular Biology of the Cell, Dec. 1, 2009, vol. 20, pp. 4899-4909.
Filippakopoulos, et al. "Selective inhibition of BET bromodomains" Nature, Dec. 2010, vol. 468, pp. 1067-1073.
Nicodeme, et al. "Suppression of inflammation by a synthetic histone mimic," Nature, Dec. 2010, vol. 468, pp. 1119-1123.
Yang, et al. "Multisite protein modification and intramolecular signaling" Oncogene (2005), vol. 24, pp. 1653-1662.
Yang, et al. "Recruitment of P-TEFb for Stimulation of Transcriptional Elongation by the Bromodomain Protein Brd4" Molecular Cell, Aug. 19, 2005, vol. 19, pp. 535-545.
Phelps, et al. "Clinical response and pharmacokinetics from a phase 1 study of an active dosing schedule of flavopiridol in relapsed chronic lymphocytic leukemia" Blood, Mar. 19, 2009, vol. 113, No. 12, pp. 2637-2645.
Rahl, et al. "c-Myc Regulates Transcriptional Pause Release" Cell, Apr. 30, 2010, vol. 141, pp. 432-445.
French, et al. "BRD4 Bromodomain Gene Rearrangement in Aggressive Carcinoma with Translocation (15;19)" American Journal of Pathology, No. 6, Dec. 2001, vol. 159, pp. 1987-1992.
French, et al. "BRD4-NUT Fusion Oncogene: A Novel Mechanism in Aggressive Carcinoma" Cancer Research, Jan. 15, 2003, vol. 63, pp. 304-307.
Hargreaves, et al. "Control of Inducible Gene Expression by Signal-Dependent Transcriptional Elongation" Cell, Jul. 10, 2009, vol. 138, pp. 129-145.
Leroy, et al. "The Double Bromodomain Proteins Brd2 and Brd3 Couple Histone Acetylation to Transcription" Molecular Cell, Apr. 11, 2008, vol. 30, pp. 51-60.
Jang, et al. "The Bromodomain Protein Brd4 Is a Positive Regulatory Component of P-TEFb and Stimulates RNA Polymerase II-Dependent Transcription" Molecular Cell, Aug. 19, 2005, vol. 19, pp. 523-534.
Banerjee et al. "BET bromodomain inhibition as a novel strategy for reactivation of HIV-1" Journal of Leukocyte Biology, Dec. 2012, vol. 92, pp. 1147-1154.
Boehm et al. "BET bromodomain-targeting compounds reactivate HIV from latency via a Tat-independent mechanism" Cell Cycle, Feb. 1, 2013, vol. 12:3, pp. 452-462.

(Continued)

*Primary Examiner* — Erich A Leeser
(74) *Attorney, Agent, or Firm* — Cooley LLP; Ivor R. Elrifi; Matthew Pavao

(57) ABSTRACT

The present invention provides novel benzodiazepine derivatives of Formula I or pharmaceutically acceptable derivatives, polymorphs, salts or prodrugs thereof. Said compounds have potential as bromodomain (BRD) inhibitors.

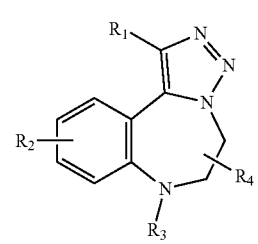

I

20 Claims, No Drawings

(56) References Cited

OTHER PUBLICATIONS

Miyaura et al. "Palladium-Catalyzed Cross-Coupling Reactions of Organoboron Compounds" Chem Rev. 1995, 95, 2457-2483.
Mitchell, "Palladium-Catalysed Reactions of Organotin Compounds" Synthesis, Sep. 1992, pp. 803-815.
Kumada et al. Organic Synthesis, Coll. vol. 6, p. 407 (1988); vol. 58, p. 127 (1978).
Negishi, Ei-ichi "A genealogy of Pd-catalyzed cross-coupling" Journal of Organometallic Chemistry, 2002, vol. 653, pp. 34-40.
Whitcombe et al. "Advances in the Heck chemistry of aryl bromides and chlorides" Tetrahedron, 2001, vol. 57, pp. 7449-7476.
Pal, Manojit "Palladium-Catalyzed Alkynylation of Aryl and Hetaryl Halides: A Journey from Conventional Palladium Complexes or Salts to Palladium/Carbon" SYNLETT 2009, No. 18, pp. 2896-2912.
Xiao et al. "A Direct and General Method for the Reductive Alkylation of Tertiary Lactams/Amides: Application to the Step Economical Synthesis of Alkaloid (−)-Morusimic Acid D" The Journal of Organic Chemistry 2013, 78, pp. 8305-8311.
Troust, B.M. et al. Comprehensive Organic Synthesis, 1991, 3, 551-561. (abstract).
Gilbert et al. "Diazoethenes: Their Attempted Synthesis from Aldehydes and Aromatic Ketones by Way of the Horner-Emmons Modification of the Wittig Reaction. A Facile Synthesis of Alkynes" J. Org. Chem., 1982, 47, pp. 1837-1845.
An et al. "Convenient Synthesis of (1-Propynyl)arenes through a One-Pot Double Elimination Reaction, and Their Conversion to Enynes" SYNLETT 2007, No. 12, pp. 1909-1912.
Hartwig, John F. "Transition Metal Catalyzed Synthesis of Arylamines and Aryl Ethers from Aryl Halides and Triflates: Scope and Mechanism" Angew. Chem. Int. Ed. 1998, 37, pp. 2046-2067.
Song et el. "Cascade Electrophilic Iodocyclization: Efficient Preparation of 4-Iodomethyl Substituted Tetrahydro-β-carbolines and Formal Synthesis of Oxopropaline G" Organic Letters, 2013, vol. 15, No. 13, pp. 3274-3277.
Majumder et al. "Catalyst-Free 1,3-Dipolar Cycloaddition: An Efficient Route for the Formation of the 1,2,3-Triazile-Fused Diazepinone Framework", Synthesis, 2010, 5, 858-62.
Akritopoulou-Zanze, et al, "A versatile synthesis of fused triazolo derivatives by sequential Ugi/alkyne-azide cycloaddition reactions", Tetrahedron Letters 45, 2004, pp. 8439-8441.
International Search Report and Written Opinion, dated Sep. 5, 2016, for International Application No. PCT/AU2016/050703.
Molteni, G., "Three-Step Synthesis of Triazolobenzodiazepinones via Sonogashira/Huisgen Protocol" Heterocycles, 2013, 87(8), 1765-1773.

* cited by examiner

BENZODIAZEPINES AS BROMODOMAIN INHIBITORS

CROSS-REFERENCE TO RELATED APPLICATIONS

This application is a national stage application, filed under 35 U.S.C. 371, of International Application No. PCT/AU2016/050703, filed on Aug. 4, 2016, which claims priority to, and the benefit of, Australian Patent Application No. 2015903111, filed Aug. 4, 2015. The contents of each of these applications are incorporated by reference in their entirety.

FIELD OF THE INVENTION

The present invention provides novel benzodiazepine derivatives. Said compounds have potential as bromodomain (BRD) inhibitors.

BACKGROUND OF THE INVENTION

A bromodomain (BRD), present in some proteins, is a conserved structural motif that binds to N-acetylated lysine residues of various proteins. BRDs occur as functionally distinct modules in a variety of proteins including chromatin-associated proteins, histone acetyltransferases and transcriptional activators. Inhibitors of the interaction between a bromodomain and its cognate N-acetylated protein binding partner are believed to be useful in the treatment of a variety of diseases or conditions, such as cancer as well as chronic autoimmune and inflammatory conditions.

The Bromodomain and Extra-C Terminal domain (BET) protein family is comprised of four members (BRD2, BRD3, BRD4 and BRDT). BRD2, BRD3 and BRD4 are expressed ubiquitously whereas BRDT expression is largely limited to the testis. Each member of the BET family possesses two bromodomain motifs that bind N-acetylated lysine residues on the amino-terminal tails of histone proteins. Once bound these proteins modulate gene expression by affecting chromatin status and recruiting transcription factors to specific genome locations within chromatin. For example, BRD4 and BRDT independently recruit CDK9 and cyclin T1, which together constitute the catalytic subunit of the positive transcription elongation factor b (P-TEFb). This results in phosphorylation of the carboxy-terminal domain (CTD) heptad repeat of RNA Polymerase II, thereby facilitating transcription elongation and the expression of a subset of genes involved in cell cycle progression. BRD2 and BRD3 have been shown to associate with several transcription co-activators and/or co-repressors, which regulate transcription control of various genes including cyclin A and cyclin D1. In addition BRD2 and BRD4 have been reported to possess atypical kinase activity and BRD4 has also been reported to bind to acetylated RelA, a sub-unit of NF-κB.

BET family members have recently been shown to be involved in the maintenance and progression of several cancer types including leukaemia, lymphoma, multiple myeloma and solid tumours such as non-small cell lung cancer, osteosarcoma and glioblastoma. The fusion between BRD4 (and to a lesser extent BRD3) with the nuclear protein in testis (NUT) gene leads to squamous cell carcinomas known as NUT midline carcinomas (NMC). BET family members have also been implicated in mediating acute inflammatory responses and in HIV-associated kidney disease. BRD2 function has also been linked to obesity and Type II diabetes. The human immunodeficiency virus utilizes BRD4 to initiate transcription of viral RNA from stably integrated viral DNA. BET bromodomain inhibitors have also been shown to reactivate HIV transcription in models of latent T cell infection and latent monocyte infection. BRDT has an important role in spermatogenesis and disruption of normal BRDT binding to acetylated histones may have utility as a male contraceptive.

Therefore, there is an ongoing medical need to develop new drugs to treat diseases and indications involving bromodomain function, including BET bromodomain function.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY OF THE INVENTION

In one aspect, there is provided a compound of Formula I or a pharmaceutically acceptable derivative, polymorph, salt or prodrug thereof

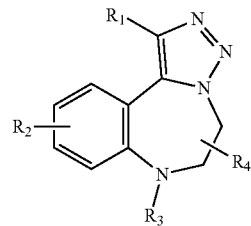

wherein:
$R_1$ is selected from the group consisting of H, $C_{1-4}$alkyl, $CF_3$, $CF_2H$, $C_{1-4}$alkylXH, $C_{1-4}$alkylOCOR$_5$; wherein X=O, S;

$R_2$ is 0-3 substituents independently selected from the group consisting of $C_{1-4}$alkyl, CN, Cl, Br, I, $C_{3-10}$heterocyclyl, $OC_{1-4}$alkyl, $C_{5-10}$heteroaryl, $C_{1-4}$alkylC$_{6-10}$aryl, $C_{1-4}$alkylC$_{5-10}$heteroaryl, hydroxyl, nitro, COR$_6$, CO$_2$R$_6$, CONR$_5$R$_6$, CONHSO$_2$R$_5$, SO$_2$NHCOR$_5$, CONR$_5$OR$_6$, $C_{1-4}$alkylNR$_5$R$_6$, $C_{1-4}$alkylOR$_6$, NR$_5$R$_6$, NR$_5$COR$_6$, NR$_7$CONR$_5$R$_6$ and NR$_5$CO$_2$R$_6$;

$R_3$ is selected from the group consisting of $C_{1-4}$alkyl, $C_{3-10}$cycloalkyl, $C_{3-10}$heterocyclyl, $C_{6-10}$aryl, $C_{1-4}$alkylC$_{6-10}$aryl;

$R_4$ is 1 to 2 groups on the same or adjacent carbons selected from oxo, $C_{1-4}$alkyl, $C_{1-4}$alkylOH, $C_{1-4}$alkylOCOR$_5$, $C_{1-4}$alkylCONR$_5$R$_6$, $C_{1-4}$alkylC$_{6-10}$aryl, $C_{1-4}$alkyl $C_{5-10}$heteroaryl;

$R_5$ and $R_6$ are independently selected from the group consisting of hydrogen, $C_{1-4}$alkyl, $C_{3-10}$cycloalkyl, $C_{3-10}$heterocyclyl, $C_{6-10}$aryl, $C_{5-10}$heteroaryl, $C_{1-4}$alkylC$_{6-10}$aryl and $C_{1-4}$alkylC$_{5-10}$heteroaryl;

alternatively $R_5$ and $R_6$ are bound to the same atom and form an optionally substituted ring that is 4 to 10 carbon atoms in size wherein optionally one or more carbon atoms are replaced with O, S, S(O), SO$_2$, or NR$_7$; and $R_7$ is selected from the group consisting of hydrogen and $C_{1-4}$alkyl and further wherein, unless otherwise stated, each alkyl, cycloalkyl, heterocycyl, heteroaryl, and aryl is optionally substituted.

In a further aspect, there is provided a composition comprising a compound of the present invention and a pharmaceutically acceptable excipient.

In another aspect, the invention provides a method for treating a bromodomain-containing protein-mediated disorder in a patient in need thereof, comprising the step of administering to said patient a compound or composition of the present invention.

In a yet further aspect, there is provided a compound or composition of the present invention for use in the treatment of a bromodomain-containing protein-mediated disorder in a patient in need thereof.

In yet another aspect, there is provided the use of a compound or composition of the present invention in the preparation of a medicament for the treatment of a bromodomain-containing protein-mediated disorder in a patient in need thereof.

DETAILED DESCRIPTION OF THE EMBODIMENTS

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) Curr. Opin. Genet. Dev. 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) Nature 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) Mol. Biol. Cell 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," Nature 2010, 468, 1067; Nicodeme, et al. "Suppression of Inflammation by a Synthetic Histone Mimic," Nature 2010, 468, 1119).

Acetylated histone recognition and bromodomain-containing proteins (such as BET proteins) have been implicated in proliferative disease. BRD4 knockout mice die shortly after transplantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) Mol. Biol. Cell 20:4899-4909). BRD4 also physically associates with Mediator and P-TEFb (CDK9/cyclin T1) to facilitate transcriptional elongation (Yang, et al. (2005) Oncogene 24:1653-1662; Yang, et al. (2005) Mol. Cell 19:535-545). CDK9 is a validated target in chronic lymphocytic leukemia (CLL), and is linked to c-Myc-dependent transcription (Phelps, et al. Blood 113:2637-2645; Rahl, et al. (2010) Cell 141:432-445).

BRD4 is translocated to the NUT protein in patients with lethal midline carcinoma, an aggressive form of human squamous carcinoma (French, et al. (2001) Am. J. Pathol. 159:1987-1992; French, et al. (2003) Cancer Res. 63:304-307). In vitro analysis with RNAi supports a causal role for BRD4 in this recurrent t(15; 19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," Nature 2010, 468, 1067.

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) Cell 138:129-145; LeRoy, et al. (2008) Mol. Cell 30:51-60; Jang, et al. (2005) Mol. Cell 19:523-534; Yang, et al. (2005) Mol. Cell 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," Nature (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus). Indeed, small molecules BET inhibitors have been shown to reactivate HIV from latency in cells containing latent virus (J. Leukoc. Biol. 2012, 92, 1147; Cell Cycle, 2013, 12, 452).

In one aspect, there is provided a compound of Formula I or a pharmaceutically acceptable derivative, polymorph, salt or prodrug thereof

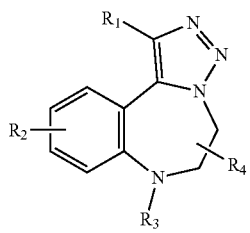

I wherein:

$R_1$ is selected from the group consisting of H, $C_{1-4}$alkyl, $CF_3$, $CF_2H$, $C_{1-4}$alkylXH, $C_{1-4}$alkylOCOR$_5$; wherein X=O, S;

$R_2$ is 0-3 substituents independently selected from the group consisting of $C_{1-4}$alkyl, CN, Cl, Br, I, $C_{3-10}$heterocyclyl, OC$_{1-4}$alkyl, $C_{5-10}$heteroaryl, $C_{1-4}$alkylC$_{6-10}$aryl, $C_{1-4}$alkylC$_{5-10}$heteroaryl, hydroxyl, nitro, COR$_6$, CO$_2$R$_6$, CONR$_5$R$_6$, CONHSO$_2$R$_5$, SO$_2$NHCOR$_5$, CONR$_5$OR$_6$, $C_{1-4}$alkylNR$_5$R$_6$, $C_{1-4}$alkylOR$_6$, NR$_5$R$_6$, NR$_5$COR$_6$, NR$_7$CONR$_5$R$_6$ and NR$_5$CO$_2$R$_6$;

$R_3$ is selected from the group consisting of $C_{1-4}$alkyl, $C_{3-10}$cycloalkyl, $C_{3-10}$heterocyclyl, $C_{6-10}$aryl, $C_{1-4}$alkylC$_{6-10}$aryl;

$R_4$ is 1 to 2 groups on the same or adjacent carbons selected from oxo, $C_{1-4}$alkyl, $C_{1-4}$alkylOH, $C_{1-4}$alkylOCOR$_5$, $C_{1-4}$alkylCONR$_5$R$_6$, $C_{1-4}$alkylC$_{6-10}$aryl, $C_{1-4}$alkylC$_{5-10}$heteroaryl;

$R_5$ and $R_6$ are independently selected from the group consisting of hydrogen, $C_{1-4}$alkyl, $C_{3-10}$cycloalkyl, $C_{3-10}$heterocyclyl, $C_{6-10}$aryl, $C_{5-10}$heteroaryl, $C_{1-4}$alkylC$_{6-10}$aryl and $C_{1-4}$alkylC$_{5-10}$heteroaryl;

alternatively $R_5$ and $R_6$ are bound to the same atom and form an optionally substituted ring that is 4 to 10 carbon atoms in size wherein optionally one or more carbon atoms are replaced with O, S or NR$_7$; and $R_7$ is selected from the group consisting of hydrogen and $C_{1-4}$alkyl and further wherein, unless otherwise stated, each alkyl, cycloalkyl, heterocyyl, heteroaryl, and aryl is optionally substituted.

In another embodiment, the compound of Formula I is a compound of Formula II or a pharmaceutically acceptable derivative, polymorph, salt or prodrug thereof.

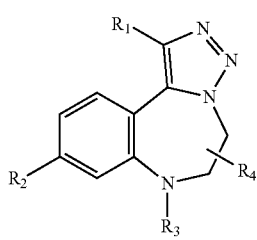

II

In another embodiment, the compound of Formula I is a compound of Formula III or a pharmaceutically acceptable derivative, polymorph, salt or prodrug thereof

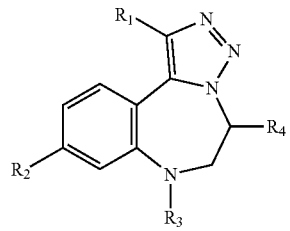

III provided that $R_4$ is limited to 0 to 1 groups.

Further provided is a compound of formula I, II or III or a pharmaceutically acceptable derivative, polymorph, salt or prodrug thereof wherein $R_1$ is selected from the group consisting of H or $C_{1-4}$alkyl;

$R_2$ is 0-3 substituents independently selected from the group consisting of $C_{1-4}$alkyl, CN, Cl, Br, I, $C_{3-10}$heterocyclyl, OC$_{1-4}$alkyl, $C_{5-10}$heteroaryl, $C_{1-4}$alkylC$_{6-10}$aryl, $C_{1-4}$alkylC$_{5-10}$heteroaryl, hydroxyl, nitro, COR$_6$, CO$_2$R$_6$, CONR$_5$R$_6$, CONHSO$_2$R$_5$, SO$_2$NHCOR$_5$, CONR$_5$OR$_6$, $C_{1-4}$alkylNR$_5$R$_6$, $C_{1-4}$alkylOR$_6$, NR$_5$R$_6$, NR$_5$COR$_6$, NR$_7$CONR$_5$R$_6$, and NR$_5$CO$_2$R$_6$;

$R_3$ is $C_{6-10}$aryl;

$R_4$ is 0 to 2 groups on the same or adjacent carbons selected from $C_{1-4}$alkyl, $C_{1-4}$alkylOH, $C_{1-4}$alkylOCOR$_5$, $C_{1-4}$alkylCONR$_5$R$_6$, $C_{1-4}$alkylC$_{6-10}$aryl, $C_{1-4}$alkylC$_{5-10}$heteroaryl;

$R_5$ and $R_6$ are independently selected from the group consisting of hydrogen, $C_{1-4}$alkyl, $C_{3-10}$cycloalkyl, $C_{3-10}$heterocyclyl, $C_{6-10}$aryl, $C_{5-10}$heteroaryl, $C_{1-4}$alkylC$_{6-10}$ aryl and $C_{1-4}$alkylC$_{5-10}$heteroaryl;

alternatively $R_5$ and $R_6$ are bound to the same atom and form an optionally substituted ring that is 4 to 10 carbon atoms in size wherein optionally one or more carbon atoms are replaced with O, S, S(O), SO$_2$, or NR$_7$; and $R_7$ is selected from the group consisting of hydrogen and $C_{1-4}$alkyl and further wherein, unless otherwise stated, each alkyl, cycloalkyl, heterocycyl, heteroaryl, and aryl is optionally substituted.

Preferably, $R_3$ is $C_{6-10}$aryl.

More preferably, $R_3$ is meta or para substituted.

Yet more preferably, $R_3$ is para substituted.

In a preferred form, the substituent of $R_3$ is selected from the group consisting of Cl, F, Br, CN, CH(OH)CRR'(OH), where R and R'=H or $C_{1-4}$alkyl.

In a further preferred form, $R_1$ is $C_{1-4}$alkyl, preferably methyl.

In a preferred form, $R_4$ is selected from the group consisting of H, alkyl, CH$_2$CONR$_2$ (R=H, $C_{1-4}$alkyl), CH$_2$CO$_2$R (R=H, $C_{1-4}$alkyl), CH$_2$NHCOR, (CH$_2$)$_n$hetaryl (wherein n=1-4).

In a preferred form, $R_2$ is selected from the group consisting of CN, $C_{5-10}$heteroaryl, CO$_2$R$_6$, CONR$_5$R$_6$, CONHSO$_2$R$_5$, CONR$_5$OR$_6$, $C_{1-4}$alkylNR$_5$R$_6$.

In a further embodiment, $R_2$ is selected from the group consisting of CN, CONR$_5$R$_6$, CONHSO$_2$R$_5$, CONR$_5$OR$_6$ and $C_{5-10}$heteroaryl.

In another embodiment, $R_2$ is CONR$_5$R$_6$, $R_5$ is H and $R_6$ is $C_{1-4}$alkylC$_{6-10}$aryl.

In yet another embodiment, $R_6$ is 1,1-ethylbenzene.

In one form, $R_2$ is $C_{5-10}$heteroaryl. Preferably, $R_2$ is tetrazole or 3-oxo-1,2,4-isoxazole.

This invention also encompasses pharmaceutical compositions containing prodrugs of compounds of Formula I. Compounds of Formula I having free amino, amido, hydroxy or carboxylic groups can be converted into prodrugs.

Prodrugs include compounds wherein free amino, hydroxy or acid moieties present in compounds of the Formula I are derivatized into functionalities such as carbonates, carbamates, amides and alkyl esters through covalent attachment to the above substituents. Prodrugs also include phosphate derivatives of compounds of Formula I (such as acids, salts of acids, or esters) joined though a phosphorus-oxygen bond to a free hydroxyl of compounds of Formula I. Such prodrug derivatives are prepared to modify the molecular properties of the compound to, for example, improve aqueous solubility or cellular permeability of the parent drug, or permit release of the parent drug at the required site of action. In the presence of particular conditions in vivo, the prodrug moiety is cleaved to release the parent drug. Thus, for example, a hydroxamic acid moiety may be derivatized though esterification of the free hydroxyl to improve cellular permeability. Upon cleavage of the ester moiety inside cells the free drug is released. Likewise amino or hydroxy groups may be derivatized with oxymethyl esters to generate species with improved solubility or cell permeability that upon cleavage release the free drug. Amino groups may also be derivatized as benzyl carbamates where the benzyl group possesses a p-hydroxy moiety: esterification of the hydroxyl group gives a derivative with improved cellular permeability that upon ester cleavage releases the carbamate protecting group thereby liberating the parent drug.

Prodrugs further include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, desmosine, isodesmosine, 3-methylhistidine, norvaline, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

As used herein, the term "halo" or "halogen" refers to fluorine (fluoro), chlorine (chloro), bromine (bromo) or iodine (iodo).

As used herein, the terms "alkyl" and "alkylene" either used alone or in compound terms such as NH(alkyl) or N(alkyl)$_2$, refer respectively to monovalent and divalent straight chain or branched hydrocarbon groups, having 1 to 3, 1 to 4, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

As used herein, the term "alkenyl" refers to a straight chain or branched hydrocarbon groups having one or more double bonds between carbon atoms. Suitable alkenyl groups include, but are not limited to, ethenyl, allyl, propenyl, iso-propenyl, butenyl, pentenyl and hexenyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include O, N and S. Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, 2,2'-dimethyl-[1,3]-dioxolanyl, tetrahydrofuranyl, tetrahydropyranyl, tetrahydropyrrolyl, etc.

The term "heteroaryl" includes a 5- or 6-membered heteroaromatic ring containing one or more heteroatoms selected from O, N and S. Suitable examples of heteroaryl groups include furanyl, thiophenyl, tetrazolyl, 1,2,3-triazolyl, 1,2,4-triazolyl, imidazolyl, pyrazolyl, pyridinyl, pyrimidinyl, oxazolyl, oxadiazolyl, thiazolyl, thiadiazolyl etc. The heteroaromatic ring may be fused to a 5- or 6-membered aromatic or heteroaromatic ring to form a bicyclic aromatic ring system eg benzofuran.

Unless otherwise stated, each alkyl, alkylene, cycloalkyl, alkylaryl, aryl, heterocyclyl, or heteroaryl group may be optionally substituted with one or more of $C_1$-$C_3$alkyl, $C_3$-$C_6$cycloalkyl, $C_6$aryl, heterocyclyl, heteroaryl, $C_1$-$C_3$alkylOH, oxo, alkylaryl, OH, O$C_1$-$C_3$alkyl, halo, CN, NO$_2$, CO$_2$H, CO$_2C_1$-$C_3$alkyl, CONH$_2$, CONH($C_1$-$C_3$alkyl), CON($C_1$-$C_3$alkyl)$_2$, trifluoromethyl, NH$_2$, NH($C_1$-$C_3$alkyl) or N($C_1$-$C_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

Examples of optional substituents also include suitable nitrogen protecting groups (see "Protective Groups in Organic Synthesis" Theodora Greene and Peter Wuts, fourth edition, Wiley Interscience, 2006).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an active metabolite or residue thereof.

Suitable pharmaceutically acceptable salts include, but are not limited to, salts of pharmaceutically acceptable inorganic acids such as hydrochloric, sulfuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Pharmaceutical Salts: Properties, Selection, and Use" P. H. Stahl, C. G. Wermuth, 2nd edition, 2011, Wiley-VCH.

Basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid.

The invention also includes polymorphs of the compounds of present invention, the term polymorph includes different crystal structures but also solvates, such as hydrates and methanolates, thereof.

Uses of Compounds

In another aspect, the invention provides a method for inhibiting activity of a bromodomain-containing protein, or a mutant thereof, in a biological sample comprising the step of contacting said biological sample with a compound of the present invention (e.g. any formulae herein).

In one embodiment, the bromodomain-containing protein is a BET protein.

In a further embodiment, the BET protein is BRD4.

In another aspect, the invention provides a method for inhibiting activity of a bromodomain-containing protein, or a mutant thereof, in a patient comprising the step of administering to said patient a compound of the present invention (e.g. any formulae herein).

In one embodiment, the bromodomain-containing protein is a BET protein.

In other embodiments, the BET protein is BRD4.

In another aspect, the invention provides a method for treating a bromodomain-containing protein-mediated disorder in a patient in need thereof, comprising the step of administering to said patient a compound of the present invention (e.g. any formulae herein).

In another aspect, there is provided use of a compound of the present invention in the preparation of a medicament for the treatment of a bromodomain-containing protein-mediated disorder in a patient in need thereof.

In another aspect, there is provided a compound of the present invention for use in the treatment of a bromodomain-containing protein-mediated disorder in a patient in need thereof.

In one embodiment, the bromodomain-containing protein is a BET protein.

In a further embodiment, the BET protein is BRD4.

In another embodiment, the disorder is a proliferative disorder, inflammatory disease, sepsis, autoimmune disease, or viral infection.

In a further embodiment, the proliferative disorder is cancer.

In certain embodiments, the cancer is adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumour, oral cancer, ovarian cancer, pituitary tumour, primary central nervous system lymphoma, prostate cancer, pancreatic cancer, pharyngeal cancer, renal cell carcinoma, rectal cancer, sarcoma, skin cancer, spinal tumour, small intestine cancer, stomach cancer, T-cell lymphoma, testicular cancer, thyroid cancer, throat cancer, urogenital cancer, urothelial carcinoma, uterine cancer, vaginal cancer, or Wilms' tumour.

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a compound or composition according to the present invention.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "effective amount" means the amount of the subject composition that will elicit the biological or medical response of a tissue, system, animal or human that is being sought by the researcher, veterinarian, medical doctor or other clinician.

The terms "administration of" and or "administering a" compound should be understood to mean providing a compound of the invention to the individual in need of treatment.

In certain embodiments, a compound of the present invention inhibits one or more of BRD2, BRD3, BRD4, BRDT, and/or another member of the bromodomain-containing proteins, or a mutant thereof. In some embodiments, a compound of the present invention inhibits two or more of BRD2, BRD3, BRD4, BRDT, and/or another member of the bromodomain-containing proteins, or a mutant thereof. Compounds of the present invention are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a compound of the present invention, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject. In one embodiment, a human patient is treated with a compound of the invention and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumour, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumour, B-cell chronic lymphocytic leukemia, B-cell prolymphocytic leukemia, B-cell lymphoma, basal cell carcinoma, biliary tract cancer, bladder cancer, blastoma, bone cancer, Brenner tumour, Brown tumour, Burkitt's lymphoma, breast cancer, brain cancer, carcinoma, carcinoma in situ, carcinosarcoma, cartilage tumour, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumour, diffuse large B-cell lymphoma, dysembryoplastic neuroepithelial tumour, dysgerminoma, embryonal carcinoma, endocrine gland neoplasm, endodermal sinus tumour, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumour, gestational choriocarcinoma, giant cell fibroblastoma, giant cell tumour of the bone, glial tumour, glioblastoma multiforme, glioma, gliomatosis cerebri, glucagonoma, gonadoblastoma, granulosa cell tumour, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumour, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumour, malignant triton tumour, mantle cell lymphoma, marginal zone B-cell lymphoma, mast cell leukemia, mediastinal germ cell tumour, medullary carcinoma of the breast, medullary thyroid cancer, medulloblastoma, melanoma, meningioma, merkel cell cancer, mesothelioma, metastatic urothelial carcinoma, mixed Mullerian tumour, mucinous tumour, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumour, oral cancer, osteosarcoma, ovarian cancer, Pancoast tumour, papillary thyroid cancer, paraganglioma, pinealoblastoma, pineocytoma, pituicytoma, pituitary adenoma, pituitary tumour, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumour, sex cord-gonadal stromal tumour, signet ring cell carcinoma, skin cancer, small blue round cell tumours, small cell carcinoma, soft tissue sarcoma, somatostatinoma, soot wart, spinal tumour, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumour, and Wilms' tumour.

In some embodiments, the present invention provides a method of treating a benign proliferative disorder. Such benign proliferative disorders include, but are not limited to, benign soft tissue tumours, bone tumours, brain and spinal tumours, eyelid and orbital tumours, granuloma, lipoma, meningioma, multiple endocrine neoplasia, nasal polyps, pituitary tumours, prolactinoma, pseudotumour cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The invention further relates to a method for treating infectious and noninfectious inflammatory events and autoimmune and other inflammatory diseases by administration of an effective amount of a compound of the present invention to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In some embodiments, the present invention provides a method of treating systemic inflammatory response syndromes such as LPS-induced endotoxic shock and/or bacteria-induced sepsis by administration of an effective amount of a compound of the present invention to a mammal, in particular a human in need of such treatment.

The invention further relates to a method for treating viral infections and diseases by administration of an effective amount of a compound of the present invention to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus (HIV), hepatis B virus, and hepatitis C virus.

The invention further provides a method of treating a subject, such as a human, suffering from one of the above-mentioned conditions, illnesses, disorders or diseases. The method comprises administering a therapeutically effective amount of one or more compound of the present inventions, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more compounds of the present invention.

The invention further provides a method of regulating endogenous or heterologous promoter activity by contacting a cell with a compound of the present invention.

In certain embodiments, the invention provides a method of treating a disorder (as described above) in a subject, comprising administering to the subject identified as in need thereof, a compound of the invention. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumour size or screening for tumour markers where the cell proliferative disorder is cancer) and then administering a therapeutically effective amount of a compound of the invention, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the invention.

The invention further relates to the use of compounds of the present invention for the production of pharmaceutical compositions which are employed for the treatment and/or prophylaxis and/or amelioration of the diseases, disorders, illnesses and/or conditions as mentioned herein.

The invention further relates to the use of compounds of the present invention for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Compounds of the present invention are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

According to some embodiments, the invention relates to a method of inhibiting bromodomain-containing proteins in a biological sample comprising the step of contacting said biological sample with a compound of the present invention, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a compound of the present invention, or a composition thereof.

The term "biological sample", as used herein, includes, without limitation, cell cultures or extracts thereof; biopsied material obtained from a mammal or extracts thereof; and blood, saliva, urine, faeces, semen, tears, or other body fluids or extracts thereof. Inhibition of activity of a protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a compound of the present invention, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a compound of the present invention or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a compound of the present invention to treat proliferative diseases and cancer. Examples of therapies or anticancer agents that may be used in combination with compounds of formula I include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumour necrosis factor (TNF), hyperthermia and cryotherapy, an agent to attenuate any adverse effects (e.g., an antiemetic), and any other approved chemotherapeutic drug.

A compound of the present invention may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; an Hsp90 inhibitor; an HDAC inhibitor; a kinesin spindle protein inhibitor; an antitumour antibiotic; a nitrosourea; a compound targeting/decreasing protein or lipid kinase activity; a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubule polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cisplatin, cisplatinum, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid.

Exemplary antiproliferative antibodies include trastuzumab, trastuzumab-DM1 cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib and carfilzomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and busulfan; hypomethylating agents such as decitabine and azacytadine; BTK inhibitors such as ibrutinib; PI3Kgamma and PI3Kdelta inhibitors such as idelalisib and duvelisib; SYK inhibitors such as entospletinib; and ALK inhibitors, which are compounds which target, decrease or inhibit anaplastic lymphoma kinase.

Exemplary Flt-3 inhibitors include quizartinib, PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; and radicicol.

Exemplary HDAC inhibitors include vorinostat, trichostatin A, romidepsin, panobinostat, entinostat, mocetinostat, belinostat and rocilinostat.

The phrase "a compound targeting/decreasing a protein or lipid kinase activity" as used herein includes a protein tyrosine kinase and/or serine and/or threonine kinase inhibitor or lipid kinase inhibitor, such as a) a compound targeting, decreasing or inhibiting the activity of the kinase ALK such as ceritinib and crizotinib; b) a compound targeting, decreasing or inhibiting the activity of the kinase MEK such as trametinib; c) RAF inhibitors such as dabrafenib and vemurafenib; d) a compound targeting, decreasing or inhibiting the activity of the epidermal growth factor family of receptor tyrosine kinases (EGFR, ErbB2, ErbB3, ErbB4 as homo- or heterodimers) and their mutants, such as trastuzumab, cetuximab, gefitinib, erlotinib, lapatinib, afatinib, neratinib; e) a compound targeting, decreasing or inhibiting the activity of the JAK family of receptor tyrosine kinases (JAK1, JAK2, JAK3, TYK2) such as tofacitinib, ruxolitinib, momelotinib, baricitinib; f) a compound targeting, decreasing or inhibiting the activity of members of the c-Abl family, their gene-fusion products (e.g. Bcr-Abl kinase) and mutants, such as imatinib or nilotinib, dasatinib, bosutinib; g) multikinase inhibitors such as sorafenib, sunitinib, cabozantinib, regorafenib, vandetanib; and h) mTOR inhibitors such as everolimus and sirolimus.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide, lenalidomide and TNP-470.

Additional exemplary chemotherapeutic compounds, one or more of which may be used in combination with compounds of the present invention, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, angiostatin, endostatin, anthranilic acid amides, bevacizumab, rhuMAb, rhuFab, macugen; FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a compound of the present invention may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon {e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a compound of the present invention, can be prepared and administered as described in the art.

Compounds of the present invention can be administered alone or in combination with one or more other therapeutic compounds, possible combination therapy taking the form of fixed combinations or the administration of a compound of the present invention and one or more other therapeutic compounds being staggered or given independently of one another, or the combined administration of fixed combinations and one or more other therapeutic compounds. Compounds of the present invention can besides or in addition be administered especially for tumour therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Such additional agents may be administered separately from a composition containing a compound of the present invention, as part of a multiple dosage regimen. Alternatively, those agents may be part of a single dosage form, mixed together with a compound of the present invention in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, an embodiment of the invention provides a single unit dosage form comprising a compound of the present invention, an additional therapeutic agent, and a pharmaceutically acceptable carrier, adjuvant, or vehicle for use in the methods of the invention.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compounds of the present invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a compound of the present invention. Implantable devices coated with a compound of this invention are another embodiment of the present invention.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

In another aspect, the invention provides a method of method of synthesizing a compound of any formulae as described herein. Another embodiment is a method of making a compound of any of the formulae herein using any one, or combination of, reactions delineated herein. The method can include the use of one or more intermediates or chemical reagents delineated herein.

Compositions and Administration

In another aspect, the invention provides for a composition comprising a compound of any of the formulae herein, and a pharmaceutically acceptable excipient, for example an adjuvant, carrier or vehicle.

In one embodiment, the invention provides for a composition, in combination with an additional therapeutic agent.

According to another embodiment, the present invention provides a method of inhibiting a bromodomain-containing protein (such as a BET protein, e.g., BRD2, BRD3, BRD4, and/or BRDT) using a composition comprising a compound of the invention or a pharmaceutically acceptable derivative thereof and a pharmaceutically acceptable carrier, adjuvant, or vehicle. The amount of a compound of the invention in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "pharmaceutically acceptable excipient" refers to a non-toxic excipient that does not destroy the pharmacological activity of the compound with which it is formulated. Pharmaceutically acceptable excipients such as carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compounds of the present invention can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

An appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. The amount of a compound of the present invention in the composition will also depend upon the particular compound in the composition.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

Chemistry
General Description of Chemistry

The 6,7-dihydro-benzo[f][1,2,3]triazolo[1,5-d][1,4]diazepine I compounds of the present disclosure may be prepared by the following illustrative pathways.

Conversion of a suitably substituted 6,7-dihydro-benzo[f][1,2,3]triazolo[1,5-d][1,4]diazepine A, where X is preferably iodo, bromo or triflate, to the substituted derivative I may be achieved through a metal-mediated cross-coupling reaction with a suitably functionalized coupling partner. A typical metal catalyst is a palladium species and typical coupling partners are boronic acids or esters (Suzuki coupling: *Chem Rev.* 1995, 95, 2457), stannanes (Stille coupling: *Synthesis* 1992, 803-815.), Grignard reagents (Kumada coupling: *Org Synth.* 1988, Coll. Vol. 6, 407), organozinc species (Negishi coupling: *J. Organomet Chem.* 2002, 653, 34), alkenes (Heck reaction: *Tetrahedron* 2001, 57, 7449) or alkynes (Sonogashira coupling: *Synlett* 2009, 2896). The Suzuki coupling is the preferred coupling method and is typically performed in a solvent such as DME, THF, DMF, ethanol, propanol, toluene, or 1,4-dioxane in the presence of a base such as $K_2CO_3$, LiOH, $Cs_2CO_3$, NaOH, KF or $K_3PO_4$. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3$.

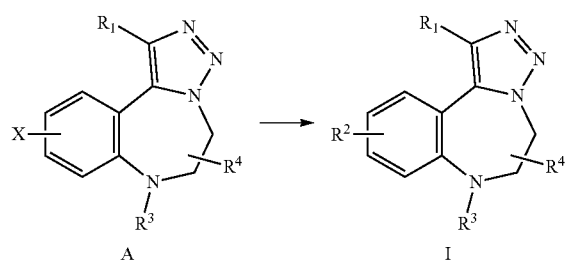

A        I

The substituent(s) $R^4$ may be introduced into the 6,7-dihydro-benzo[f][1,2,3]triazolo[1,5-d][1,4]diazepine derivatives D by alkylation of a benzo[f][1,2,3]triazolo[1,5-d][1,4]diazepin-6(7H)-one derivative B. Conditions for such alkylations a to an amide carbonyl are well known to those skilled in the art and involve reaction of the benzo[f][1,2,3]triazolo[1,5-d][1,4]diazepin-6(7H)-one derivative B with a base and reaction of the anion thus generated with an alkylating agent in a solvent. Preferred bases include sodium hexamethyldisilazide, potassium hexamethyldisilazide, lithium diisopropylamide, and sodium hydroxide. Preferred alkylating agents include substituted alkyl iodides, substituted alkyl bromides and substituted alkyl chlorides. Preferred solvents include tetrahydrofuran, dimethylformamide, HMPA, and acetonitrile at temperatures from −80° C. to reflux. The substituted benzo[f][1,2,3]triazolo[1,5-d][1,4] diazepin-6(7H)-one derivative C may be further alkylated under the conditions described above or converted to the 6,7-dihydro-benzo[f][1,2,3]triazolo[1,5-d][1,4]diazepine derivatives D by exposure to a reducing agent in a suitable solvent. Preferred reducing agents include borane, lithium aluminium hydride, DIBAL-H, lithium borohydride, and sodium borohydride with additives such as TFA. Preferred solvents include tetrahydrofuran.

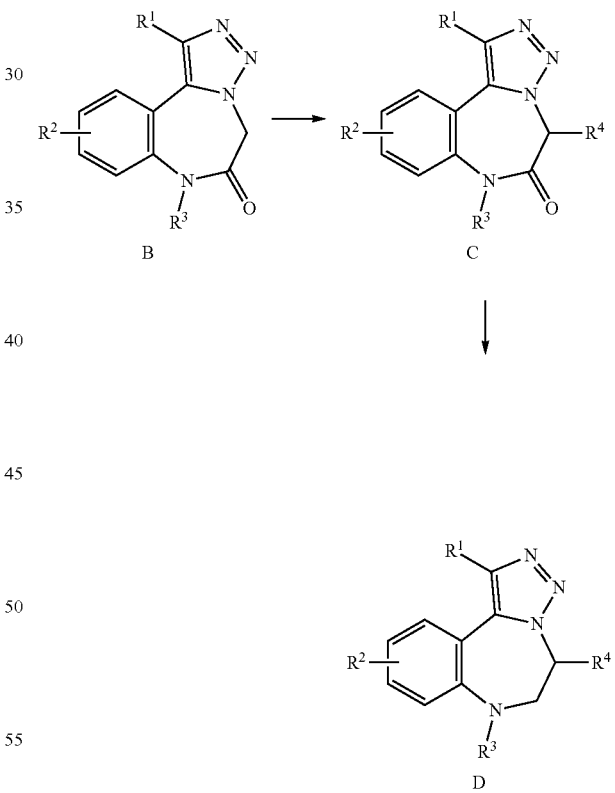

Alternatively substituent(s) $R^4$ may be introduced into the 6,7-dihydro-benzo[f][1,2,3]triazolo[1,5-d][1,4]diazepine derivatives E by reductive alkylation of a benzo[f][1,2,3]triazolo[1,5-d][1,4]diazepin-6(7H)-one derivative B. Methods for such transformations are known to those skilled in the art and the preferred method involves exposure of B to 2,6-di-tert-butyl-4-methylpyridine and triflic anhydride, followed by treatment with a Grignard reagent (*J. Org. Chem.* 2013, 78, 8305-8311).

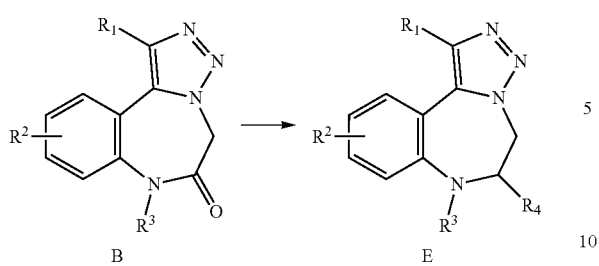

B → E

The benzo[f][1,2,3]triazolo[1,5-d][1,4]diazepin-6(7H)-one derivatives I may be prepared from anilines F in a stepwise procedure involving acylation of the aniline nitrogen with α-chloroacetyl chloride and subsequent reaction with sodium azide followed by heating. The acylation of F is conducted under conditions well known to those skilled in the art and typically involves reaction between the aniline and α-chloroacetyl chloride or substituted version thereof, in an aprotic solvent such as dichloromethane, toluene or tetrahydrofuran, in the presence of a base such as triethylamine or potassium carbonate. Nucleophilic acylation catalysts such as DMAP may be added to assist the reaction. The chloride G thus formed is then reacted with an azide source such as sodium azide in an inert solvent such as toluene, dimethylformamide or N-methylpyrrolidinone to generate an azido intermediate that is subsequently heated to effect a [3+2] cycloaddition thereby generating the benzo[f][1,2,3]triazolo[1,5-d][1,4]diazepin-6(7H)-one C.

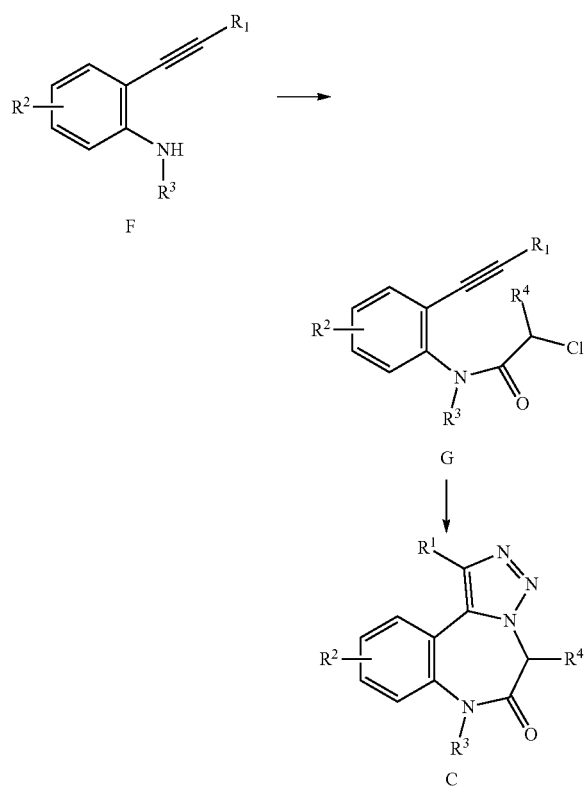

Anilines F may be commercially available or may be prepared by reaction of the aniline derivatives H, where X is preferably bromo, iodo or triflate, with terminal acetylene derivatives in the presence of a suitable metal catalyst. The preferred method is the Sonogashira coupling (*Comp. Org. Syn.* 1991, 3, 551-561) where a copper acetylide species is formed from a terminal acetylene and a copper (I) salt such as cuprous iodide using a palladium catalyst such as (PPh$_3$)$_2$PdCl$_2$ in the presence of an amine base such as triethylamine.

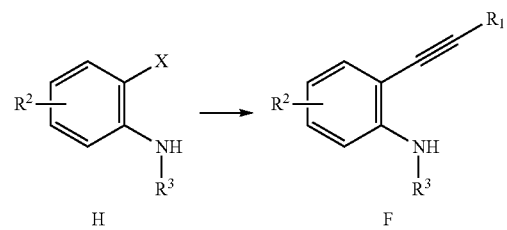

H → F

Alternatively anilines F may be obtained in a stepwise manner from the aniline J where Y is preferably cyano, ester, acid, acid halide or amido. Reduction of the group Y under conditions well known to those skilled in the art would generate the aldehyde K which would then be converted to the desired alkyne derivative F under conditions known to those skilled in the art. Preferred methods for reduction of J include DIBAL-H, lithium tri(tert-butoxyaluminum hydride, or may involve reduction to the corresponding alcohol (with, for example, lithium aluminium hydride) and subsequent oxidation to the aldehyde J (using for example a Swern oxidation, TPAP or manganese dioxide). Reduction reactions are preferably performed cold in solvents such as tetrahydrofuran. Preferable methods for conversion of the aldehyde J to the alkyne F involves reactions such as the Seyferth-Gilbert homologation [*J. Org. Chem.*, 1982, 47, 1837-1845] using the Bestmann-Ohira reagent or variations thereof. Terminal acetylenes formed by these reactions (R$^1$=H) could be further elaborated (R$^1$≠H) using procedures such as the Corey-Fuchs reaction. A preferred method to generate alkynes F where R$^1$=Me, involves addition of the anion of ethyl phenylsulfone to aldehydes K and effecting a double-elimination procedure by sequential treatment with ClP(O)(OEt)$_2$, and t-BuOK in one-pot [*Synlett* 2007, 1909-1912]. Practitioners skilled in the art will appreciate that in some instances described above the aniline will need to be derivatized (i.e. protected) for the reaction to proceed with reasonable yield and efficiency. Appropriate protecting groups are well-known to those skilled in the art and can be found in textbooks such as see "Protective Groups in Organic Synthesis" by Theodora Greene and Peter Wuts, fourth edition, Wiley Interscience, 2006.

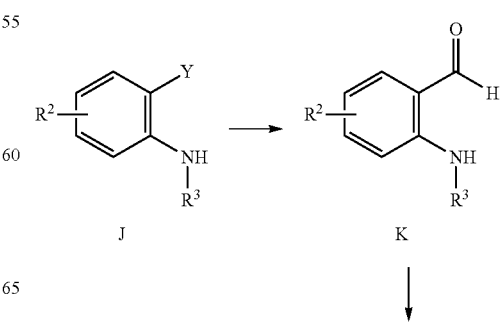

J → K

↓

-continued

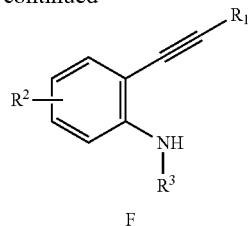

F

The anilines H and J are obtained by reaction of the corresponding primary aniline under various conditions to introduce $R^3$. Common procedures for such a transformation include alkylation with alkyl halides; imine formation with suitable aldehydes followed by reduction (i.e. reductive amination); or a coupling reaction with aryl or alkyl boronic acid derivatives (or stannanes, siloxanes, iodonium salts) in the presence of a suitable metal catalyst such as Cu(II) salts (e.g. Chan-Lam coupling: Tetrahedron 2012, 68, 7735). Alternatively, $R^3$ may be introduced through a transition metal catalysed amination reaction (Buchwald-Hartwig Reaction). Typical catalysts for such transformations include $Pd(OAc)_2/P(t-Bu)_3$, $Pd_2(dba)_3$/Xantphos and $Pd(OAc)_2$/BI-NAP. These reactions are typically carried out in solvents such as toluene or dioxane, in the presence of bases such as caesium carbonate or sodium or potassium tert-butoxide at temperatures ranging from room temperature to reflux (e.g. Hartwig, J. F., Angew. Chem. Int. Ed. 1998, 37, 2046).

It will be appreciated that the methods described above are illustrative and the reaction sequences may be conducted in an alternative order to that described above. Further elaboration of the compounds prepared as described above may also be undertaken, using procedures well known to those skilled in the art, to prepare compounds of the present invention.

General Chemistry Methods

Nuclear magnetic resonance ($^1$H NMR, 600 MHz and 300 MHz and $^{13}$C NMR, 150 MHz and 75 MHz) spectra were obtained at 300 K with $CDCl_3$ as the solvent unless otherwise indicated. Chemical shifts are reported in ppm on the δ scale and referenced to the appropriate solvent peak. Analytical thin-layer chromatography (TLC) was performed on Merck silica gel 60 F254 aluminium-backed plates and visualized with short wavelength UV (254 nm) absorbance. Chromatography was performed using either the Combi-Flash® Rf purification system (Teledyne, ISCO, Lincoln, Nebr., USA) with pre-packed silica gel columns (particle size 0.040-0.063 mm), or using a Flash chromatography employing a glass column with silica gel 60 (particle size 0.040-0.063 mm). Anhydrous solvents were dried using an automated solvent purification system (MBraun SPS, Garching, Germany). All commercial reagents were used as received.

Liquid chromatography mass spectroscopy (LCMS) was carried out using one of either two different methods; Method A) Finnigan LCQ Advantage Max using reverse phase high performance liquid chromatography (HPLC) analysis (column: Gemini 3µ C18 20×4.0 mm 110 Å) Solvent A: Water 0.1% Formic Acid, Solvent B: Acetonitrile 0.1% Formic Acid, Gradient: 10-100% B over 10 min Detection: 100-600 nm and electrospray ionisation (ESI) in positive mode with source temperature 300° C. Method B) (5 min method): LC model: Agilent 1200 (Pump type: Binary Pump, Detector type: DAD) MS model: Agilent G6110A Quadrupole. Column: Xbridge-C18, 2.5 µm, 2.1× 30 mm. Column temperature: 30° C. Acquisition of wavelength: 214 nm, 254 nm. Mobile phase: A: 0.07% HCOOH aqueous solution, B: MeOH. Run time: 5 min. MS: Ion source: ES+ (or ES−). MS range: 50~900 m/z. Fragmentor: 60. Drying gas flow: 10 L/min. Nebulizer pressure: 35 psi. Drying gas temperature: 350° C. Vcap: 3.5 kV.

Preparative Mass-directed LC

Method A:

Instrument: Waters ZQ 3100-Mass Detector, Waters 2545-Pump, Waters SFO System Fluidics Organizer, Waters 2996 Diode Array Detector, Waters 2767 Sample Manager LC conditions: Reverse Phase HPLC analysis. Column: XBridge™ C18 5 µm 19×50 mm. Injection Volume 500 µL; Solvent A: Water 0.1% Formic Acid. Solvent B: MeCN 0.1% Formic Acid; Gradient: 5% B over 4 min then 5-100% B over 8 min then 100% B over 4 min; Flow rate: 19 mL/min. Detection: 100-600 nm. MS conditions: Ion Source: Single-quadrupole; Ion Mode: ES positive. Source Temp: 150° C.; Desolvation Temp: 350° C. Detection: Ion counting. Capillary (KV)-3.00. Cone (V): 30 Extractor (V): 3 RF Lens (V): 0.1 Scan Range: 100-1000 Amu Scan Time: 0.5 sec; Acquisition time: 10 min Gas Flow: Desolvation L/hour-650; Cone L/hour-100

Method B:

Instrument type: VARIAN 940 LC. Pump type: Binary Pump. Detector type: PDA

LC conditions: Column: Waters SunFire prep C18 OBD, 5 µm, 19×100 mm. Acquisition wavelength: 214 nm, 254 nm. Mobile Phase: A: 0.07% TFA aqueous solution, B: MeOH, 0.07% TFA.

Abbreviations

ACN Acetonitrile

AD-mix AD-mix-alpha

EA Ethyl acetate cHex Cyclohexane

DAST Diethylaminosulfur trifluoride

DCM Dichloromethane

DIPEA Diisopropylethylamine

DME 1,2-Dimethoxyethane

DMF N,N-Dimethylformamide

DMSO Dimethylsulfoxide

EtOAc Ethyl acetate $K_3PO_4$ Tripotassium phosphate

Lawesson's Reagent 2,4-Bis(4-methoxyphenyl)-1,3,2,4-dithiadiphosphetane-2,4-dithione $LiAlH_4$ Lithium aluminium hydride m-CPBA meta-chloroperoxybenzoic acid MeOH Methanol MsCl Methanesulfonyl chloride MW Microwave HATU (O-(7-azabenzotriazol-1-yl)-N,N,N',N'-tetramethyluronium hexafluorophosphate)

PE Petroleum ether

RT Room temperature

TFA 2,2,2-Trifluoroethanoic acid

THF Tetrahydrofuran

TBAF Tetra-n-butylammonium fluoride

Xantphos 4,5-Bis(diphenylphosphino)-9,9-dimethylxanthene

Xphos 2-Dicyclohexylphosphino-2',4',6'-triisopropylbiphenyl

SPECIFIC EXAMPLES

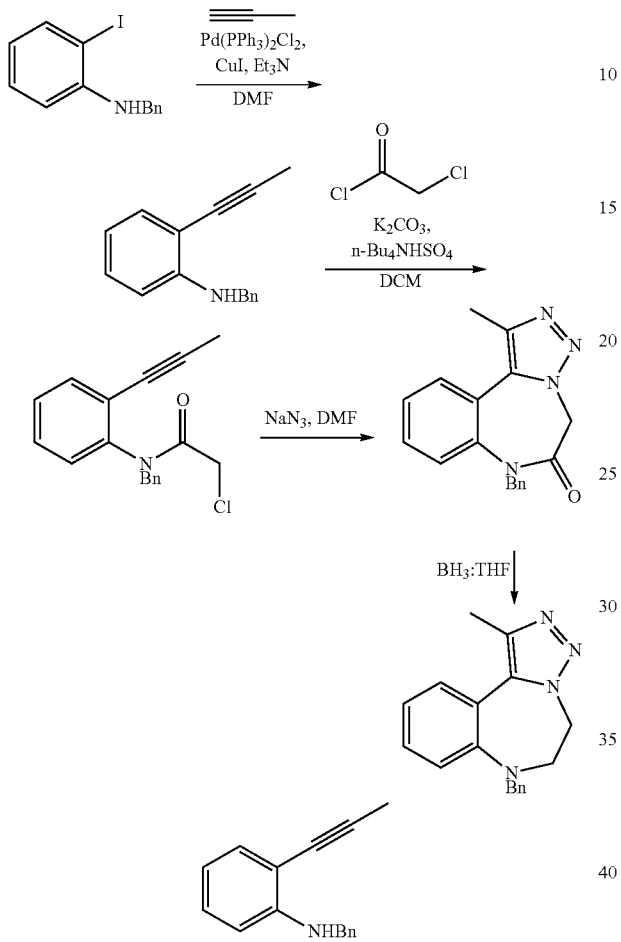

Step 1: N-benzyl-2-(prop-1-yn-1-yl)aniline

A screw cap reaction vessel was charged with a stirring rod, N-benzyl-2-iodoaniline [*Org. Lett.*, 2013, 15 (13), 3274-3277] (1.00 g, 3.23 mmol), Pd(PPh$_3$)2Cl$_2$ (50 mg, 0.07 mmol) and CuI (40 mg, 0.2 mmol). The vessel was evacuated and backfilled with nitrogen (3 times) then triethylamine (5 mL) and DMF (2.5 mL) were added and the mixture was cooled to −78° C. Propyne (3.8 mL, 4.8 mmol) was then condensed into the mixture via a pre-cooled needle (volume measured by displacement). The reaction vessel was then quickly sealed with a screw cap and the cooling bath was removed and the mixture was stirred overnight at RT. The reaction mixture was then poured into diethyl ether (10 mL) and washed with water (3×5 mL). The aqueous phase was then extracted with diethyl ether (3×5 mL) and the combined organic fractions were then washed with brine (5 mL), dried with MgSO$_4$, filtered and concentrated under reduced pressure. The crude material was then purified by flash chromatography (gradient elution 2:98 to 5:95, v/v, EtOAc:cyclohexane) to give N-benzyl-2-(prop-1-yn-1-yl)aniline (690 mg, 98%) as a viscous brown oil.

LCMS (Method C): 6.00 min
m/z [MH]$^+$=222.3;
$^1$H-NMR (600 MHz, CDCl$_3$): δ 7.35 (m, 5H), 7.27 (m, 1H), 7.10-7.07 (m, 1H), 6.61-6.58 (m, 1H), 6.52 (d, J=8.3 Hz, 1H), 4.42 (s, 2H), 2.10 (s, 3H).

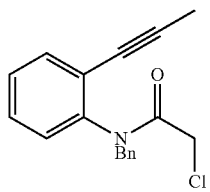 [SMILES: CC#Cc1ccccc1N(Cc1ccccc1)C(=O)CCl]

Step 2: N-benzyl-2-chloro-N-(2-(prop-1-yn-1-yl)phenyl)acetamide

To a magnetically stirred solution of chloro acetylchloride (540 μL, 6.80 mmol) in DCM (20 mL) was added N-benzyl-2-(prop-1-yn-1-yl)aniline (1.00 mg, 4.50 mmol) in DCM (20 ml). Tetra-n-butylammonium hydrogensulfate (200 μL of a ca. 55% solution in water) was then added, followed by potassium carbonate (940 mg, 6.80 mmol). After 1 h the reaction mixture was washed with HCl (2×10 mL of a 1 M solution), then NaOH (2×10 mL of a 1 M solution). The combined aqueous phases were extracted with EtOAc (3×5 mL) and the combined organic phase was washed with brine (10 mL), dried with MgSO$_4$, filtered and concentrated under reduced pressure. The crude material was purified my flash chromatography (gradient elution, 5:95 to 1:9, v/v, EtOAc:cyclohexane) to give N-benzyl-2-chloro-N-(2-(prop-1-yn-1-yl)phenyl)acetamide (1.22 g, 91%) as a viscous yellow oil.

LCMS (Method B): 6.80 min
m/z [MH]+=298.1;
$^1$H-NMR (600 MHz, CDCl$_3$): δ 7.44 (d, J=7.7 Hz, 1H), 7.28-7.23 (m, 4H), 7.20-7.16 (m, 3H), 6.83 (d, J=7.9 Hz, 1H), 5.36 (d, J=14.3 Hz, 1H), 4.41 (d, J=14.2 Hz, 1H), 3.92-3.90 (m, 1H), 3.81 (dd, J=13.7, 1.3 Hz, 1H), 2.00 (s, 3H).

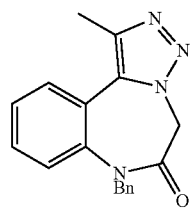 [SMILES: Cc1nnn2c1-c1ccccc1N(Cc1ccccc1)C(=O)C2]

Step 3: 7-benzyl-1-methyl-5H-benzo[f][1,2,3]triazolo[1,5-d][1,4]diazepin-6(7H)-one To a magnetically stirred solution of N-benzyl-2-chloro-N-(2-(prop-1-yn-1-yl)phenyl)acetamide (34 mg, 0.11 mmol) in DMF (0.5 mL) was added sodium azide (18 mg, 0.29 mmol). The mixture was heated to 100° C. for 1 h the temperature was increased to 140° C. for 2 h. the reaction mixture was poured into EtOAc (5 mL), washed with water (5 mL) and the organic phase was dried with Na$_2$SO$_4$, filtered and concentrated under reduced pressure. The crude material was purified by flash chromatography (elution, 1:9, v/v, EtOAc/cyclohexane) to give 7-benzyl-1-methyl-5H-benzo[f][1,2,3]triazolo[1,5-d][1,4]diazepin-6(7H)-one (18 mg, 54%) as a white solid.

LCMS (Method B): 6.27 min m/z [MH]$^+$=305.3

$^1$H-NMR (600 MHz, CDCl$_3$): δ 7.46-7.43 (m, 3H), 7.35-7.33 (m, 1H), 7.18-7.16 (m, 3H), 6.90 (dd, J=6.4, 2.4 Hz, 2H), 5.47 (d, J=14.1 Hz, 1H), 5.19 (d, J=15.5 Hz, 1H), 4.90 (d, J=15.5 Hz, 1H), 4.62 (d, J=14.1 Hz, 1H), 2.46 (s, 3H).

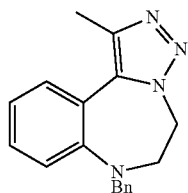 [SMILES: Cc1nnn2c1-c1ccccc1N(Cc1ccccc1)CC2]

Step 4: 7-benzyl-1-methyl-6,7-dihydro-5H-benzo[f][1,2,3]triazolo[1,5-d][1,4]diazepine To a magnetically stirred solution of 7-benzyl-1-methyl-5H-benzo[f][1,2,3]triazolo[1,5-d][1,4]diazepin-6(7H)-one (80 mg, 0.26 mmol) in THF (1 mL) was added borane (1.3 mL of a 1 M solution in THF, 1.3 mmol) and the mixture was heated to reflux for 16 h. The mixture was cooled and MeOH (2 mL) was added and the solution was concentrated under reduced pressure. This process was repeated a further 2 times. The crude material was purified by flash chromatography (gradient elution, 1:9 to 1:4, v/v, EtOAc:cyclohexane) to give 7-benzyl-1-methyl-6,7-dihydro-5H-benzo[f][1,2,3]triazolo[1,5-d][1,4]diazepine (44 mg, 57%) as a white solid.

LCMS (Method B): 7.11 min m/z [MH]$^+$=291.3;

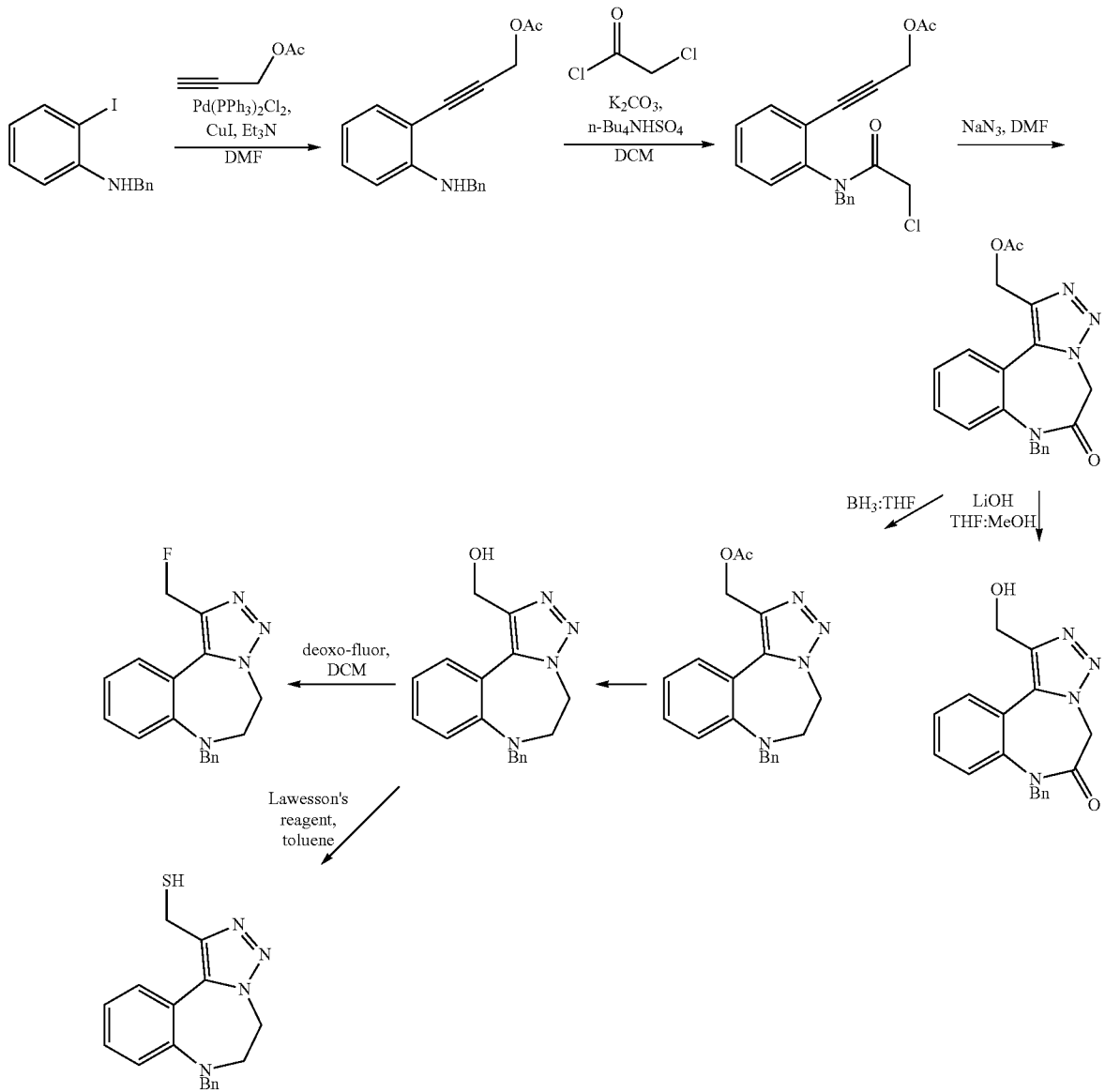

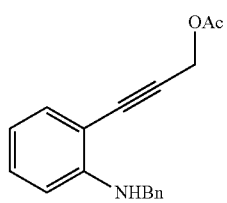

Step 1: 3-(2-(benzylamino)phenyl)prop-2-yn-1-yl acetate

A 100 mL flask was charged with Pd(PPh$_3$)$_4$ (654 mg, 0.57 mmol) and CuI (216 mg, 1.13 mmol) then the flask was evacuated and backfilled with nitrogen. N-Benzyl-2-iodoaniline [*Org. Lett.*, 2013, 15, 3274-3277] (3.50 g, 11.32 mmol) in THF was then added followed by propargyl acetate (1.69 mL, 16.98 mmol) and triethylamine (5 mL). The mixture was stirred for 2 h at room temperature then concentrated onto SiO$_2$. The ensuing solid was subjected to flash chromatography (gradient elution, 0:1 to 1:4, v/v, EtOAc:cyclohexane) to give 3-(2-(benzylamino)phenyl)prop-2-yn-1-yl acetate (2.87 g, 98%) as a viscous orange oil.

LCMS (Method b): 5.10 min m/z [MH]$^+$=279.0

$^1$H-NMR (600 MHz, CDCl$_3$): δ 7.36-7.28 (m, 6H), 7.16-7.13 (m, 1H), 6.63 (t, J=7.5 Hz, 1H), 6.56 (d, J=8.3 Hz, 1H), 4.92 (s, 2H), 4.43 (s, 2H), 2.08 (d, J=0.7 Hz, 3H).

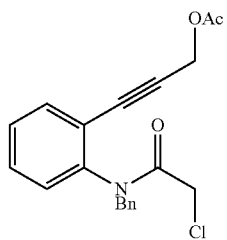 [SMILES: CC(=O)OCC#Cc1ccccc1N(Cc1ccccc1)C(=O)CCl]

Step 2: 3-(2-(N-benzyl-2-chloroacetamido)phenyl)prop-2-yn-1-yl acetate

To a magnetically stirred solution of 3-(2-(benzylamino)phenyl)prop-2-yn-1-yl acetate (2.85 g, 10.2 mmol) in DCM (100 mL) was added chloroacetyl chloride (1.217 mL, 15.3 mmol) followed by tetra-npbutylammonium hydrogensulfate (1.0 mL of a ca. 55% aqueous solution) and potassium carbonate (2.12 g, 15.3 mmol). The mixture was stirred vigorously for 2 h then the organic phase was washed with HCl (2×30 mL of a 0.1 M solution), then with NaHCO$_3$ (2×30 mL of a saturated aqueous solution). The organic phase was dried with MgSO$_4$, filtered and concentrated under reduced pressure. The crude material was purified by flash chromatography (gradient elution, 0:1 to 2:3, v/v, EtOAc:cyclohexane) to give 3-(2-(N-benzyl-2-chloroacetamido)phenyl)prop-2-yn-1-yl acetate (3.06 g, 84%) as an orange oil.

LCMS (Method A): 5.55 min m/z [MH]$^+$=355.7

$^1$H-NMR (600 MHz, CDCl$_3$): δ 7.50 (d, J=7.5 Hz, 1H), 7.31 (d, J=7.4 Hz, 1H), 7.27-7.23 (m, 4H), 7.18 (t, J=3.3 Hz, 2H), 6.88 (d, J=7.8 Hz, 1H), 5.31 (d, J=14.3 Hz, 1H), 4.79 (d, J=1.2 Hz, 2H), 4.44 (d, J=14.3 Hz, 1H), 3.89 (d, J=13.5 Hz, 1H), 3.78 (d, J=13.5 Hz, 1H), 2.14 (s, 3H).

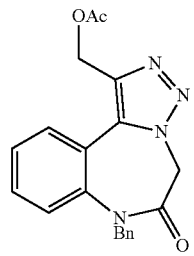 [SMILES: CC(=O)OCc1nnn2c1-c1ccccc1N(Cc1ccccc1)C(=O)C2]

Step 3: (7-benzyl-6-oxo-6,7-dihydro-5H-benzo[f][1,2,3]triazolo[1,5-d][1,4]diazepin-1-yl)methyl acetate A magnetically stirred solution of 3-(2-(N-benzyl-2-chloroacetamido)phenyl)prop-2-yn-1-yl acetate (3.00 g, 8.43 mmol) and sodium azide (1.37 g, 21.08 mmol) in DMF (25 mL) was heated to 100° C. for 1 h then the temperature was raised to 115° C. for 3 h. The cooled mixture was then concentrated and the residue was taken up in EtOAc (50 mL) and washed with water (2×5 mL). the organic phase was dried with MgSO$_4$, filtered and concentrated under reduced pressure. The crude material was purified by flash chromatography (gradient elution, 0:1 to 1:0, v/v, EtOAc:cyclohexane) to give (7-benzyl-6-oxo-6,7-dihydro-5H-benzo[f][1,2,3]triazolo[1,5-d][1,4]diazepin-1-yl)methyl acetate (2.14 g, 70%) as a brown solid.

LCMS (Method A) 5.02 min m/z [MH]$^+$=363.1

$^1$H-NMR (600 MHz, CDCl$_3$): δ 7.56 (dd, J=7.8, 0.9 Hz, 1H), 7.49-7.45 (m, 2H), 7.37-7.34 (m, 1H), 7.16 (dt, J=3.1, 1.6 Hz, 3H), 6.90-6.88 (m, 2H), 5.52 (d, J=14.2 Hz, 1H), 5.42 (d, J=12.9 Hz, 1H), 5.23 (d, J=15.5 Hz, 1H), 5.04 (d, J=12.9 Hz, 1H), 4.88 (d, J=15.5 Hz, 1H), 4.64 (d, J=14.2 Hz, 1H), 2.07 (s, 3H).

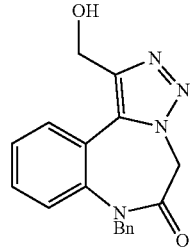

Step 4: 7-benzyl-1-(hydroxymethyl)-5H-benzo[f][1,2,3]triazolo[1,5-d][1,4]diazepin-6(7H)-one To a magnetically stirred solution of (7-benzyl-6-oxo-6,7-dihydro-5H-benzo[f][1,2,3]triazolo[1,5-d][1,4]diazepin-1-yl)methyl acetate (60 mg, 0.17 mmol) in THF (2 mL) and water (0.5 mL) was added lithium hydroxide monohydrate (58 mg, 1.4 mmol). The mixture was stirred for 4 days at room temperature and then neutralized with HCl (1 M) solvent was removed under reduced pressure. The residue was taken up in EtOAc (5 mL) and washed with water (2 mL). The organic phase was dried with MgSO$_4$, filtered and concentrated under reduced pressure to give 7-benzyl-1-(hydroxymethyl)-5H-benzo[f][1,2,3]triazolo[1,5-d][1,4]diazepin-6(7H)-one (54 mg, 99%) as a white solid.

¹H-NMR (600 MHz, CD₃OD): δ 7.28 (dt, J=17.7, 8.4 Hz, 4H), 7.19-7.16 (m, 2H), 7.08 (d, J=7.3 Hz, 1H), 6.69 (t, J=7.4 Hz, 1H), 6.60 (d, J=8.3 Hz, 1H), 4.76 (q, J=18.0 Hz, 2H), 4.54 (q, J=17.2 Hz, 2H), 4.28 (s, 2H).

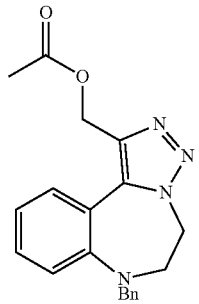 [SMILES: CC(=O)OCc1nnn2c1-c1ccccc1N(Cc1ccccc1)CC2]

Step 5: (7-benzyl-6,7-dihydro-5H-benzo[f][1,2,3]triazolo[1,5-d][1,4]diazepin-1-yl)methyl acetate To a magnetically stirred solution of (7-benzyl-6-oxo-6,7-dihydro-5H-benzo[f][1,2,3]triazolo[1,5-d][1,4]diazepin-1-yl)methyl acetate (1.00 g, 2.76 mmol) in THF (27 mL) was added borane (27 mL of a 1 M solution in THF, 27.59 mmol). The mixture was heated to 90° C. for 16 h then concentrated under reduced pressure. The residue was taken up in methanol (10 mL) and heated to reflux for 2 h before being concentrated under reduced pressure. The crude material was purified by flash chromatography (gradient elution, 0:1 to 1:0, v/v, EtOAc/cyclohexane) to give (7-benzyl-6,7-dihydro-5H-benzo[f][1,2,3]triazolo[1,5-d][1,4]diazepin-1-yl)methyl acetate (570 mg, 58%) as a pale yellow solid.

LCMS (Method A) 5.02 min
m/z [MH]⁺=363.1;

¹H-NMR (600 MHz, CDCl₃): δ 7.47 (dd, J=7.7, 1.3 Hz, 1H), 7.40-7.37 (m, 1H), 7.30-7.27 (m, 2H), 7.25 (d, J=7.2 Hz, 1H), 7.18 (d, J=8.2 Hz, 1H), 7.15 (d, J=7.4 Hz, 2H), 7.10 (t, J=7.5 Hz, 1H), 5.32 (s, 2H), 4.55 (t, J=5.9 Hz, 2H), 4.41 (s, 2H), 3.63 (t, J=5.9 Hz, 2H), 2.14 (s, 3H).

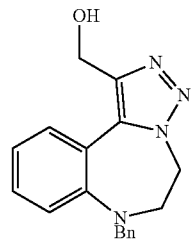 [SMILES: OCc1nnn2c1-c1ccccc1N(Cc1ccccc1)CC2]

Step 6: (7-benzyl-6,7-dihydro-5H-benzo[f][1,2,3]triazolo[1,5-d][1,4]diazepin-1-yl)methanol To a magnetically stirred solution of (7-benzyl-6,7-dihydro-5H-benzo[f][1,2,3]triazolo[1,5-d][1,4]diazepin-1-yl) methyl acetate (560 mg, 1.62 mmol) in methanol:THF (1:4, 5 mL) was added lithium hydroxide monohydrate (326 mg, 8.17 mmol). The mixture was stirred at room temperature for 2 h then the solvent was removed under reduced pressure and the residue was partitioned between EtOAc (10 mL) and water (5 mL). The aqueous phase was separated and extracted with EtOAc (3×15 mL) and the combined organic fractions were dried with MgSO₄, filtered and concentrated under reduced pressure to give (7-benzyl-6,7-dihydro-5H-benzo[f][1,2,3]triazolo[1,5-d][1,4]diazepin-1-yl)methanol (440 mg, 88%) as a white solid.

LCMS (Method A) 5.06 min
m/z [MH]⁺=306.9

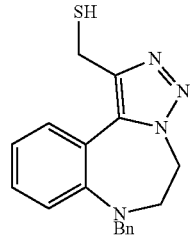 [SMILES: SCc1nnn2c1-c1ccccc1N(Cc1ccccc1)CC2]

Step 7: (7-benzyl-6,7-dihydro-5H-benzo[f][1,2,3]triazolo[1,5-d][1,4]diazepin-1-yl)methanethiol To a magnetically stirred solution of (7-benzyl-6,7-dihydro-5H-benzo[f][1,2,3]triazolo[1,5-d][1,4]diazepin-1-yl)methanol (50 mg, 0.16 mmol) in toluene (2 mL) was added Lawesson's reagent (40 mg, 0.10 mmol). The mixture was stirred under reflux for 24 h then cooled and concentrated onto SiO₂ and the resulting powder was subjected to flash chromatography (gradient elution, 0:1 to 1:0, v/v, EtOAc/cyclohexane) to (7-benzyl-6,7-dihydro-5H-benzo[f][1,2,3]triazolo[1,5-d][1,4]diazepin-1-yl)methanethiol (28 mg, 58%) as a colourless solid.

LCMS (Method B) 6.43 min
m/z [MH]⁺=323.4

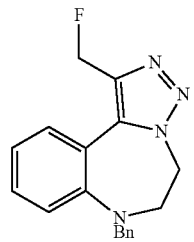 [SMILES: FCc1nnn2c1-c1ccccc1N(Cc1ccccc1)CC2]

Step 8: 7-benzyl-1-(fluoromethyl)-6,7-dihydro-5H-benzo[f][1,2,3]triazolo[1,5-d][1,4]diazepine To a magnetically stirred solution (7-benzyl-6,7-dihydro-5H-benzo[f][1,2,3]triazolo[1,5-d][1,4]diazepin-1-yl)methanol (220 mg, 0.72 mmol) in DCM (5 mL) at 0° C. under a nitrogen atmosphere was added, dropwise, deoxo-fluor (331 μL, 1.80 mmol). The mixture was warmed to room temperature and stirred for 16 h then quenched with NaHCO₃ (5 mL of a saturated aqueous solution). The aqueous phase was extracted with DCM (3×5 mL) and the combined organic fractions were dried with MgSO₄, filtered and concentrated under reduced pressure. The crude material was purified by flash chromatography (gradient elution, 0:1 to 1:1, v/v, EtOAc/cyclohexane) to give 7-benzyl-1-(fluoromethyl)-6,7-dihydro-5H-benzo[f][1,2,3]triazolo[1,5-d][1,4]diazepine (56 mg, 25%) as a colourless solid.

LCMS (Method B) 6.43 min
m/z [MH]⁺=309.3

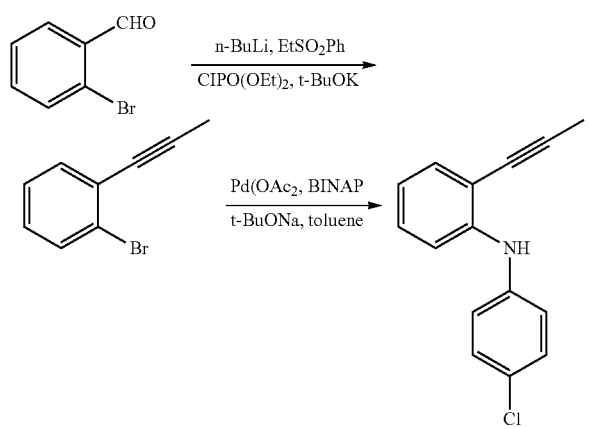

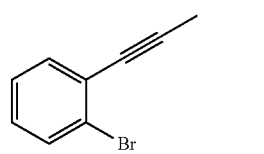

Step 1: 1-bromo-2-(prop-1-yn-1-yl)benzene

To a THF (20 mL) solution of EtSO₂Ph (1.1 g, 6.5 mmol) was added n-BuLi (1.3M, 5.0 mL, 6.5 mmol) at −78° C. The mixture was stirred for 30 min under nitrogen atmosphere. Another THF solution (5 mL) of 2-bromobenzaldehyde (1.0 g, 5.4 mmol) was added at −78° C., the mixture was stirred for 30 min. ClPO(OEt)₂ (1.2 g, 6.5 mmol) was added at −78° C., and the mixture was stirred for 3 h. t-BuOK (3.0 g, 27 mmol) was added at −78° C., and the mixture was stirred at 35° C. overnight. The solvent was removed. Water and ethyl acetate were added. The organic layer was separated and the aqueous layer was extracted twice. The organic layers were combined and washed with brine, dried and concentrated to give a residue which was purified by column chromatography (eluent:petroleum ether) to give 1-bromo-2-(prop-1-yn-1-yl)benzene (600 mg, 60%) as a yellow oil.

LCMS (Method B): 2.86 min m/z [MNa]⁺=217.1; ¹H NMR (400 MHz, CDCl₃)

¹H NMR δ ppm 2.14 (s, 3 H) 7.12 (td, J=8.0 Hz, 1.6 Hz 1 H) 7.25 (td, J=7.6 Hz, 1.2 Hz 1 H) 7.45 (dd, J=7.6 Hz, 1.6 Hz 1 H) 7.58 (d, J=7.2 Hz 1 H).

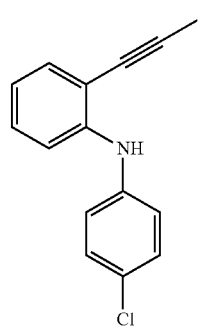 [SMILES: CC#Cc1ccccc1Nc1ccc(Cl)cc1]

Step 2: N-(4-chlorophenyl)-2-(prop-1-yn-1-yl)aniline

To a solution of Pd(OAc)₂ (18 mg, 0.082 mmol) and rac-BINAP (62 mg, 0.1 mmol), t-BuONa (148 mg, 1.54 mmol) in toluene (20 mL) were added 1-bromo-2-(prop-1-yn-1-yl)benzene (200 mg, 1.03 mmol) and 4-chloroaniline (130 mg, 1.03 mmol). The resulting mixture was stirred at 110° C. over 48 h. The mixture was diluted with ethyl acetate (50 mL), washed with saturated Na₂CO₃ solution (50 mL), dried and concentrated under reduced pressure to give a residue which was purified by column chromatography (eluent:petroleum ether/ethyl acetate=100:1) to give N-(4-chlorophenyl)-2-(prop-1-yn-1-yl)aniline (140 mg, 58%) as a yellow solid.

LCMS (Method B): 3.54 min m/z [MH]⁺=242.1

¹H NMR (400 MHz, CDCl₃) δ ppm 2.32 (s, 3 H) 6.43 (s, 1 H) 7.11 (m, 3 H) 7.31 (dd, J=6.4 Hz, 2.0 Hz 2 H) 7.53 (dd, J=6.4 Hz, 2.0 Hz 2 H) 7.59 (m, 1 H).

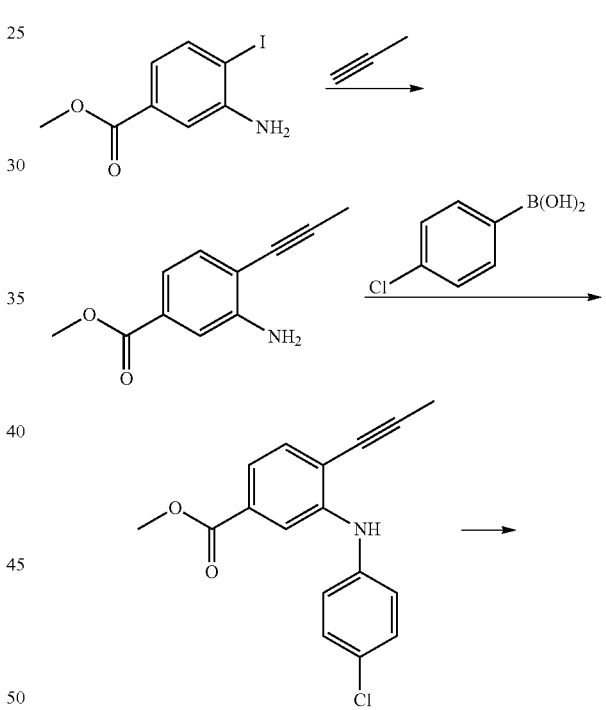

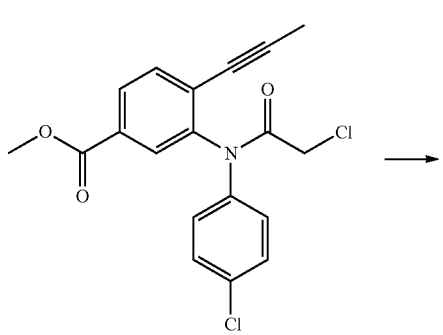

-continued

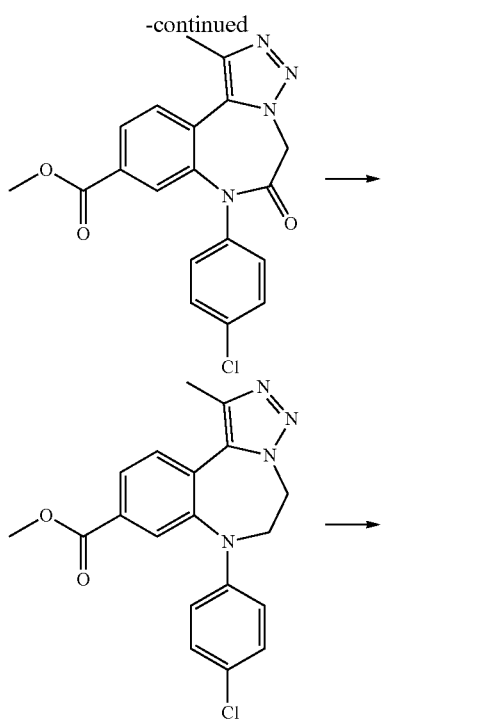

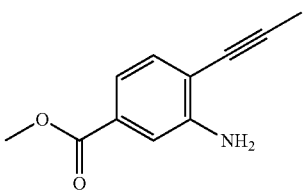

Step 1: methyl 3-amino-4-prop-1-ynyl-benzoate

Into a 2-necked flask were introduced methyl 3-amino-4-iodo-benzoate (5000 mg, 18.05 mmol), [(C$_6$H$_5$)$_3$P]$_2$PdCl$_2$ (316.68 mg, 0.45 mmol), copper iodide (1718.48 mg, 9.02 mmol), dry Et$_3$N (50 mL), and dry DMF (30 mL). The reaction mixture was cooled to −78° C., and condensed propyne (1.00 mL, 1.3 equiv.), measured by condensing the gas in a precooled (−78° C.) graduated cylinder with 3 mL of DMF, was cannulated into the reaction mixture. The reaction mixture was stirred at room temperature for 13 h. Then the mixture was worked up by evaporating the solvent, adding ethyl acetate and water, and extracting with ethyl acetate (2 times). The organic phases were washed with brine, dried with MgSO$_4$ and concentrated under reduced pressure. The crude oil was purified by Combi Flash (Cyclohexanes/EtOAc: 100/0 to 80/20) to afford 2210 mg (64.7%) of methyl 3-amino-4-prop-1-ynyl-benzoate as a yellow solid.

LCMS (Method A): 5.85 min
m/z [MH]$^+$=190.3

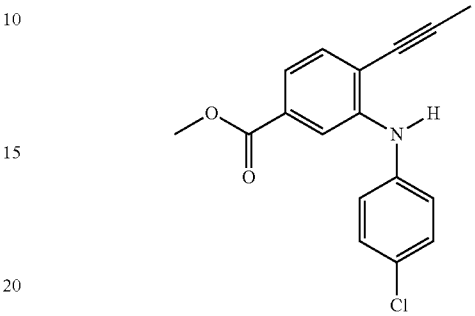

Step 2: methyl 3-(4-chloroanilino)-4-prop-1-ynyl-benzoate

Methyl 3-amino-4-prop-1-ynyl-benzoate (1150 mg, 6.08 mmol) was dissolved in dichloromethane at RT. (4-Chlorophenyl)boronic acid (1900 mg, 12.16 mmol), pyridine (0.98 ml, 12.16 mmol) and diacetoxycopper (2208 mg, 12.16 mmol) were added and the reaction mixture was stirred at RT under O$_2$ atmosphere (balloon) for 16 h. The reaction mixture was partitioned between aqueous citric acid/dichloromethane. The organic phase was washed with brine, dried with MgSO$_4$ and concentrated under reduced pressure. The crude oil was dry loaded on Combi Flash (Cyclohexane/EtOAc: 100/0 to 70/30 to afford 1350 mg (74.1%) of methyl 3-(4-chloroanilino)-4-prop-1-ynyl-benzoate as a white solid.

LCMS (Method B): 7.48 min
$^1$H NMR (600 MHz, chloroform-d): δ ppm 2.15 (s, 3H), 3.85 (s, 3H), 7.12 (d, J=8.8 Hz, 2H), 7.37 (d, J=8.0 Hz, 1H), 7.43 (dd, J=8.0 Hz and 1.5 Hz, 1H), 7.76 (d, J=1.5 Hz, 1H).
m/z [MH]$^+$=300.2

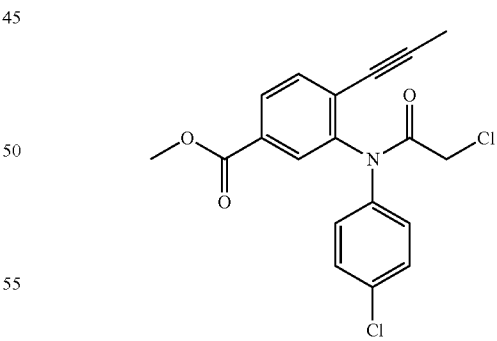

Step 3: methyl 3-(4-chloro-N-(2-chloroacetyl)anilino)-4-prop-1-ynyl-benzoate

Methyl 3-(4-chloroanilino)-4-prop-1-ynyl-benzoate (910 mg, 3.04 mmol) was dissolved in toluene (15 mL) at RT and the solution was cooled to 0° C. 2-Chloroacetyl chloride (0.36 ml, 4.55 mmol) was added dropwise and the reaction mixture was heated at 80° C. for 16 h, cooled to RT and partitioned between H₂O and EtOAc. Organics were washed with brine, dried (MgSO₄) and concentrated under reduced pressure. The crude oil was purified by Combi Flash (Cyclohexane/EtOAc: 95/5 to 60/40) to afford 880 mg (77%) of methyl 3-(4-chloro-N-(2-chloroacetyl)anilino)-4-prop-1-ynyl-benzoate as a white solid.

LCMS (Method A): 6.96 min m/z [MH]⁺=376.2-378.2.

¹H NMR (600 MHz, chloroform-d): δ ppm 2.06 (br s, 3H), 3.90 (s, 3H), 3.99-4.06 (m, 2H), 5.56 (d, J=14.1 Hz, 1H), 7.30 (br m, 2H), 7.55 (br m, 2H), 7.91 (m, 1H), 7.95 (m, 1H), 8.0 (m, 1H).

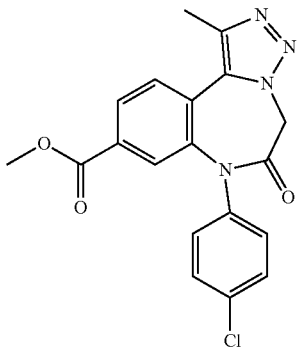 [SMILES: COC(=O)c1ccc2c(c1)N(c1ccc(Cl)cc1)C(=O)Cn1nnc(C)c1-2]

Step 4: methyl 7-(4-chlorophenyl)-1-methyl-5,6,7a,11a-tetrahydrotriazolo[1,5-d][1,4]benzodiazepine-9-carboxylate Methyl 3-(4-chloro-N-(2-chloroacetyl)anilino)-4-prop-1-ynyl-benzoate (200 mg, 0.53 mmol) was dissolved in DMF (5 mL) at RT under N₂. NaN₃ (104 mg, 1.59 mmol) was added and the reaction mixture was stirred at RT for 16 h. The mixture was partitioned between EtOAc and H₂O. The organics were washed with brine, dried (MgSO₄) and concentrated under reduced pressure. The crude oil was redissolved in DMF (2 mL) and the reaction mixture was heated at 150° C. for 4 h, cooled to RT, and partitioned between dichloromethane and H₂O. The organics were washed with brine, dried (MgSO₄) and concentrated. The crude oil was purified by Combi Flash (dichloromethane/MeOH 100/0 to 90/10) to afford 163 mg (80.1%) of methyl 7-(4-chlorophenyl)-1-methyl-5,6,7a,11a-tetrahydrotriazolo[1,5-d][1,4]benzodiazepine-9-carboxylate as a light yellow solid.

LCMS (Method A): 5.94 min

¹H NMR (600 MHz, chloroform-d): δ ppm 2.64 (s, 3H), 3.88 (s, 3H), 4.71 (d, J=14.1 Hz, 1H), 5.56 (d, J=14.1 Hz, 1H), 7.06 (d, J=8.9 Hz, 2H), 7.37 (d, J=8.9 Hz, 2H), 7.65 (s, 1H), 7.67 (m, 2H).

m/z [MH]⁺=387.1.

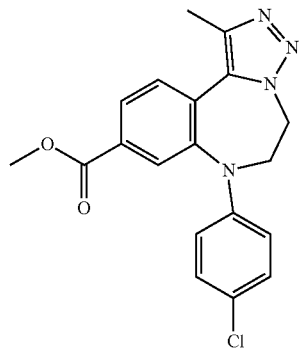 [SMILES: COC(=O)c1ccc2c(c1)N(c1ccc(Cl)cc1)CCn1nnc(C)c1-2]

Step 5: methyl 7-(4-chlorophenyl)-1-methyl-5,6-dihydrotriazolo[1,5-d][1,4]benzo diazepine-9-carboxylate Methyl 7-(4-chlorophenyl)-1-methyl-5,6,7a,11a-tetrahydrotriazolo[1,5-d][1,4]benzo diazepine-9-carboxylate (160 mg, 0.42 mmol) was dissolved/suspended in dry THF (5 mL), cooled to 0° C. and 1M BH₃ THF (1.25 ml) was added. The mixture was stirred at RT then 50° C. for 4 h. MeOH (10 mL) was carefully added and the solvents were evaporated. The crude solid was dissolved in dichloromethane (5 mL—heating for 20 min at 50° C.), then THF (5 mL) was added to form a clear solution. BH3.THF (3 eq) was added and the solution was heated at 60° C. for 16 h. MeOH (5 mL) added carefully and the solvents were evaporated. The crude oil was redissolved in MeOH (10 mL), refluxed for 30 min and the solvent was removed. This was repeated 2 times. The crude solid was purified by Combi Flash (Cyclohex/EtOAc: 80/20 to 20/80) to afford 90 mg (58.4%) of methyl 7-(4-chlorophenyl)-1-methyl-5,6-dihydrotriazolo[1,5-d][1,4]benzodiazepine-9-carboxylate as a yellow solid.

LCMS (Method A): 5.95 min m/z [MH]⁺=369.2.

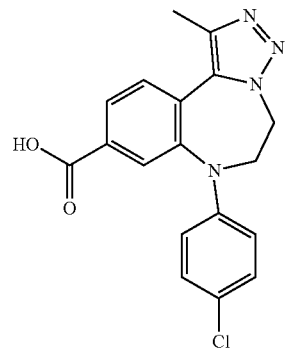 [SMILES: Cc1nnn2c1-c1ccc(C(=O)O)cc1N(c1ccc(Cl)cc1)CC2]

Step 6: 7-(4-chlorophenyl)-1-methyl-5,6-dihydrotriazolo[1,5-d][1,4]benzodiazepine-9-carboxylic acid Methyl-7-(4-chlorophenyl)-1-methyl-5,6-dihydrotriazolo[1,5-d][1,4]benzodiazepine-9-carboxylate (83 mg, 0.23 mmol) was dissolved in a mixture THF/MeOH (2 mL, 1/1). NaOH (2M) was added and the reaction mixture was stirred at 40° C. for 2 h. The solvents were removed under reduced pressure and the crude oil was partitioned between EtOAc/HCl (1M). The organics were separated, washed with brine, dried (MgSO$_4$) and concentrated under reduced pressure. The crude oil was purified by Combi Flash (dichloromethane/MeOH 100/0 to 90/10) to afford 72 mg (90.2%) of 7-(4-chlorophenyl)-1-methyl-5,6-dihydrotriazolo[1,5-d][1,4]benzodiazepine-9-carboxylic acid as a light yellow solid.

LCMS (Method A): 5.53 min m/z [MH]$^+$=355.2.

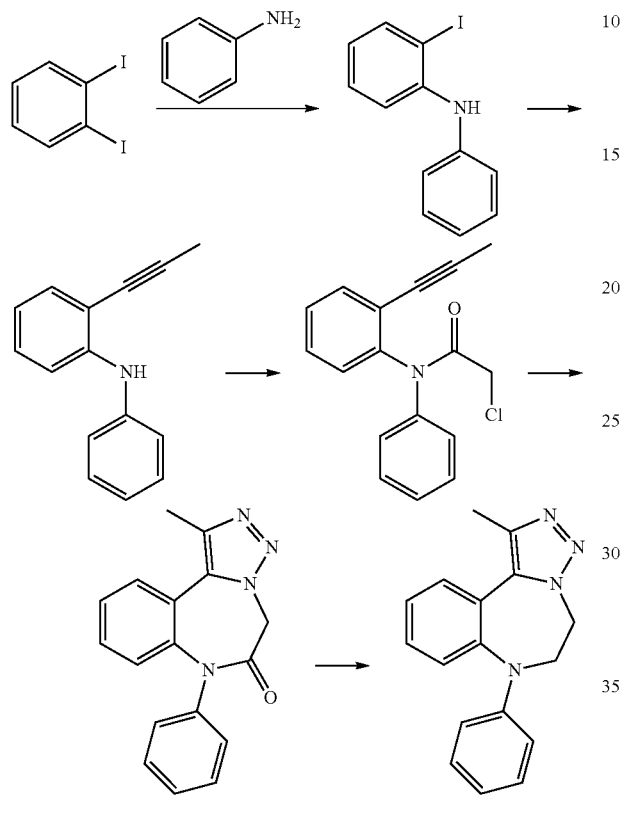

Step 1: 2-iodo-N-phenylbenzenamine

To a mixture of 1,2-diiodobenzene (5.0 g, 15.16 mmol, 1.0 eq), aniline (1.4 g, 15.16 mmol, 1.0 eq) in toluene (100 mL) were added Cs$_2$CO$_3$ (6.0 g, 18.50 mmol, 1.22 eq), Pd(dba)$_2$ (106.4 mg, 0.15 mmol, 0.01 eq) and Xantphos (440 mg, 0.76 mmol, 0.05 eq).

The mixture was stirred at 110° C. under N$_2$ atmosphere overnight. The mixture was cooled to room temperature, diluted with ethyl acetate (100 mL), washed with water (3×100 mL), dried (Na$_2$SO$_4$), concentrated, purified by column chromatography on silica gel (petroleum ether) to give 2-iodo-N-phenylbenzenamine (1.2 g, 27%) as a brown oil.

LCMS (Method B): 3.19 min m/z [MH]$^+$=296.0.

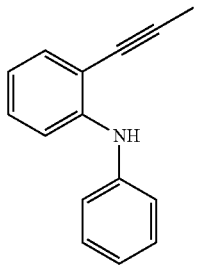 [SMILES: CC#Cc1ccccc1Nc1ccccc1]

Step 2: N-phenyl-2-(prop-1-ynyl)benzenamine

To a mixture of 2-iodo-N-phenylbenzenamine (1.2 g, 4.07 mmol, 1.0 eq), trimethyl(prop-1-ynyl)silane (1.83 g, 16.28 mmol, 4.0 eq) in toluene (15 mL) and THF (5 mL) were added TBAF.3H$_2$O (2.6 g, 8.14 mmol, 2.0 eq), TEA (1.2 g, 12.21 mmol, 3.0 eq), CuI (233 mg, 1.22 mmol, 0.3 eq), and Pd(PPh$_3$)$_4$ (235 mg, 0.20 mmol, 0.05 eq). The mixture was stirred at 70° C. under N$_2$ atmosphere overnight. The mixture was cooled to room temperature, diluted with ethyl acetate (100 mL), washed with water (3×100 mL), dried (Na$_2$SO$_4$), concentrated under reduced pressure, purified by column chromatography on silica gel (100% petroleum ether) to give N-phenyl-2-(prop-1-ynyl)benzenamine (700 mg, 84%) as yellow oil.

LCMS (Method B): 3.24 min m/z [MH]$^+$=208.1.

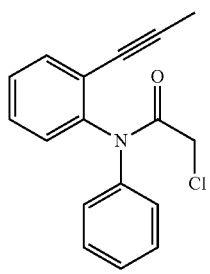 [SMILES: CC#Cc1ccccc1N(C(=O)CCl)c1ccccc1]

Step 3: 2-chloro-N-phenyl-N-(2-(prop-1-ynyl)phenyl)acetamide

To a solution of N-phenyl-2-(prop-1-ynyl)benzenamine (700 mg, 3.40 mmol, 1.0 eq) in dichloromethane were added K$_2$CO$_3$ (1.4 g, 10.2 mmol, 3.0 eq) and 2-chloroacetyl chloride (768 mg, 6.8 mmol, 2.0 eq). The mixture was stirred at 45° C. under N$_2$ atmosphere overnight. The mixture was cooled to room temperature, diluted with dichloromethane (100 mL), washed with water (3×100 mL), dried (Na$_2$SO$_4$), concentrated under reduced pressure and purified by column chromatography on silica gel (petroleum ether/ethyl acetate=100/0~10:1) to give 2-chloro-N-phenyl-N-(2-(prop-1-ynyl)phenyl) acetamide (600 mg, 64%) as yellow oil.

LCMS (Method B): 2.61 min m/z [MH]$^+$=284.1

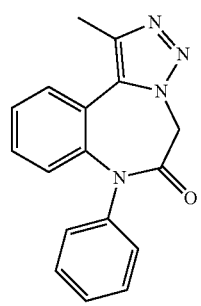 [SMILES: Cc1nnn2c1-c1ccccc1N(c1ccccc1)C(=O)C2]

Step 4:1-methyl-7-phenyl-5H-benzo[f][1,2,3]tri-azolo[1,5-d][1,4]diazepin-6(7H)-one To a solution of 2-chloro-N-phenyl-N-(2-(prop-1-ynyl)phenyl)acetamide (600 mg, 2.10 mmol, 1.0 eq) in DMF (10 mL) was added sodium azide (412 mg, 6.3 mmol, 3.0 eq). The mixture was stirred at 100° C. under $N_2$ atmosphere overnight, and then heated to 140° C. for 2 h. The mixture was cooled to room temperature, diluted with ethyl acetate (100 mL), washed with water (3×100 mL), dried ($Na_2SO_4$), concentrated under reduced pressure, and purified by preparative HPLC to give 1-methyl-7-phenyl-5H-benzo[f][1,2,3]triazolo[1,5-d][1,4]diazepin-6(7H)-one (80 mg, 13%) as white solid.
LCMS (Method B): 2.25 min
m/z $[MH]^+$=291.1.

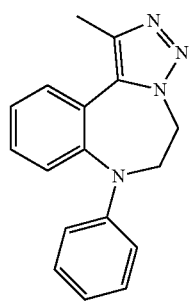 [SMILES: Cc1nnn2c1-c1ccccc1N(c1ccccc1)CC2]

Step 5: 1-methyl-7-phenyl-6,7-dihydro-5H-benzo[f][1,2,3]triazolo[1,5-d][1,4]diazepine To a solution of 1-methyl-7-phenyl-5H-benzo[f][1,2,3]triazolo[1,5-d][1,4]diazepin-6(7H)-one (20.0 mg, 0.07 mmol, 1.0 eq) in THF (2 mL) was added a solution of borane in THF (1M, 0.7 mL, 10.0 eq). The mixture was stirred at 70° C. under $N_2$ atmosphere for 2 h. The mixture was cooled to room temperature, diluted with ethyl acetate (100 mL), washed with water (100 mL), dried ($Na_2SO_4$), concentrated under reduced pressure and purified by preparative TLC to give 1-methyl-7-phenyl-6,7-dihydro-5H-benzo[f][1,2,3]triazolo[1,5-d][1,4]diazepine (16 mg, 88%) as white solid.
LCMS (Method B): 2.64 min
m/z $[MH]^+$=277.2

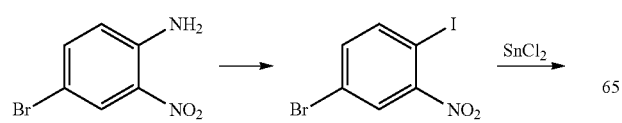

-continued

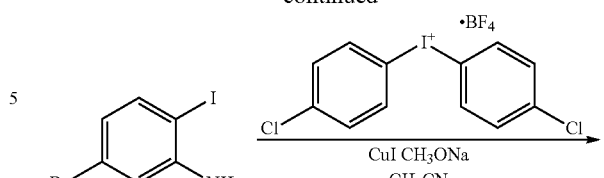

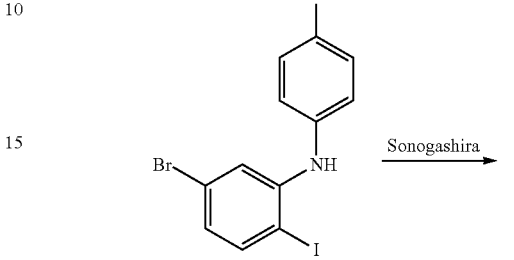

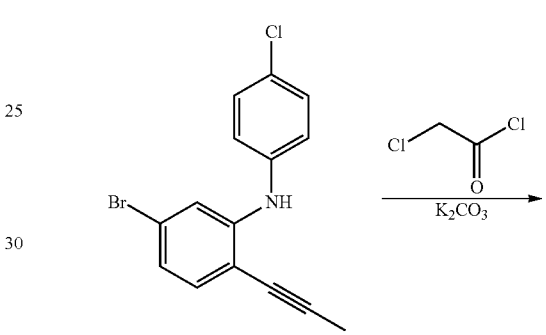

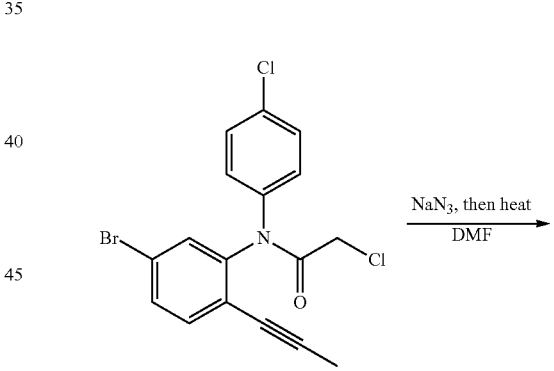

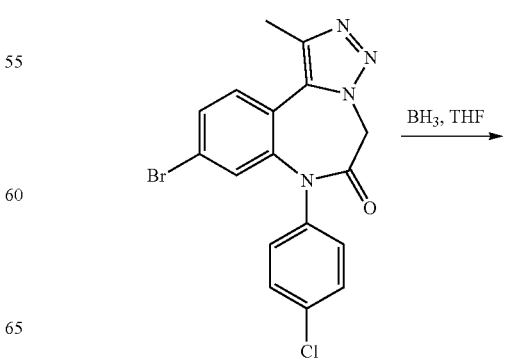

-continued

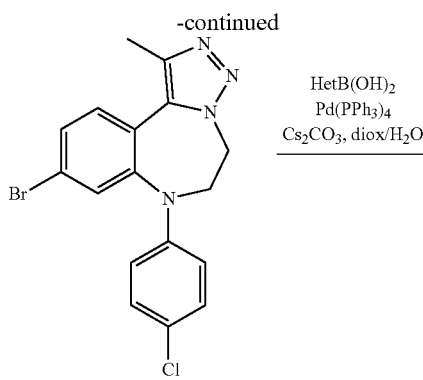

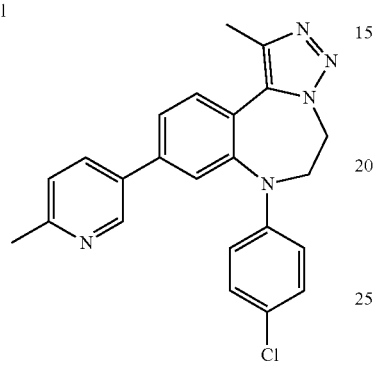

9-Bromo-7-(4-chlorophenyl)-1-methyl-6,7-dihydro-5H-benzo[f][1,2,3]triazolo[1,5-d][1,4]diazepine

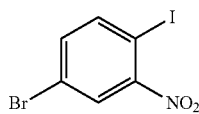

Step 1: 4-bromo-1-iodo-2-nitrobenzene

To a solution of $BF_3/Et_2O$ (125 mL, 0.97 mol) was added a solution of 4-bromo-2-nitroaniline (50 g, 0.23 mol) in THF (750 mL), followed by addition of tert-butylnitrite (102 mL, 0.86 mmol) in THF (750 mL) at −50° C. The reaction was then allowed to warm to −5° C. Diethyl ether (1.5 L) was added and the reaction mixture was stirred at −5° C. for 15 min until a pale yellow solid precipitated. The yellow solid was collected and dissolved in acetonitrile (750 mL), and then potassium iodide (55 g, 0.33 mmol), iodine (42 g, 0.16 mmol) were added into the above mixture. The resulting mixture was stirred at room temperature for 15 min. The mixture was partitioned between aqueous sodium sulfite solution (saturated, 1 L) and dichloromethane (1 L). The organic layer was separated, dried over sodium sulfate, and concentrated under reduced pressure to give 4-bromo-1-iodo-2-nitrobenzene (66 g, 88%) as a crude yellow solid.

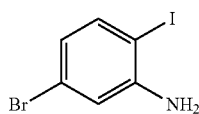

Step 2: 5-bromo-2-iodoaniline

To a solution of 4-bromo-1-iodo-2-nitrobenzene (66 g, 0.2 mol) in MeOH (700 mL) was added stannous chloride (226 g, 1 mol) at 0° C. The resultant mixture was heated to reflux (80° C.) for 4 h. The solvent was removed under reduced pressure, and then the residue was diluted with ethyl acetate (1 L), washed with $H_2O$ (1 L), dried over sodium sulfate, concentrated to give a residue which was purified by column chromatography (eluent:petroleum ether:ethyl acetate=20:1) to give 5-bromo-2-iodoaniline (39 g, 65%) as a white solid.
LCMS (Method B): 2.27 min
m/z [MH]$^+$=298.1; 300.1.

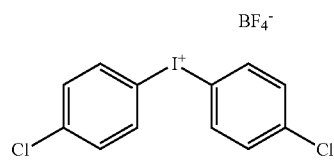 [SMILES: "BF4-" ; Clc1ccc([I+]c2ccc(Cl)cc2)cc1]

Step 3: bis(4-chlorophenyl)iodonium tetrafluoroborate m-CPBA (2.06 g, 12 mmol) was dissolved in dichloromethane (50 mL). To this solution was added 1-chloro-4-iodobenzene (2.57 g, 10.8 mmol), followed by addition of $BF_3.OEt_2$ (3.4 mL, 27.2 mmol) at room temperature. The resultant mixture was stirred for 30 min at room temperature under nitrogen atmosphere, and then cooled to 0° C. (4-Chlorophenyl)boronic acid (1.87 g, 12 mmol) was added. The resulting mixture was allowed to stir for 15 min at RT after which time TLC analysis indicated that the reaction was complete. The solvent was removed under reduced pressure to give a residue which was purified by column chromatography (eluent:dichloromethane:MeOH=20:1) to give bis(4-chlorophenyl)iodonium tetrafluoroborate salt as a white solid (1.10 g, 28.7%).
LCMS (Method B): 1.68 min
m/z [MH]$^+$=348.9; 350.9.

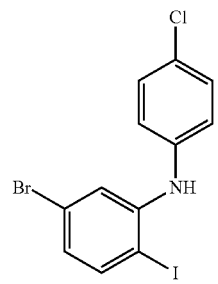 [SMILES: Clc1ccc(Nc2cc(Br)ccc2I)cc1]

Step 4: 5-bromo-N-(4-chlorophenyl)-2-iodoaniline

To a mixture of bis(4-chlorophenyl)iodonium tetrafluoroborate (145 mg, 0.33 mmol), sodium carbonate (71 mg, 0.67 mmol) and copper (I) iodide (6.3 mg, 0.033 mmol) in dichloromethane (5 mL) at room temperature was added 5-bromo-2-iodoaniline (149 mg, 0.5 mmol). The resulting mixture was stirred at room temperature overnight. The mixture was diluted with dichloromethane (10 mL), washed with water (10 mL). The organic layer was separated, dried over sodium sulfate, and concentrated under reduced pressure to give the crude product which was purified by column chromatography (eluent: 100% petroleum ether) to give 5-bromo-N-(4-chlorophenyl)-2-iodoaniline (80 mg, 39%) as a yellow solid.

LCMS (Method B): 2.72 min

[MH]$^+$=408.1; 410.1.

$^1$H NMR (400 MHz, DMSO-d$_6$) δ ppm 6.96 (dd, J=8.4 Hz, 2.0 Hz 1 H) 7.00 (dd, J=6.8 Hz, 2.0 Hz 2 H) 7.22 (d, J=2.2 Hz 1 H) 7.29 (dd, J=6.8 Hz, 2.0 Hz 2 H) 7.70 (s, 1 H) 7.77 (d, J=8.4 Hz 1 H).

m/z [MH]$^+$=408.1; 410.1.

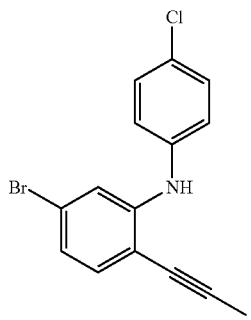 [SMILES: CC#Cc1ccc(Br)cc1Nc1ccc(Cl)cc1]

Step 5: 5-bromo-N-(4-chlorophenyl)-2-(prop-1-yn-1-yl)aniline

A mixture of 5-bromo-N-(4-chlorophenyl)-2-iodoaniline (80 mg, 0.2 mmol), trimethyl(prop-1-yn-1-yl)silane (88 mg, 0.8 mmol), Pd(PPh$_3$)$_4$(12 mg, 0.01 mmol), TBAF.H$_2$O (13 mg, 0.04 mmol), Et$_3$N (6 mg, 0.06 mmol), copper(I) iodide (1 mg, 0.006 mmol) in toluene (4 mL) and THF (2 mL) were stirred at 70° C. overnight under N$_2$. The solvent was removed under reduced pressure to give a residue which was purified by column chromatography (eluent:petroleum ether:ethyl acetate=50:1) to give 5-bromo-N-(4-chlorophenyl)-2-(prop-1-yn-1-yl)aniline as a white solid (20 mg, 31%).

LCMS (Method B): 2.54 min $^1$H NMR (400 MHz, CDCl$_3$) δ ppm 2.15 (s, 3 H) 6.39 (s, 1 H) 6.90 (dd, J=8.2 Hz, 1.9 Hz 1 H) 7.15 (dd, J=6.8 Hz, 2.4 Hz 2 H) 7.20 (d, J=8.0 Hz 1 H) 7.23 (d, J=2.0 Hz 1 H) 7.34 (dd, J=6.8 Hz, 2.4 Hz 2 H).

m/z [MH]$^+$=320.2; 322.2.

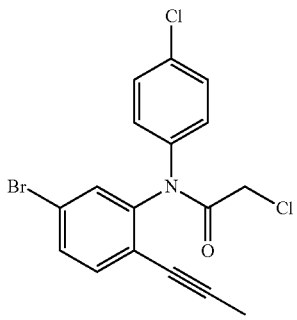 [SMILES: CC#Cc1ccc(Br)cc1N(C(=O)CCl)c1ccc(Cl)cc1]

Step 6: N-(5-bromo-2-(prop-1-yn-1-yl)phenyl)-2-chloro-N-(4-chlorophenyl) acetamide To a solution of 5-bromo-N-(4-chlorophenyl)-2-(prop-1-yn-1-yl)aniline (600 mg, 1.89 mmol) in toluene (15 mL) were added 2-chloroacetyl chloride (318 mg, 2.82 mmol) and potassium carbonate (774 mg, 5.64 mmol) at 0° C. The resulting mixture was heated to 80° C. for 4 h, and then was quenched with water. The organic layer was separated, dried over sodium sulfate, and concentrated under reduced pressure. The crude product was purified by column chromatography (eluent:petroleum ether:ethyl acetate=50:1) to give N-(5-bromo-2-(prop-1-yn-1-yl)phenyl)-2-chloro-N-(4-chlorophenyl) acetamide (550 mg, 73% yield) as a grey oil.

LCMS (Method B): 3.11 min m/z [MH]$^+$=396.1; 398.1; 400.1.

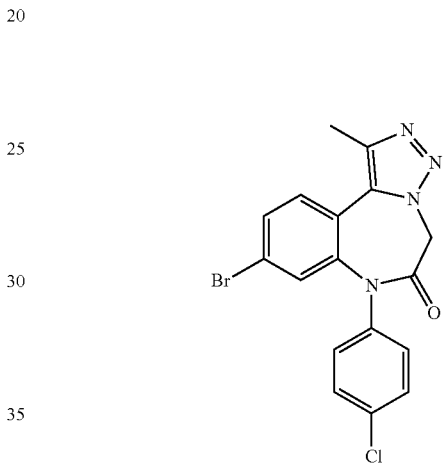

Step 7: 9-bromo-7-(4-chlorophenyl)-1-methyl-5H-benzo[f][1,2,3]triazolo[1,5-d][1,4]diazepin-6(7H)-one N-(5-bromo-2-(prop-1-yn-1-yl)phenyl)-2-chloro-N-(4-chlorophenyl)acetamide (650 mg, 1.64 mmol) and sodium azide (319 mg, 4.91 mmol) were dissolved in DMF (12 mL) at room temperature. The mixture was allowed to stir for 4 h. The mixture was diluted with ethyl acetate (30 mL), washed with water (10 mL), and concentrated under reduced pressure. The crude intermediate (250 mg, 0.62 mmol) was redissolved in DMF (2.5 mL) and the mixture was heated to 150° C. for 5 h. and then the mixture was allowed to cool to RT, diluted with ethyl acetate (10 mL) and washed with water (10 mL). The organic layer was dried over sodium sulfate, and concentrated under reduced pressure. The crude product was purified by column chromatography (eluent: petroleum ether: ethyl acetate=2:1) to give 9-bromo-7-(4-chlorophenyl)-1-methyl-5H-benzo[f][1,2,3]triazolo[1,5-d][1,4]diazepin-6(7H)-one (250 mg, 39%) as a grey oil.

LCMS (Method B): 2.40 min m/z [MH]$^+$=403.1; 405.1.

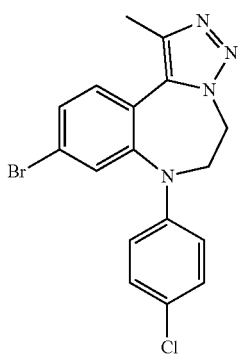 [SMILES: Cc1nnn2c1-c1ccc(Br)cc1N(c1ccc(Cl)cc1)CC2]

Step 8: 9-bromo-7-(4-chlorophenyl)-1-methyl-6,7-dihydro-5H-benzo[f][1,2,3]triazolo[1,5-d][1,4]diazepine To a solution of 9-bromo-7-(4-chlorophenyl)-1-methyl-5H-benzo[f][1,2,3]triazolo[1,5-d][1,4]diazepin-6(7H)-one (1.4 g, 3.50 mmol) in THF (150 mL) was added a solution of BH$_3$ in THF (1M, 45 mL, 45 mmol). The reaction mixture was allowed to stir at RT for 4 h, and then was quenched by slow addition of methanol. The solvent was removed to give a residue which was diluted with ethyl acetate (100 mL), washed with water (50 mL). The organic layer was dried over sodium sulfate, and concentrated to give the crude product which was rinsed with petroleum ether (20 mL) to give 9-bromo-7-(4-chlorophenyl)-1-methyl-6,7-dihydro-5H-benzo[f][1,2,3]triazolo[1,5-d][1,4]diazepine (650 mg, 48% yield) as a yellow solid.

LCMS (Method B): 3.31 min.
m/z [MH]$^+$=389.1; 391.1.

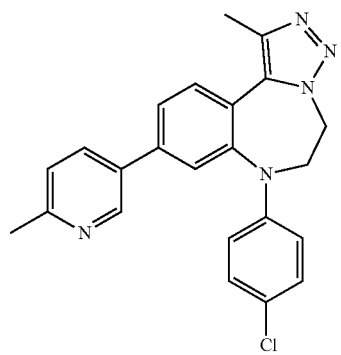 [SMILES: Cc1ccc(-c2ccc3c(c2)N(c2ccc(Cl)cc2)CCn2nnc(C)c2-3)cn1]

7-(4-Chlorophenyl)-1-methyl-9-(6-methylpyridin-3-yl)-6,7-dihydro-5H-benzo[f][1,2,3]triazolo[1,5-d][1,4]diazepine A mixture of 9-bromo-7-(4-chlorophenyl)-1-methyl-6,7-dihydro-5H-benzo[f][1,2,3]triazolo[1,5-d][1,4]diazepine (80 mg, 0.2 mmol), (6-methylpyridin-3-yl)boronic acid (28 mg, 0.2 mmol), Pd(PPh$_3$)$_4$(24 mg, 0.02 mmol), K$_3$PO$_4$ (168 mg, 0.63 mmol) in DME (16 mL) and H$_2$O (0.2 mL) were stirred at 120° C. for 1 h under N$_2$. The solvent was removed under reduced pressure to give a residue which was purified by preparative TLC (eluent:petroleum ether:ethyl acetate=1:1) to give 7-(4-chlorophenyl)-1-methyl-9-(6-methylpyridin-3-yl)-6,7-dihydro-5H-benzo[f][1,2,3]triazolo[1,5-d][1,4]diazepine as a white solid (8 mg, 10%).

LCMS (Method B): 3.07 min
m/z [MH]$^+$=402.1, 404.1.

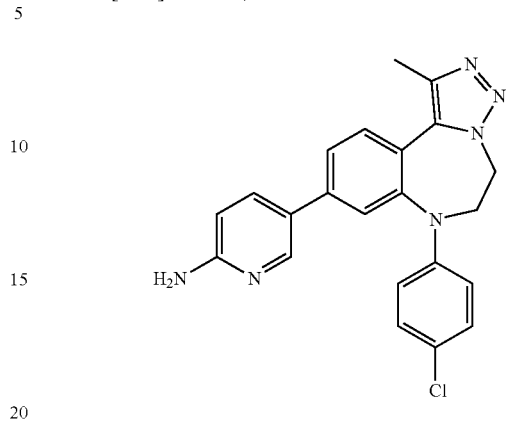

5-(7-(4-Chlorophenyl)-1-methyl-6,7-dihydro-5H-benzo[f][1,2,3]triazolo[1,5-d][1,4]diazepin-9-yl)pyridin-2-amine A mixture of 9-bromo-7-(4-chlorophenyl)-1-methyl-6,7-dihydro-5H-benzo[f][1,2,3]triazolo[1,5-d][1,4]diazepine (80 mg, 0.2 mmol), 5-(4,4,5,5-tetramethyl-1,3,2-dioxaborolan-2-yl)pyridin-2-amine (45 mg, 0.2 mmol), Pd(PPh$_3$)$_4$(24 mg, 0.02 mmol) and K$_3$PO$_4$ (168 mg, 0.63 mmol) in DME (16 mL) and H$_2$O (0.2 mL) was stirred at 120° C. for 1 h under N$_2$. The solvent was removed under reduced pressure to give a residue which was purified by prep HPLC to give 5-(7-(4-chlorophenyl)-1-methyl-6,7-dihydro-5H-benzo[f][1,2,3]triazolo[1,5-d][1,4]diazepin-9-yl)pyridin-2-amine as a white solid (7 mg, 8%).

LCMS (Method B): 2.38 min
m/z [MH]$^+$=403.1.

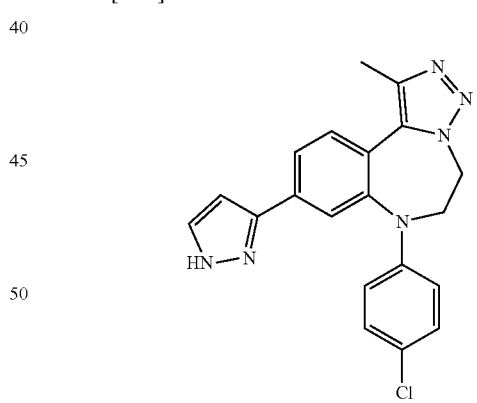

7-(4-Chlorophenyl)-1-methyl-9-(1H-pyrazol-3-yl)-6,7-dihydro-5H-benzo[f][1,2,3]triazolo[1,5-d][1,4]diazepine A mixture of 9-bromo-7-(4-chlorophenyl)-1-methyl-6,7-dihydro-5H-benzo[f][1,2,3]triazolo[1,5-d][1,4]diazepine (400 mg, 1.05 mmol), 3-(4,4,5,5-tetramethyl-1,3,2-dioxaborolan-2-yl)-1H-pyrazole (205 mg, 1.05 mmol), Pd(PPh$_3$)$_4$(125 mg, 0.1 mmol) and K$_3$PO$_4$ (665 mg, 3.15 mmol) in DME (16 mL) and H$_2$O (0.2 mL) was stirred at 120° C. for 1 h under N$_2$. The solvent was removed under reduced pressure to give a residue which was purified by prep HPLC to give 7-(4-chlorophenyl)-1-methyl-9-(1H-pyrazol-3-yl)-6,7-dihydro-5H-benzo[f][1,2,3]triazolo[1,5-d][1,4]diazepine as a white solid (20 mg, 5%).

LCMS (Method B): 2.80 min m/z [MH]$^+$=377.1, 379.1.

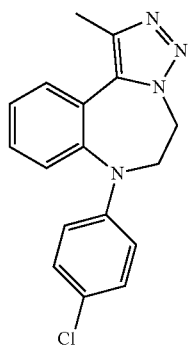 [SMILES: Cc1nnn2c1-c1ccccc1N(c1ccc(Cl)cc1)CC2]

7-(4-chlorophenyl)-1-methyl-6,7-dihydro-5H-benzo[f][1,2,3]triazolo[1,5-d][1,4]diazepine The mixture of 9-bromo-7-(4-chlorophenyl)-1-methyl-6,7-dihydro-5H-benzo[f][1,2,3]triazolo[1,5-d][1,4]diazepine (400 mg, 0.1 mmol), Pd(PPh$_3$)$_4$(125 mg, 0.1 mmol) and K$_3$PO$_4$ (665 mg, 3.2 mmol) in DME (5 mL) and H$_2$O (0.1 mL) were stirred at 120° C. under microwave condition for 1 h under N$_2$. The solution was cooled to RT, filtered and the solvent was removed under reduced pressure to give a residue which was purified by preparative HPLC to give 7-(4-chlorophenyl)-1-methyl-6,7-dihydro-5H-benzo[f][1,2,3]triazolo[1,5-d][1,4]diazepine (20 mg, 5%) as a white solid.

LCMS (Method B): 2.93 min m/z [MH]$^+$=311.1.

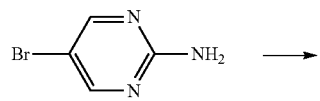

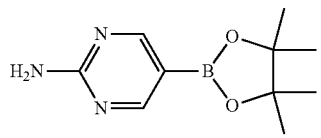

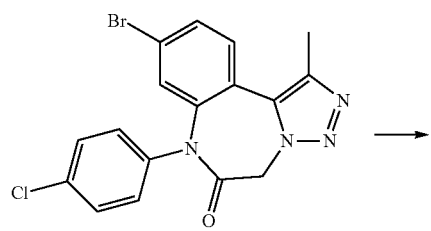

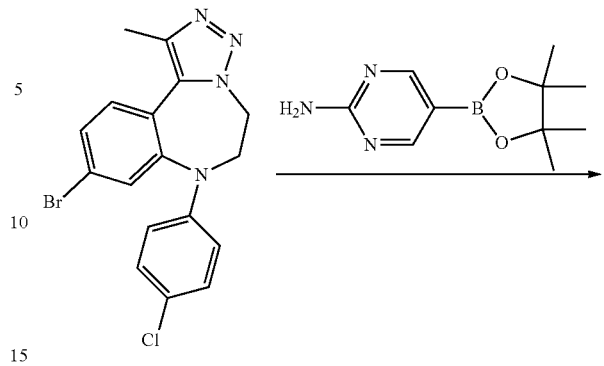

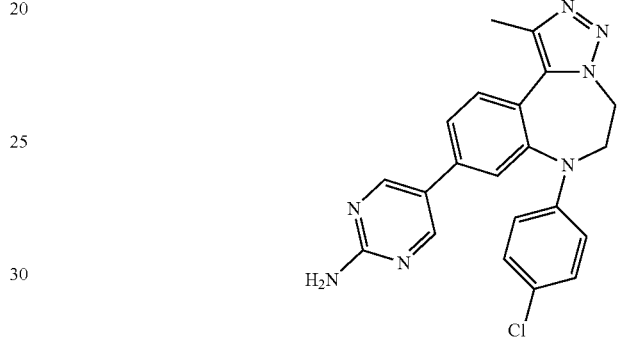

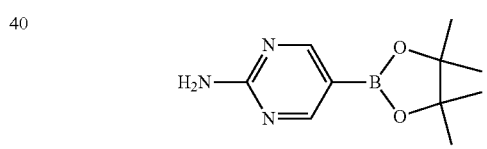

Step 1: 5-(4,4,5,5-tetramethyl-1,3,2-dioxaborolan-2-yl)pyrimidin-2-amine

To a mixture of 5-bromopyrimidin-2-amine (500 mg, 2.9 mmol, 1.0 eq), 4,4,4',4',5,5,5',5'-octamethyl-2,2'-bi(1,3,2-dioxaborolane) (1.47 g, 5.8 mmol, 2.0 eq) in dioxane (20 mL) were added KOAc (865 mg, 8.7 mmol, 0.1 eq) and Pd(dppf)Cl$_2$ (212 mg, 0.29 mmol, 0.1 eq). The mixture was stirred at 115° C. under N$_2$ atmosphere overnight. The mixture was cooled to room temperature, diluted with ethyl acetate (100 mL), washed with water (3×100 mL), dried (Na$_2$SO$_4$), concentrated under reduced pressure and purified by column chromatography on silica gel (petroleum ether to dichloromethane:MeOH=20:1) to give 5-(4,4,5,5-tetramethyl-1,3,2-dioxaborolan-2-yl)pyrimidin-2-amine (300 mg, 75%) as yellow oil.

LCMS (Method B): 0.51 min m/z [MH]$^+$=139.1 (boronic acid).

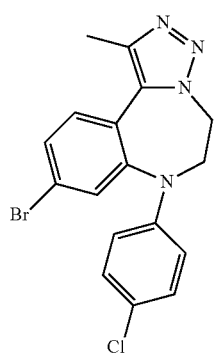 [SMILES: Cc1nnn2c1-c1ccc(Br)cc1N(c1ccc(Cl)cc1)CC2]

Step 2: 9-bromo-7-(4-chlorophenyl)-1-methyl-6,7-dihydro-5H-benzo[f][1,2,3]triazolo[1,5-d][1,4]diazepine To a solution of 9-bromo-7-(4-chlorophenyl)-1-methyl-5H-benzo[f][1,2,3]triazolo[1,5-d][1,4]diazepin-6(7H)-one (200 mg, 0.49 mmol, 1.0 eq) in THF (5 mL) was added a solution of borane in THF (1M, 4.9 mL, 10.0 eq). The mixture was stirred at RT under $N_2$ atmosphere overnight. The mixture was diluted with ethyl acetate (100 mL), washed with water (100 mL), dried ($Na_2SO_4$), concentrated under reduced pressure and purified by column chromatography on silica gel (PE:EA=10:1 to 1:1) to give 9-bromo-7-(4-chlorophenyl)-1-methyl-6,7-dihydro-5H-benzo[f][1,2,3]triazolo[1,5-d][1,4]diazepine (120 mg, 63%) as white solid.

LCMS (Method B): 3.23 min
m/z [MH]$^+$=389.0, 391.0.

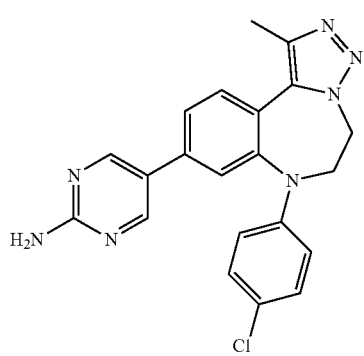 [SMILES: Cc1nnn2c1-c1ccc(-c3cnc(N)nc3)cc1N(c1ccc(Cl)cc1)CC2]

Step 3: 5-(7-(4-chlorophenyl)-1-methyl-6,7-dihydro-5H-benzo[f][1,2,3]triazolo[1,5-d][1,4]diazepin-9-yl)pyrimidin-2-amine To a mixture of 9-bromo-7-(4-chlorophenyl)-1-methyl-6,7-dihydro-5H-benzo[f][1,2,3]triazolo[1,5-d][1,4]diazepine (80 mg, 0.20 mmol, 1.0 eq), 5-(4,4,5,5-tetramethyl-1,3,2-dioxaborolan-2-yl)pyrimidin-2-amine (60 mg, 0.40 mmol, 2.0 eq) in DME (15 mL) and $H_2O$ (5 drops) were added $K_3PO_4·3 H_2O$ (160 mg, 0.6 mmol, 3.0 eq) and Pd(PPh$_3$)$_4$ (25 mg, 0.02 mmol, 0.1 eq). The mixture was stirred at 80° C. under MW irradiation for 1 h. The mixture was cooled to RT, diluted with ethyl acetate (50 mL), washed with water (100 mL), dried ($Na_2SO_4$), concentrated under reduced pressure and purified by column chromatography on silica gel (petroleum ether to dichloromethane: MeOH=20:1) to give 5-(7-(4-chlorophenyl)-1-methyl-6,7-dihydro-5H-benzo[f][1,2,3]triazolo[1,5-d][1,4]diazepin-9-yl)pyrimidin-2-amine (30 mg, 37%).

LCMS (Method B): 2.60 min [MH]$^+$=404.1
m/z [MH]$^+$=404.1

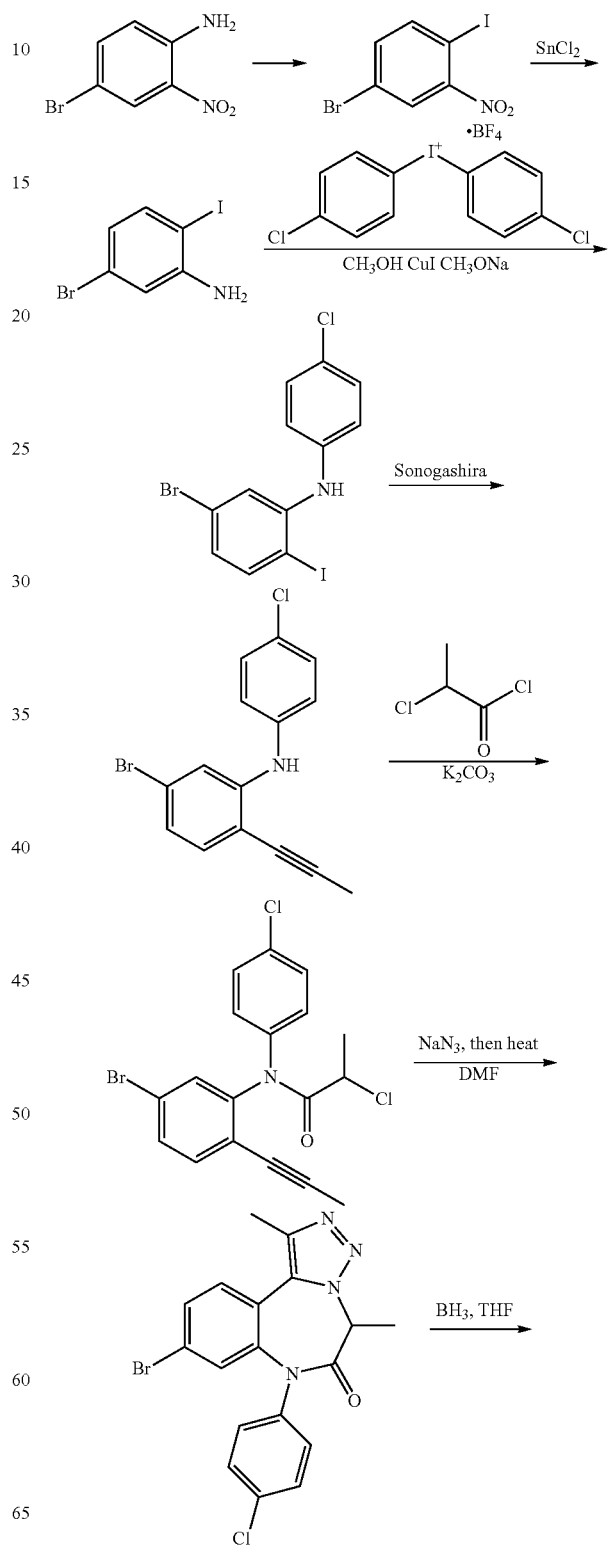

-continued

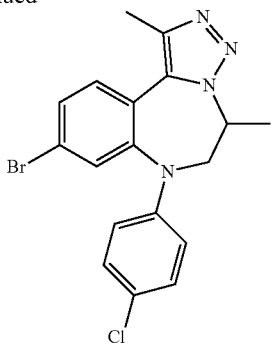

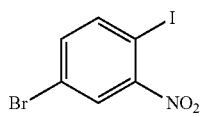 [SMILES: O=[N+]([O-])c1cc(Br)ccc1I]

Step 1: 4-bromo-1-iodo-2-nitrobenzene

To a solution of BF$_3$/Et$_2$O (125 mL, 0.97 mol) was added a solution of 4-bromo-2-nitroaniline (50 g, 0.23 mol) in THF (750 mL), followed by tert-butylnitrite (102 mL, 0.86 mmol) in THF (750 mL) at −50° C. The reaction was allowed to warmed to −5° C., diethyl ether (1.5 L) was added and the mixture reaction was stirred at −5° C. for 15 min until a pale of yellow solid precipitated. The yellow solid was collected and dissolved in acetonitrile (750 mL), and KI (55 g, 0.33 mmol), I$_2$ (42 g, 0.16 mmol) were added. The resulting mixture was stirred at room temperature for 15 min, partitioned between aqueous Na$_2$SO$_3$ solution (1 L) and dichloromethane (1 L). The organic layer was separated, dried over sodium sulfate, and concentrated under reduced pressure to give the crude product (66 g, 88%) as a yellow solid.

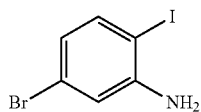

Step 2: 5-bromo-2-iodoaniline

To a solution of 4-bromo-1-iodo-2-nitrobenzene (66 g, 0.2 mol) in MeOH (700 mL) was added SnCl$_2$ (226 g, 1 mol) at 0° C. After 4 h at 80° C., the solvent was removed under reduced pressure. The residue was diluted with ethyl acetate (1 L) and washed with H$_2$O (1 L). The organic layer was separated, dried over sodium sulfate, concentrated under reduced pressure to give a residue which was purified by column chromatography(eluent:petroleum ether:ethyl acetate=20:1) to give a white solid (39 g, 65%).

LCMS (Method B): 3.08 min
m/z [MH]$^+$=298.1; 300.1

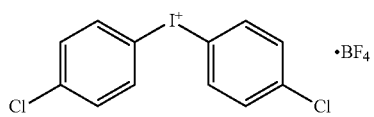

Step 3: bis(4-chlorophenyl)iodonium tetrafluoroborate

To a solution of m-CPBA (2.06 g, 12 mmol) in dichloromethane (50 mL) was added 1-chloro-4-iodobenzene (2.57 g, 10.8 mmol) followed by BF$_3$.OEt$_2$ (1.84 g, 13 mmol) at room temperature. The resultant mixture was stirred for 30 min at RT under nitrogen atmosphere and cooled to 0° C. (4-chlorophenyl)boronic acid (1.87 g, 12 mmol) was added and the reaction mixture was stirred at RT for 15 minutes. The solution was concentrated under reduced pressure to give a residue which was purified by column chromatography (eluent: dichloromethane:MeOH=20:1) to give a white solid (1.1 g, 28.7%).

LCMS (Method B): 1.68 min
m/z [MH]$^+$=348.9

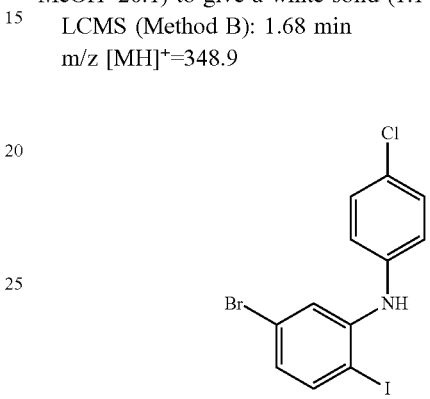

Step 4: 5-bromo-N-(4-chlorophenyl)-2-iodoaniline

To a solution of bis(4-chlorophenyl)iodonium tetrafluoroborate salt (from Step 3, 145 mg, 0.33 mmol) in dichloromethane (5 mL) at RT was added Na$_2$CO$_3$ (71 mg, 0.67 mmol), CuI (6.3 mg, 0.033 mmol) and 5-bromo-2-iodoaniline (149 mg, 0.5 mmol). The resulting mixture was stirred at RT overnight. The mixture was diluted with dichloromethane (10 mL), washed with H$_2$O (10 mL) and the organic layer was separated, dried over sodium sulfate, and concentrated under reduced pressure. The crude product was purified by column chromatography (eluent:petroleum ether) to give (80 mg, 39%) of the titled compound as a yellow solid.

LCMS (Method B): 2.81 min
$^1$H NMR (400 MHz, DMSO-d$_6$) δ ppm 7.00 (d, J=8.80 Hz 3 H) 7.22 (d, J=2.20 Hz 1 H) 7.29 (d, J=8.80 Hz 2 H) 7.70 (s, 1 H) 7.77 (d, J=8.40 Hz 1 H).
m/z [MH]$^+$=408; 410;

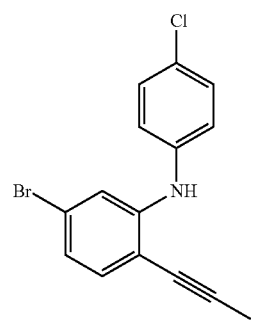 [SMILES: CC#Cc1ccc(Br)cc1Nc1ccc(Cl)cc1]

Step 5: 5-bromo-N-(4-chlorophenyl)-2-(prop-1-yn-1-yl)aniline

A mixture of 5-bromo-N-(4-chlorophenyl)-2-iodoaniline (80 mg, 0.2 mmol), trimethyl(prop-1-yn-1-yl)silane (88 mg, 0.8 mmol), Pd(PPh$_3$)$_4$(12 mg, 0.01 mmol), TBAF.H$_2$O (13 mg, 0.04 mmol), Et$_3$N (6 mg, 0.06 mmol), CuI (1 mg, 0.006 mmol) in toluene (4 mL) and THF (2 mL) was stirred at 70° C. overnight under N$_2$. The solvent was removed under reduced pressure and the residue was purified by column chromatography (eluent:petroleum ether:ethyl acetate=50:1) to give the titled compound (20 mg, 31%) as a white solid LCMS (Method B): 3.82 min $^1$H NMR (400 MHz, CDCl$_3$) δ ppm 2.15 (s, 3 H) 6.39 (s, 1 H) 6.90 (dd, J$_1$=8.20 Hz J$_2$=1.90 Hz 1 H) 7.20 (m, 4 H) 7.35 (d, J=2.00 Hz 2 H).

m/z [MH]$^+$=320; 322.

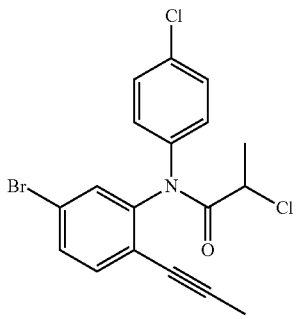 [SMILES: CC#Cc1ccc(Br)cc1N(C(=O)C(C)Cl)c1ccc(Cl)cc1]

Step 6: N-(5-bromo-2-(prop-1-yn-1-yl)phenyl)-2-chloro-N-(4-chlorophenyl)propanamide To a solution of 5-bromo-N-(4-chlorophenyl)-2-(prop-1-yn-1-yl)aniline (600 mg, 1.89 mmol) in toluene (15 mL) was added 2-chloropropanoyl chloride (318 mg, 2.82 mmol) and K$_2$CO$_3$ (774 mg, 5.64 mmol) at 0° C. After 4 h at 80° C., the mixture was quenched by H$_2$O. The organic layer was separated, dried over sodium sulfate, and concentrated under reduced pressure. The crude product was purified by column chromatography (eluent:petroleum ether:ethyl acetate=50:1) to give the desired product (550 mg, 73% yield) as a grey oil.

LCMS (Method B): 3.42 min m/z [MH]$^+$=412;

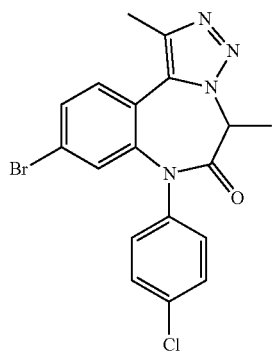 [SMILES: Cc1nnn2c1-c1ccc(Br)cc1N(c1ccc(Cl)cc1)C(=O)C2C]

Step 7: 9-bromo-7-(4-chlorophenyl)-1,5-dimethyl-5H-benzo[f][1,2,3]triazolo[1,5-d][1,4]diazepin-6(7H)-one To a solution of N-(5-bromo-2-(prop-1-ynyl)phenyl)-2-chloro-N-(4-chlorophenyl)propanamide (20.0 mg, 0.05 mmol) in DMF (5 mL) was added NaN$_3$ (9.5 mg, 0.15 mmol) and the resultant mixture was stirred at 130° C. for 45 min under nitrogen atmosphere. TLC analysis indicated that the reaction was complete. The reaction mixture was partitioned between water and ethyl acetate. The organic layer was separated and the aqueous layer was extracted twice with ethyl acetate. The organic layers were dried and concentrated under reduced pressure. The residue was purified by column chromatography (eluent:petroleum ether:ethyl acetate=5:1) to afford the title compound (11 mg 50%) as grey oil.

LCMS (Method B): 2.82 min m/z [MH]$^+$=419

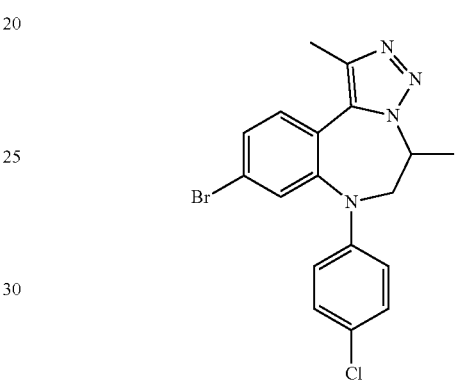

Step 8: 9-Bromo-7-(4-chlorophenyl)-1,5-dimethyl-6,7-dihydro-5H-benzo[f][1,2,3]triazolo[1,5-d][1,4]diazepine To a solution of N-(5-bromo-2-(prop-1-ynyl)phenyl)-2-chloro-N-(4-chlorophenyl)propanamide (17.0 mg, 0.04 mmol) in THF (3 mL) was added BH$_3$-THF (0.60 mL, 0.61 mmol) at 0° C. The resultant mixture was stirred at 40° C. for 6 h, cooled to RT and partitioned between water and ethyl acetate. The organic layer was separated and the aqueous layer was extracted twice with ethyl acetate. The organic layers were dried and concentrated under reduced pressure. The residue was purified by column chromatography (eluent:petroleum ether:ethyl acetate=1:1) to afford the title compound (8 mg 50%) as a grey oil.

LCMS (Method B): 3.32 min m/z [MH]$^+$=405

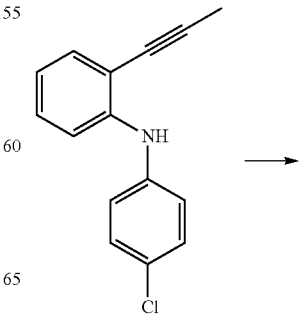

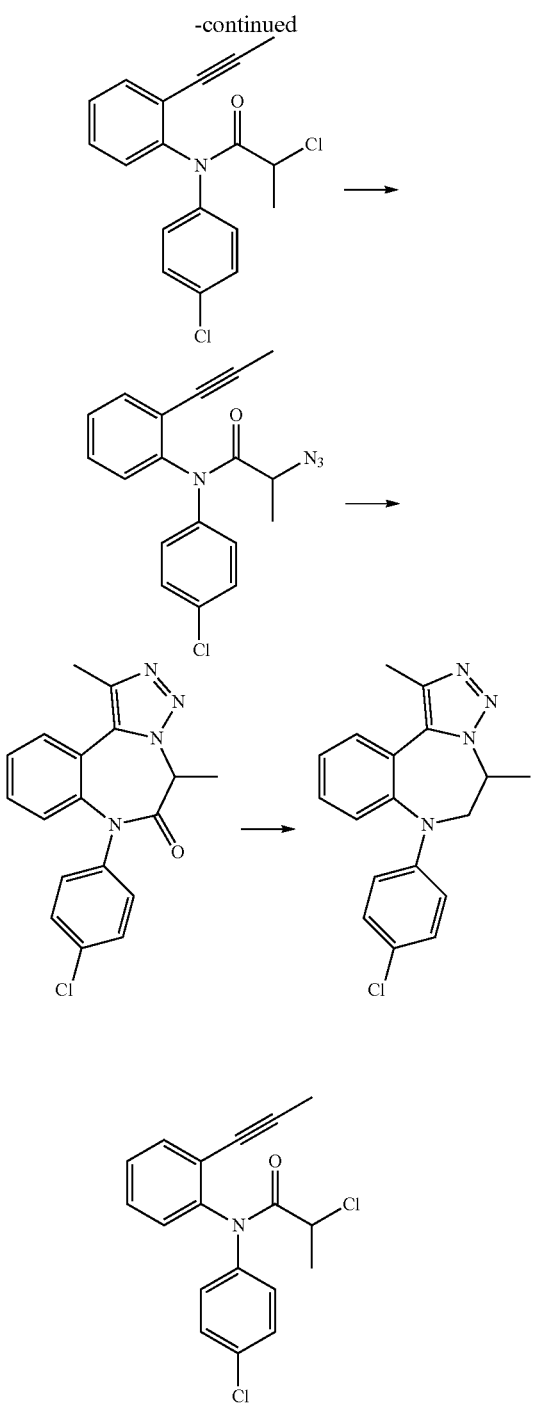

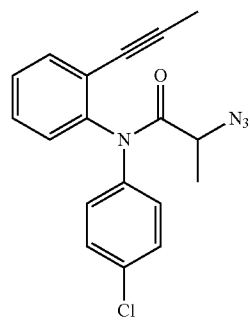 [SMILES: CC#Cc1ccccc1N(C(=O)C(C)N=[N+]=[N-])c1ccc(Cl)cc1]

Step 2: 2-azido-N-(4-chlorophenyl)-N-(2-(prop-1-ynyl)phenyl)propanamide

To a solution of 2-chloro-N-(4-chlorophenyl)-N-(2-(prop-1-ynyl)phenyl)propanamide (100 mg, 0.30 mmol, 1.0 eq) in dry DMF (6 mL) was added NaN$_3$ (60 mg, 0.9 mmol, 3.0 eq). The mixture was stirred at RT overnight. The mixture was used for the next step without further purification.

LCMS (Method B): 3.09 min m/z [MH]$^+$=339.1, 341.1

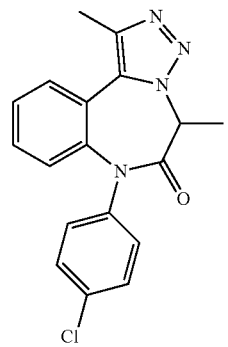 [SMILES: Cc1nnn2c1-c1ccccc1N(c1ccc(Cl)cc1)C(=O)C2C]

Step 3: 7-(4-chlorophenyl)-1,5-dimethyl-5H-benzo[f][1,2,3]triazolo[1,5-d][1,4]diazepin-6(7H)-one A solution of azido-N-(4-chlorophenyl)-N-(2-(prop-1-ynyl)phenyl)propanamide (0.30 mmol) in DMF (6 mL) was stirred at 110° C. under N$_2$ atmosphere for 2 h, and then cooled to RT. The resulting mixture was diluted with ethyl acetate (100 mL), washed with water (100 mL), dried (Na$_2$SO$_4$), concentrated, and purified by column chromatography on silica gel (petroleum ether-petroleum ether-~ethyl acetate=1:1) to give 7-(4-chlorophenyl)-1,5-dimethyl-5H-benzo[f][1,2,3]triazolo[1,5-d][1,4]diazepin-6(7H)-one (30 mg, 30%) as yellow solid.

LCMS (Method B): 2.57 min m/z [MH]$^+$=339.1, 341.1 leum ether to petroleum ether:ethyl acetate=10:1) to give 2-chloro-N-(4-chlorophenyl)-N-(2-(prop-1-ynyl)phenyl)propanamide (110 mg, 40%) as yellow oil.

LCMS (Method B): 2.98 min m/z [MH]$^+$=332.2, 334.2

Step 1: 2-chloro-N-(4-chlorophenyl)-N-(2-(prop-1-ynyl)phenyl)propanamide

To a solution of N-(4-chlorophenyl)-2-(prop-1-ynyl)benzenamine (200 mg, 0.83 mmol, 1.0 eq) in dioxane (5 mL) were added potassium carbonate (345 mg, 2.5 mmol, 3.0 eq) and 2-chloropropanoyl chloride (160 mg, 1.25 mmol, 1.5 eq). The mixture was stirred at 110° C. under microwave for 2 h. The mixture was cooled to room temperature, diluted with dichloromethane (100 mL), washed with water (3×100 mL), dried (Na$_2$SO$_4$), concentrated under reduced pressure, and purified by column chromatography on silica gel (petro-

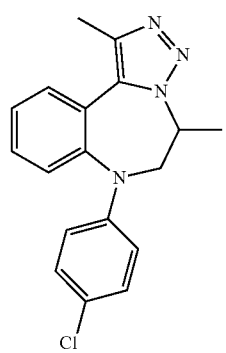 [SMILES: Cc1nnn2c1-c1ccccc1N(c1ccc(Cl)cc1)CC2C]

Step 4: 7-(4-chlorophenyl)-1,5-dimethyl-6,7-di-hydro-5H-benzo[f][1,2,3]triazolo[1,5-d][1,4]diaz-epine To a solution of 7-(4-chlorophenyl)-1,5-dimethyl-5H-benzo[f][1,2,3]triazolo[1,5-d][1,4]diazepin-6(7H)-one (30.0 mg, 0.09 mmol, 1.0 eq) in THF (2 mL) was added a solution of borane in THF (1M, 0.9 mL, 10.0 eq). The mixture was stirred at RT under $N_2$ atmosphere for 20 h. The mixture was diluted with ethyl acetate (100 mL), washed with water (100 mL), dried ($Na_2SO_4$), concentrated under reduced pressure and purified by pre-TLC (eluent:petroleum ether/ethyl acetate=2/1) to give the title compound (15 mg, 54%) as white solid.

LCMS (Method B): 3.00 min
m/z [MH]$^+$=325.1, 327.1

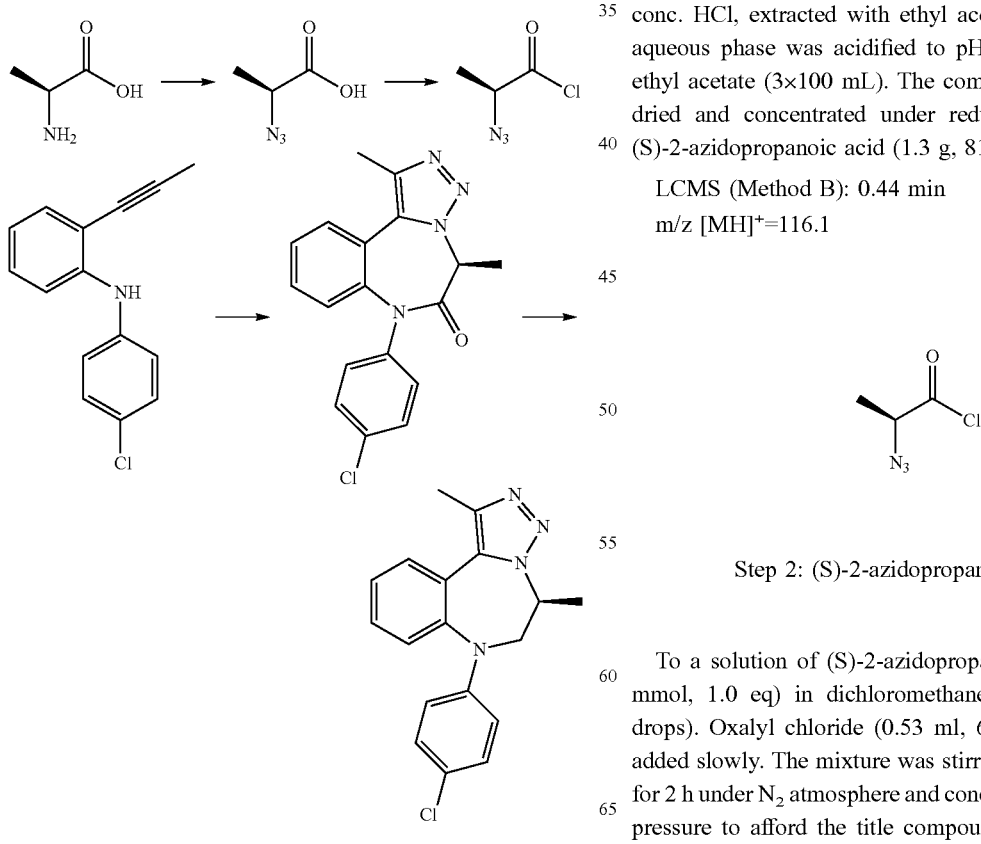

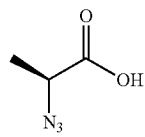

Step 1: (S)-2-azidopropanoic acid

Sodium azide (9.05 g, 13.93 mmol, 10.0 eq) was dissolved in distilled water (22.5 mL) and added to dichloromethane (35 mL) and cooled to 0° C. (ice-bath). Triflyl anhydride (4.7 mL, 27.86 mmol, 2.0 eq) was added slowly over 10 min and the reaction mixture was stirred for 2 h. The mixture was placed in a separatory funnel and dichloromethane phase was removed. The aqueous portion was extracted with dichloromethane (2×7.5 mL). The organic fractions containing the triflyl azide were washed once with saturated $Na_2CO_3$ and used without further purification. (S)-2-aminopropanoic acid (1.24 g, 13.93 mmol, 1.0 eq) was combined with $K_2CO_3$ (2.88 g, 20.90 mmol, 1.5 eq), and $CuSO_4.5H_2O$ (35 mg, 0.14 mmol, 0.01 eq) in distilled $H_2O$ (18 mL) and $CH_3OH$ (36 mL). The triflyl azide in dichloromethane was added. The mixture was stirred at ambient temperature and pressure overnight. Subsequently, the organic solvents were removed under reduced pressure and the aqueous slurry was diluted with $H_2O$ (50 mL). This was acidified to pH=6 with conc. HCl, extracted with ethyl acetate (3×100 mL). The aqueous phase was acidified to pH=2 and extracted with ethyl acetate (3×100 mL). The combined extractions were dried and concentrated under reduced pressure to give (S)-2-azidopropanoic acid (1.3 g, 81%) as a pale oil.

LCMS (Method B): 0.44 min
m/z [MH]$^+$=116.1

Step 2: (S)-2-azidopropanoyl chloride

To a solution of (S)-2-azidopropanoic acid (1.4 g, 12.4 mmol, 1.0 eq) in dichloromethane was added DMF (5 drops). Oxalyl chloride (0.53 ml, 6.2 mmol, 0.5 eq) was added slowly. The mixture was stirred at room temperature for 2 h under $N_2$ atmosphere and concentrated under reduced pressure to afford the title compound (12.4 mmol) which was used in the next step without further purification.

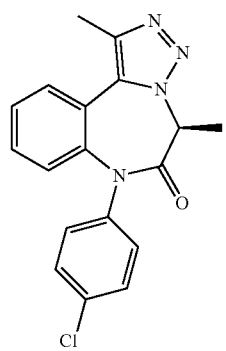 [SMILES: Cc1nnn2c1-c1ccccc1N(c1ccc(Cl)cc1)C(=O)[C@@H]2C]

Step 3: (5S)-7-(4-chlorophenyl)-1,5-dimethyl-5H-benzo[f][1,2,3]triazolo[1,5-d][1,4]diazepin-6(7H)-one In a microwave tube, N-(4-chlorophenyl)-2-(prop-1-ynyl)benzenamine (300 mg, 1.24 mmol, 1.0 eq) was dissolved in dioxane (5 mL), followed by addition of K₂CO₃ (514 mg, 3.72 mmol, 3.0 eq). The (S)-2-azidopropanoyl chloride (12.4 mmol) was added slowly. The mixture was stirred at 120° C. under MW for 1 h, cooled to RT, diluted with ethyl acetate (100 mL), washed with water (100 mL), dried (Na₂SO₄) and concentrated under reduced pressure. The crude oil was purified by column chromatography on silica gel (petroleum ether to petroleum ether:ethyl acetate=1:1) to give (5S)-7-(4-chlorophenyl)-1,5-dimethyl-5H-benzo[f][1,2,3]triazolo[1,5-d][1,4]diazepin-6(7H)-one (80 mg, 24%) as yellow oil.

LCMS (Method B): 2.54 min
m/z [MH]⁺=339.1, 341.1

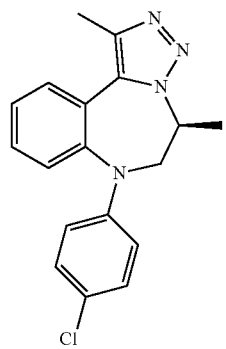 [SMILES: Cc1nnn2c1-c1ccccc1N(c1ccc(Cl)cc1)C[C@@H]2C]

Step 4: (5S)-7-(4-chlorophenyl)-1,5-dimethyl-6,7-dihydro-5H-benzo[f][1,2,3]triazolo[1,5-d][1,4]diazepine To a solution of (5S)-7-(4-chlorophenyl)-1,5-dimethyl-5H-benzo[f][1,2,3]triazolo[1,5-d][1,4]diazepin-6(7H)-one (80.0 mg, 0.24 mmol, 1.0 eq) in THF (2 mL) was added a solution of borane in THF (1M, 2.4 mL, 10.0 eq). The mixture was stirred at RT under N₂ atmosphere for 20 h. The mixture diluted with ethyl acetate (100 mL), washed with water (100 mL), dried (Na₂SO₄), concentrated under reduced pressure and purified by preparative TLC (eluent: petroleum ether/ethyl acetate=2/1) to give (5S)-7-(4-chlorophenyl)-1,5-dimethyl-6,7-dihydro-5H-benzo[f][1,2,3]triazolo[1,5-d][1,4]diazepine (20 mg, 26%) as white solid.

LCMS (Method B): 2.97 min
m/z [MH]⁺=325.1, 327.1

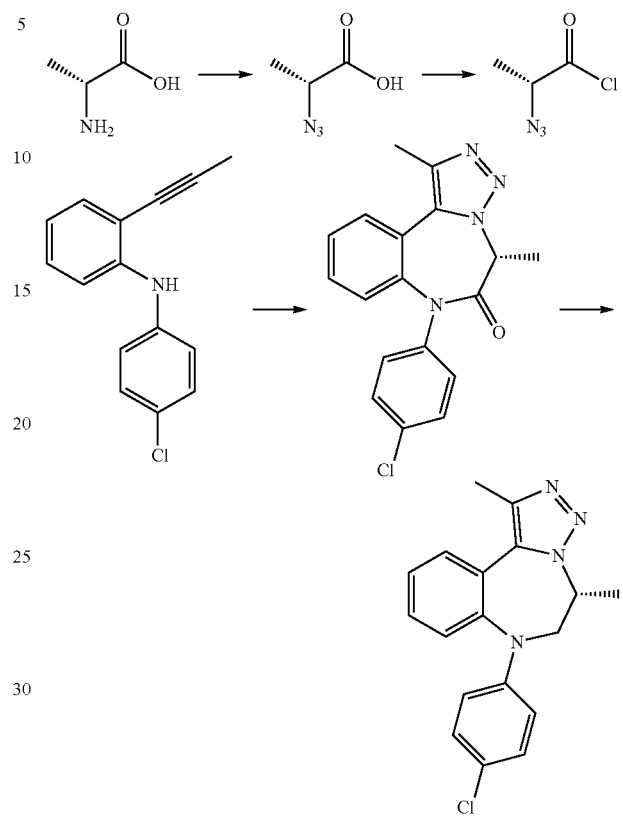

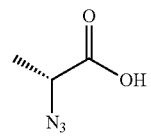

Step 1: (R)-2-azidopropanoic acid

Sodium azide (9.05 g, 13.93 mmol, 10.0 eq) was dissolved in distilled water (22.5 mL) and added to dichloromethane (35 mL) and cooled to 0° C. (ice-bath). Triflyl anhydride (4.7 mL, 27.86 mmol, 2.0 eq) was added slowly over 10 min and the reaction mixture was stirred for 2 h. The mixture was placed in a separatory funnel and dichloromethane phase was removed. The aqueous portion was extracted with dichloromethane (2×7.5 mL). The organic fractions containing the triflyl azide were washed once with saturated Na₂CO₃ and used without further purification. (R)-2-aminopropanoic acid (1.24 g, 13.93 mmol, 1.0 eq) was combined with K₂CO₃ (2.88 g, 20.90 mmol, 1.5 eq), and CuSO₄.5H₂O (35 mg, 0.14 mmol, 0.01 eq) in distilled H₂O (18 mL) and CH₃OH (36 mL). The triflyl azide in dichloromethane was added. The mixture was stirred at ambient temperature and pressure overnight. Subsequently, the organic solvents were removed under reduced pressure and the aqueous slurry was diluted with H₂O (50 mL). This was acidified to pH=6 with conc. HCl, extracted with ethyl acetate (3×100 mL). The aqueous phase was acidified to pH=2. and extracted with ethyl acetate (3×100 mL). The combined extractions were dried and concentrated under reduced pressure to give (R)-2-azidopropanoic acid (1.2 g, 75%) as a pale oil.

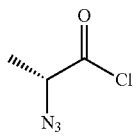

Step 2: (R)-2-azidopropanoyl chloride

To a solution of (R)-2-azidopropanoic acid (238 mg, 2.07 mmol, 1.0 eq) in dichloromethane was added DMF (5 drops). Oxalyl chloride (132 mg, 1.04 mmol, 0.5 eq) was added slowly. The mixture was stirred at RT for 2 h under a $N_2$ atmosphere. Then, the mixture was concentrated under reduced pressure to afford the title compound (2.07 mmol) which was used in the next step without further purification.

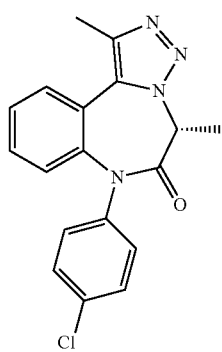 [SMILES: Cc1nnn2c1-c1ccccc1N(c1ccc(Cl)cc1)C(=O)[C@H]2C]

Step 3: (5R)-7-(4-chlorophenyl)-1,5-dimethyl-5H-benzo[f][1,2,3]triazolo[1,5-d][1,4]diazepin-6(7H)-one In a microwave tube, N-(4-chlorophenyl)-2-(prop-1-ynyl) benzenamine (100 mg, 0.41 mmol, 1.0 eq) was dissolved in dioxane (5 mL), followed by addition of $K_2CO_3$ (170 mg, 1.23 mmol, 3.0 eq). (R)-2-azidopropanoyl chloride (2.07 mmol) was then added slowly. The mixture was stirred at 150° C. under MW for 1 h. The mixture was cooled to RT, diluted with ethyl acetate (100 mL), washed with water (100 mL), dried ($Na_2SO_4$), concentrated under reduced pressure. The crude oil was purified by column chromatography (petroleum ether to petroleum ether/ethyl acetate=1/1) to give (5R)-7-(4-chlorophenyl)-1,5-dimethyl-5H-benzo[f][1,2,3]triazolo[1,5-d][1,4]diazepin-6(7H)-one (50 mg, 36%) as yellow solid.

LCMS (Method B): 2.55 min m/z [MH]$^+$=339.1, 341.1

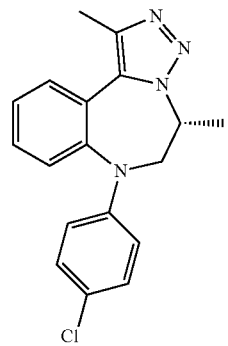 [SMILES: Cc1nnn2c1-c1ccccc1N(c1ccc(Cl)cc1)C[C@H]2C]

Step 4: (5R)-7-(4-chlorophenyl)-1,5-dimethyl-6,7-dihydro-5H-benzo[f][1,2,3]triazolo[1,5-d][1,4]diazepine To a solution of (5R)-7-(4-chlorophenyl)-1,5-dimethyl-5H-benzo[f][1,2,3]triazolo[1,5-d][1,4]diazepin-6(7H)-one (50.0 mg, 0.15 mmol, 1.0 eq) in THF (2 mL) was added a solution of borane in THF (1M, 1.5 mL, 10.0 eq). The mixture was stirred at 40° C. under $N_2$ atmosphere overnight. The mixture was then diluted with ethyl acetate (100 mL), washed with water (100 mL), dried ($Na_2SO_4$), concentrated under reduced pressure and purified by pre-HPLC to give (5R)-7-(4-chlorophenyl)-1,5-dimethyl-6,7-dihydro-5H-benzo[f][1,2,3]triazolo[1,5-d][1,4]diazepine (30 mg, 64%) as a white solid.

LCMS (Method B): 2.99 min m/z [MH]$^+$=325.1, 327.1

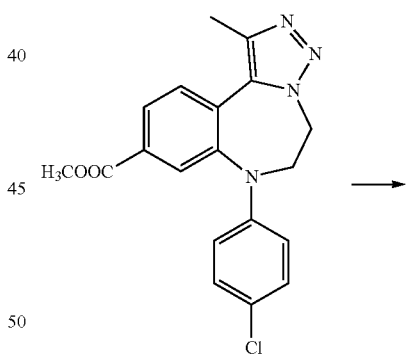

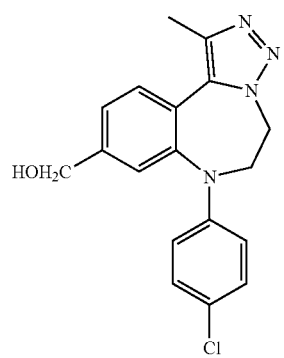 [SMILES: Cc1nnn2c1-c1ccc(CO)cc1N(c1ccc(Cl)cc1)CC2]

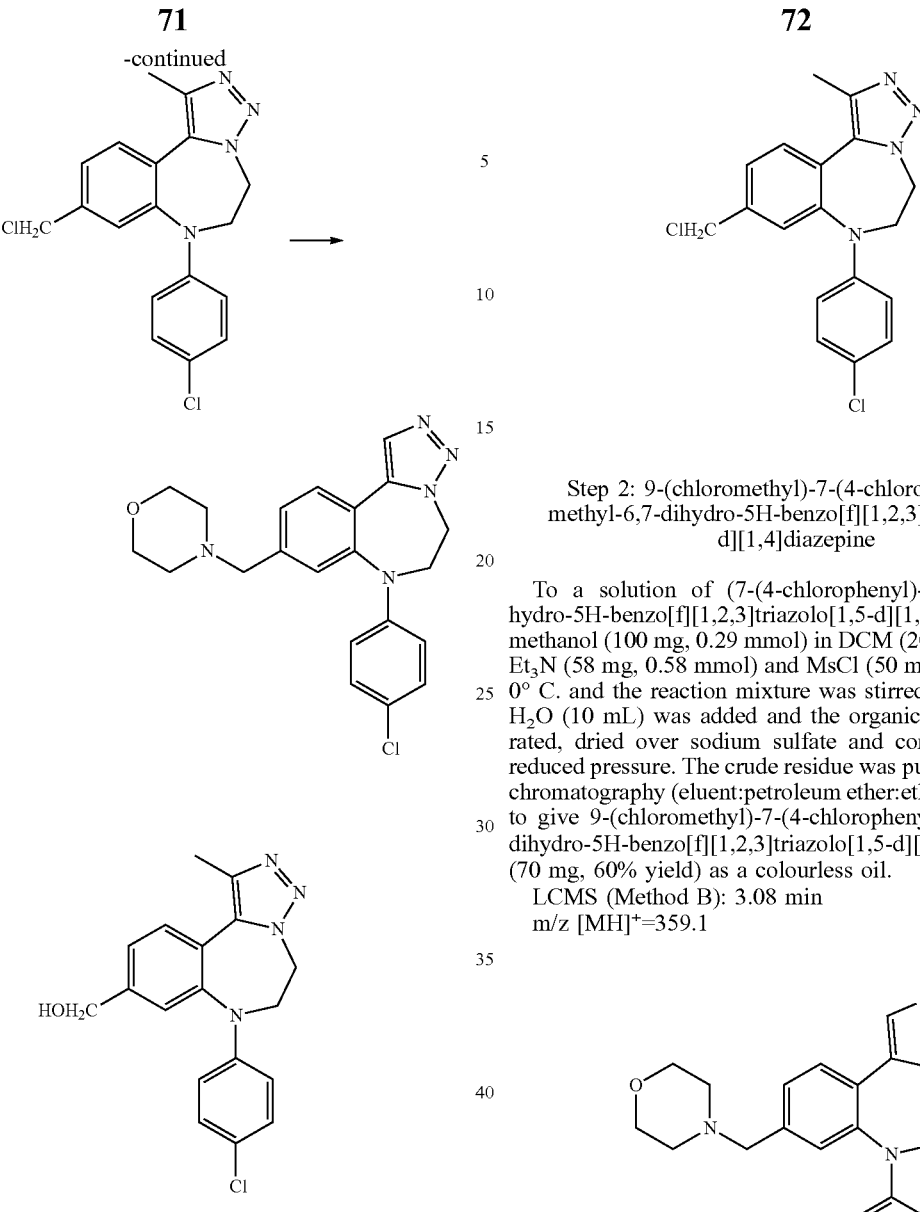

Step 1: (7-(4-chlorophenyl)-1-methyl-6,7-dihydro-5H-benzo[f][1,2,3]triazolo[1,5-d][1,4]diazepin-9-yl)methanol To a solution of methyl 7-(4-chlorophenyl)-1-methyl-6,7-dihydro-5H-benzo[f][1,2,3]triazolo[1,5-d][1,4]diazepine-9-carboxylate (170 mg, 0.46 mmol) in THF (5 mL) was added LiAlH4 (87 mg, 2.3 mmol) at 0° C. and the reaction mixture was stirred at room temperature for 16 h. H$_2$O (10 mL) was added and the mixture was reduced under reduced pressure to remove most of the THF. The mixture was then diluted with ethyl acetate (50 mL) and washed with H$_2$O (25 mL). The organic layer was separated, dried over sodium sulfate, and concentrated under reduced pressure. The crude product was purified by column chromatography (eluent: petroleum ether:ethyl acetate=2:1) to give (7-(4-chlorophenyl)-1-methyl-6,7-dihydro-5H-benzo[f][1,2,3]triazolo[1,5-d][1,4]diazepin-9-yl) methanol (90 mg, 48%) as a colourless oil.

LCMS (Method B): 2.60 min
m/z [MH]$^+$=341.1

Step 2: 9-(chloromethyl)-7-(4-chlorophenyl)-1-methyl-6,7-dihydro-5H-benzo[f][1,2,3]triazolo[1,5-d][1,4]diazepine To a solution of (7-(4-chlorophenyl)-1-methyl-6,7-dihydro-5H-benzo[f][1,2,3]triazolo[1,5-d][1,4]diazepin-9-yl)methanol (100 mg, 0.29 mmol) in DCM (20 mL) was added Et$_3$N (58 mg, 0.58 mmol) and MsCl (50 mg, 0.44 mmol) at 0° C. and the reaction mixture was stirred at RT for 12 h. H$_2$O (10 mL) was added and the organic layer was separated, dried over sodium sulfate and concentrated under reduced pressure. The crude residue was purified by column chromatography (eluent:petroleum ether:ethyl acetate=30:1) to give 9-(chloromethyl)-7-(4-chlorophenyl)-1-methyl-6,7-dihydro-5H-benzo[f][1,2,3]triazolo[1,5-d][1,4]diazepine (70 mg, 60% yield) as a colourless oil.

LCMS (Method B): 3.08 min
m/z [MH]$^+$=359.1

Step 3: 4-((7-(4-chlorophenyl)-6,7-dihydro-5H-benzo[f][1,2,3]triazolo[1,5-d][1,4]diazepin-9-yl)methyl)morpholine To a solution of 9-(chloromethyl)-7-(4-chlorophenyl)-1-methyl-6,7-dihydro-5H-benzo[f][1,2,3]triazolo[1,5-d][1,4] diazepine (20 mg, 0.06 mmol) in CH$_3$CN (2 mL) was added morpholine (14.5 mg, 0.17 mmol) and Na$_2$CO$_3$ (17 mg, 0.17 mmol) at 0° C. and the reaction mixture was stirred at RT for 12 h. H$_2$O (2 mL) was added and the mixture was concentrated under reduced pressure. Purification by preparative HPLC gave 4-((7-(4-chlorophenyl)-6,7-dihydro-5H-benzo[f][1,2,3]triazolo[1,5-d][1,4]diazepin-9-yl)methyl)morpholine (5 mg, 22% yield) as a colourless oil.

LCMS (Method B): 2.04 min
m/z [MH]$^+$=410.2

73

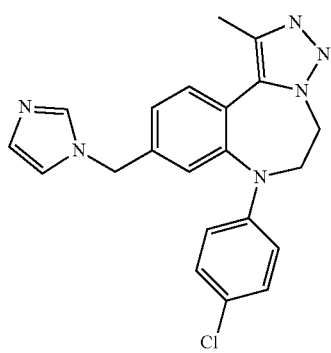 [SMILES: CC1=C2c3ccc(Cn4ccnc4)cc3N(c3ccc(Cl)cc3)CCN2NN1]

9-((1H-imidazol-1-yl)methyl)-7-(4-chlorophenyl)-1-methyl-6,7-dihydro-5H-benzo[f][1,2,3]triazolo[1,5-d][1,4]diazepine To a solution of 9-(chloromethyl)-7-(4-chlorophenyl)-1-methyl-6,7-dihydro-5H-benzo[f][1,2,3]triazolo[1,5-d][1,4]diazepine (25 mg, 0.07 mmol) in $CH_3CN$ (2 mL) was added 1H-imidazole (7.5 mg, 0.11 mmol) and $Et_3N$ (14 mg, 0.14 mmol) at 0° C. and the reaction mixture was stirred at RT for 12 h. $H_2O$ (2 mL) was added and the mixture was concentrated under reduced pressure. Purification by preparative HPLC gave 9-((1H-imidazol-1-yl)methyl)-7-(4-chlorophenyl)-1-methyl-6,7-dihydro-5H-benzo[f][1,2,3]triazolo[1,5-d][1,4]diazepine (5 mg, 19% yield) as a white solid.

LCMS (Method B): 1.99 min m/z $[MH]^+$=391.1

74

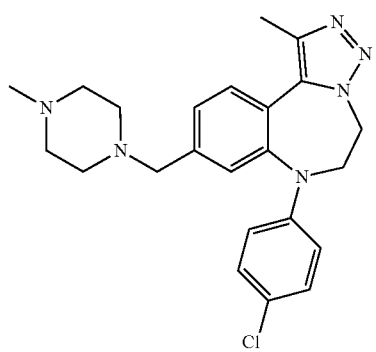

7-(4-chlorophenyl)-1-methyl-9-((4-methylpiperazin-1-yl)methyl)-6,7-dihydro-5H-benzo[f][1,2,3]triazolo[1,5-d][1,4]diazepine To a solution of 9-(chloromethyl)-7-(4-chlorophenyl)-1-methyl-6,7-dihydro-5H-benzo[f][1,2,3]triazolo[1,5-d][1,4]diazepine (39 mg, 0.09 mmol) in $CH_3CN$ (2 mL) was added 1-methylpiperazine (13 mg, 0.13 mmol) and $Et_3N$ (17 mg, 0.17 mmol) at 0° C. and the reaction mixture was stirred at RT for 12 h. $H_2O$ (2 mL) was added and the mixture was concentrated under reduced pressure. Purification by preparative HPLC gave 7-(4-chlorophenyl)-1-methyl-9-((4-methylpiperazin-1-yl)methyl)-6,7-dihydro-5H-benzo[f][1,2,3]triazolo[1,5-d][1,4]diazepine (10 mg, 28% yield) as a white solid.

LCMS (Method B): 1.95 min m/z $[MH]^+$=423.2

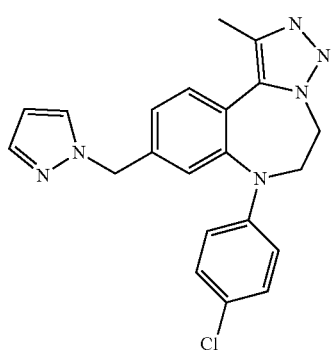 [SMILES: CC1=C2c3ccc(Cn4cccn4)cc3N(c3ccc(Cl)cc3)CCN2NN1]

9-((1H-pyrazol-1-yl)methyl)-7-(4-chlorophenyl)-1-methyl-6,7-dihydro-5H-benzo[f][1,2,3]triazolo[1,5-d][1,4]diazepine To a solution of 9-(chloromethyl)-7-(4-chlorophenyl)-1-methyl-6,7-dihydro-5H-benzo[f][1,2,3]triazolo[1,5-d][1,4]diazepine (40 mg, 0.06 mmol) in DMF (2 mL) was added 1H-pyrazole (12.0 mg, 0.18 mmol) and $Na_2CO_3$ (24 mg, 0.22 mmol) at 0° C. and the reaction mixture was stirred at RT for 12 h. $H_2O$ (2 mL) was added and the mixture was concentrated under reduced pressure. Purification by preparative HPLC gave 9-((1H-pyrazol-1-yl)methyl)-7-(4-chlorophenyl)-1-methyl-6,7-dihydro-5H-benzo[f][1,2,3]triazolo[1,5-d][1,4]diazepine (4 mg, 9% yield) as a white solid.

LCMS (Method B): 2.67 min m/z $[MH]^+$=391.1

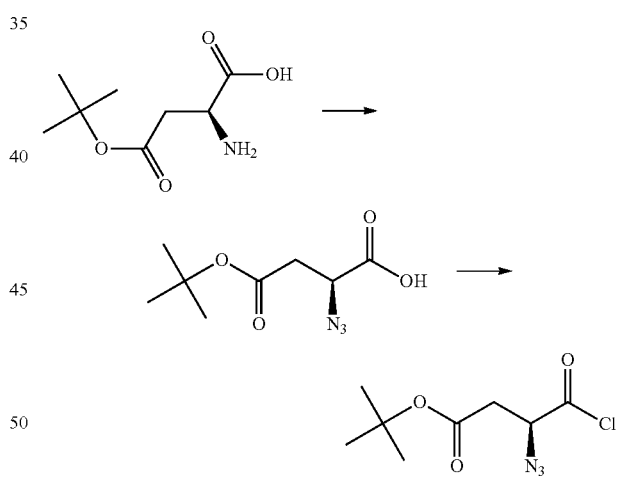

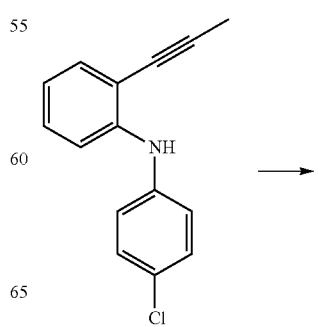

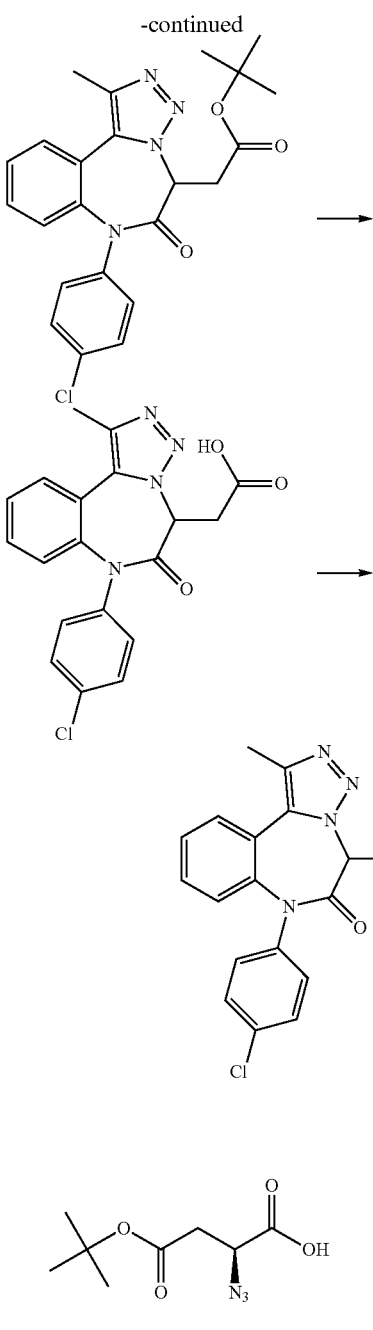

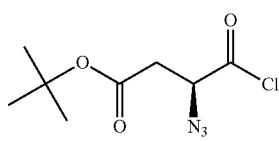

Step 2: (S)-tert-butyl 3-azido-4-chloro-4-oxobutanoate

To a solution of (S)-2-azido-4-tert-butoxy-4-oxobutanoic acid (668 mg, 3.1 mmol, 1.0 eq) in dichloromethane (5 mL) was added DMF (5 drops). Oxalyl chloride (0.27 mL, 3.1 mmol, 1 eq) was added slowly at room temperature. After 5 min at this temperature, the mixture was stirred at 40° C. for 5 min under N₂ atmosphere. Then, the mixture was concentrated under reduced pressure. The residue (3.1 mmol) was used for the next step without further purification.

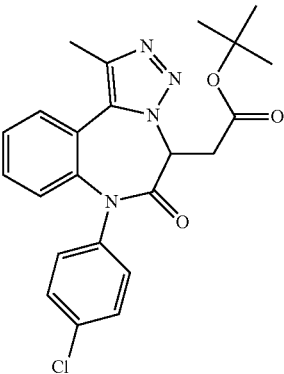 [SMILES: Cc1nnn2c1-c1ccccc1N(c1ccc(Cl)cc1)C(=O)C2CC(=O)OC(C)(C)C]

Step 3: tert-butyl 2-(7-(4-chlorophenyl)-1-methyl-6-oxo-6,7-dihydro-5H-benzo[f][1,2,3]triazolo[1,5-d][1,4]diazepin-5-yl)acetate N-(4-Chlorophenyl)-2-(prop-1-ynyl)benzenamine (250 mg, 1.03 mmol, 1.0 eq) was dissolved in toluene (5 mL), followed by addition of potassium carbonate (428 mg, 3.1 mmol, 3.0 eq). The (S)-tert-butyl 3-azido-4-chloro-4-oxobutanoate (step 2, 3.1 mmol) was then added slowly. The mixture was stirred at room temperature for 2 h under N₂ atmosphere, 40° C. overnight and then stirred at 130° C. for 3 h. The mixture was cooled to RT, diluted with ethyl acetate (100 mL), washed with water (100 mL), dried (Na₂SO₄), concentrated under reduced pressure and purified by column chromatography on silica gel (petroleum ether to petroleum Step 1: (S)-2-azido-4-tert-butoxy-4-oxobutanoic acid Sodium azide (10.0 g, 154 mmol, 7.3 eq) was dissolved in distilled water (22.5 mL) and added to dichloromethane (35 mL) and the mixture was cooled to 0° C. (ice-bath). Triflyl anhydride (7.0 mL, 42.0 mmol, 2.0 eq) was added slowly over 10 min and the mixture was stirred continuously for 2 h. The mixture was placed in a separatory funnel and the organic phase collected. The aqueous phase was extracted with dichloromethane (2×12.5 mL). The organic fractions containing the triflyl azide were washed once with saturated Na₂CO₃ and used without further purification. (S)-2-amino-4-tert-butoxy-4-oxobutanoic acid (4.0 g, 21 mmol, 1.0 eq) was combined with K₂CO₃ (4.3 g, 31.5 mmol, 1.5 eq), and CuSO₄·5H₂O (55 mg, 0.21 mmol, 0.01 eq), distilled H₂O (18 mL) and CH₃OH (36 mL). The triflyl azide in dichloromethane was added. The mixture was stirred RT overnight. Subsequently, the organic solvents were removed under reduced pressure and the aqueous slurry remaining was diluted with H₂O (50 mL). This was acidified to pH=6 with conc. HCl, extracted with ethyl acetate (3×100 mL) to remove sulfonamide by-product. The aqueous phase was acidified to pH=2. The product was obtained from another round of ethyl acetate extractions (3×100 mL), dried concentrated under reduced pressure to give (S)-2-azido-4-tert-butoxy-4-oxobutanoic acid (3.9 g, 87%) as a pale oil.

LCMS (Method B): 2.20 min
m/z [MNa]⁺=238.1 ether/ethyl acetate=1:1) to give tert-butyl 2-(7-(4-chlorophenyl)-1-methyl-6-oxo-6,7-dihydro-5H-benzo[f][1,2,3]triazolo[1,5-d][1,4]diazepin-5-yl)acetate (100 mg, 22%) as yellow oil.

LCMS (Method B): 2.91 min
m/z [MH]+=439.1

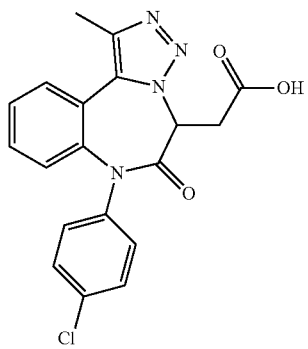 [SMILES: Cc1nnn2c1-c1ccccc1N(c1ccc(Cl)cc1)C(=O)C2CC(=O)O]

Step 4: 2-(7-(4-chlorophenyl)-1-methyl-6-oxo-6,7-dihydro-5H-benzo[f][1,2,3]triazolo[1,5-d][1,4]diazepin-5-yl)acetic acid TFA (1 mL) was added dropwise to an ice bath solution of tert-butyl 2-(7-(4-chlorophenyl)-1-methyl-6-oxo-6,7-dihydro-5H-benzo[f][1,2,3]triazolo[1,5-d][1,4]diazepin-5-yl)acetate (50 mg, 0.11 mmol, 1.0 eq) in dichloromethane (1 mL). The mixture was stirred at RT overnight, diluted with dichloromethane (30 mL), washed with H₂O (2×30 mL), dried and concentrated under reduced pressure to give 2-(7-(4-chlorophenyl)-1-methyl-6-oxo-6,7-dihydro-5H-benzo[f][1,2,3]triazolo[1,5-d][1,4]diazepin-5-yl)acetic acid (43 mg, 100%) as a yellow oil.

LCMS (Method B): 2.51 min
m/z [MH]+=383.1, 385.1

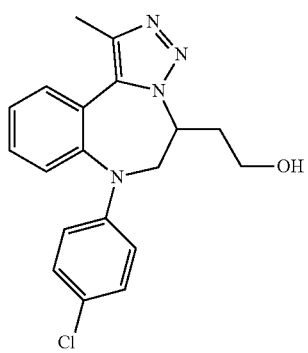 [SMILES: Cc1nnn2c1-c1ccccc1N(c1ccc(Cl)cc1)CC2CCO]

Step 5: 2-(7-(4-chlorophenyl)-1-methyl-6,7-dihydro-5H-benzo[f][1,2,3]triazolo[1,5-d][1,4]diazepin-5-yl)ethanol To a solution of 2-(7-(4-chlorophenyl)-1-methyl-6-oxo-6,7-dihydro-5H-benzo[f][1,2,3]triazolo[1,5-d][1,4]diazepin-5-yl)acetic acid (43.0 mg, 0.0.11 mmol, 1.0 eq) in THF (1 mL) was added a solution of borane in THF (1M, 1.1 mL, 10.0 eq). The mixture was stirred at RT under N₂ atmosphere for 20 h. The mixture diluted with ethyl acetate (100 mL), washed with water (100 mL), dried (Na₂SO₄), concentrated under reduced pressure and purified by preparative HPLC to give 2-(7-(4-chlorophenyl)-1-methyl-6,7-dihydro-5H-benzo[f][1,2,3]triazolo[1,5-d][1,4]diazepin-5-yl)ethanol (20 mg, 51%) as white solid.

LCMS (Method B): 2.90 min
m/z [MH]+=355.1, 357.1

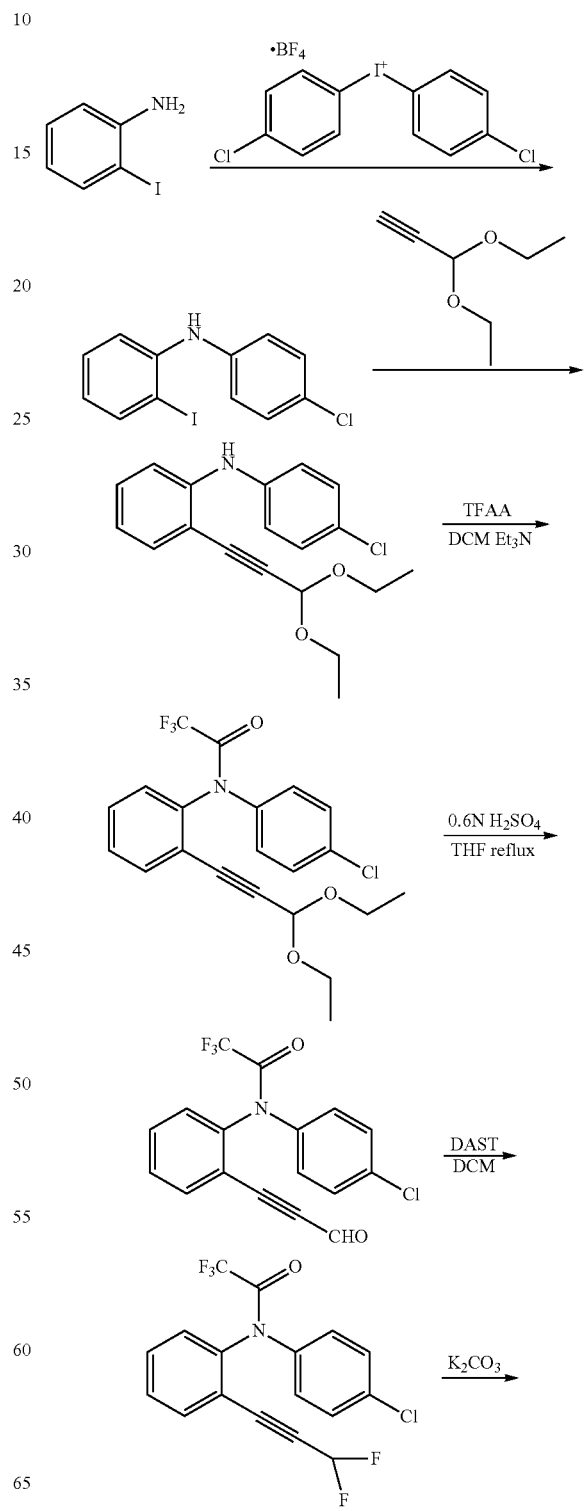

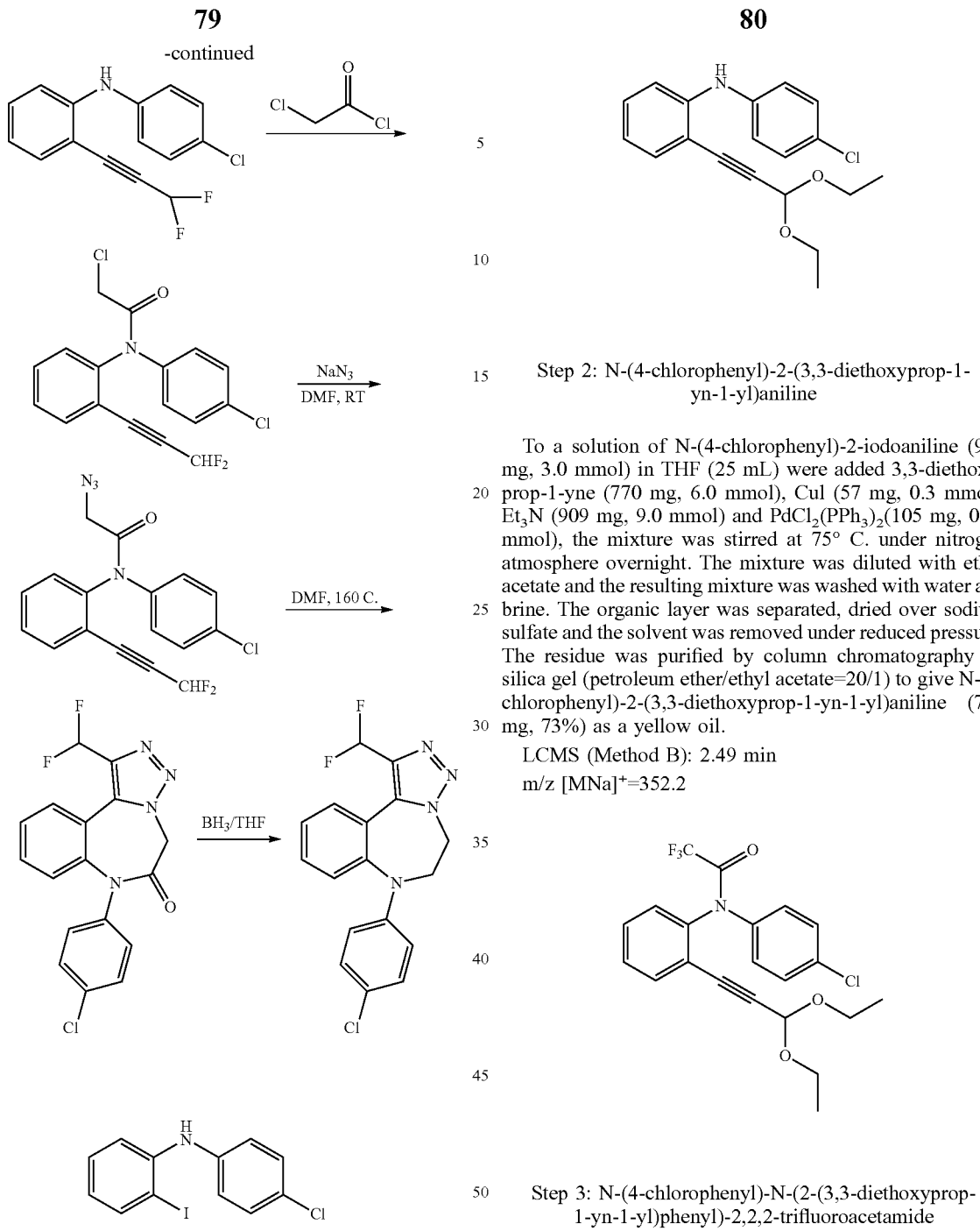

Step 2: N-(4-chlorophenyl)-2-(3,3-diethoxyprop-1-yn-1-yl)aniline

To a solution of N-(4-chlorophenyl)-2-iodoaniline (990 mg, 3.0 mmol) in THF (25 mL) were added 3,3-diethoxyprop-1-yne (770 mg, 6.0 mmol), CuI (57 mg, 0.3 mmol), Et$_3$N (909 mg, 9.0 mmol) and PdCl$_2$(PPh$_3$)$_2$(105 mg, 0.15 mmol), the mixture was stirred at 75° C. under nitrogen atmosphere overnight. The mixture was diluted with ethyl acetate and the resulting mixture was washed with water and brine. The organic layer was separated, dried over sodium sulfate and the solvent was removed under reduced pressure. The residue was purified by column chromatography on silica gel (petroleum ether/ethyl acetate=20/1) to give N-(4-chlorophenyl)-2-(3,3-diethoxyprop-1-yn-1-yl)aniline (720 mg, 73%) as a yellow oil.

LCMS (Method B): 2.49 min m/z [MNa]$^+$=352.2

Step 3: N-(4-chlorophenyl)-N-(2-(3,3-diethoxyprop-1-yn-1-yl)phenyl)-2,2,2-trifluoroacetamide To a solution of N-(4-chlorophenyl)-2-(3,3-diethoxyprop-1-yn-1-yl)aniline (200 mg, 0.6 mmol) in dichloromethane (10 mL) were added triethylamine (10 mg, 1.8 mmol) and 2,2,2-trifluoroacetic anhydride (189 mg, 0.9 mmol). The mixture was stirred for 12 h at room temperature, and the resulting mixture was washed with water and brine. The organic layer was separated, dried over sodium sulfate and concentrated under reduced pressure to give a residue which was purified by column chromatography on silica gel (petroleum ether/ethyl acetate=10/1) to give N-(4-chlorophenyl)-N-(2-(3,3-diethoxyprop-1-yn-1-yl)phenyl)-2,2,2-trifluoroacetamide (70 mg, 28%) as a yellow oil.

LCMS (Method B): 3.31 min m/z [MNa]$^+$=448.1;

Step 1: N-(4-chlorophenyl)-2-iodoaniline bis(4-chlorophenyl)iodonium tetrafluoroborate salt (5.00 g, 11.4 mmol), 2-iodoaniline (3.76 g, 17.2 mmol), CuI (214 mg, 1.1 mmol) and Na$_2$CO$_3$ (2.43 g, 22.9 mmol) were added in dichloromethane (100 mL). The resultant mixture was stirred overnight at RT under nitrogen atmosphere. Water (50 mL) was added. The organic layer was separated, dried and concentrated under reduced pressure. The residue was purified by column chromatography (eluent: pure petroleum ether) to give N-(4-chlorophenyl)-2-iodoaniline (3.50 g, 92%) as a colourless oil.

LCMS (Method B):

m/z 3.48 min [MH]$^+$=329.9.

81

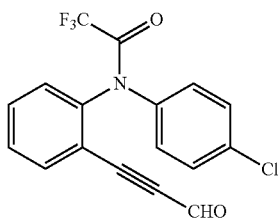 [SMILES: O=CC#Cc1ccccc1N(C(=O)C(F)(F)F)c1ccc(Cl)cc1]

Step 4: N-(4-chlorophenyl)-2,2,2-trifluoro-N-(2-(3-oxoprop-1-yn-1-yl)phenyl)acetamide To a solution of N-(4-chlorophenyl)-N-(2-(3,3-diethoxy-prop-1-yn-1-yl)phenyl)-2,2,2-trifluoroacetamide (70 mg, 0.16 mmol) in THF (1.6 mL) and H$_2$O (1.6 mL) was added conc. H$_2$SO$_4$ (66 µL) at RT. The reaction mixture was stirred at 100° C. for 3 h. The mixture was diluted with ethyl acetate and washed with saturated sodium carbonate aqueous solution. The organic layer was separated, dried over sodium sulfate and concentrated under reduced pressure. The residue was purified by column chromatography on silica gel (petroleum ether/ethyl acetate=10/1) to give N-(4-chlorophenyl)-2,2,2-trifluoro-N-(2-(3-oxoprop-1-yn-1-yl)phenyl)acetamide (27 mg, 48%) as a yellow oil.

LCMS (Method B): 2.74 min m/z [MH]$^+$=352.2

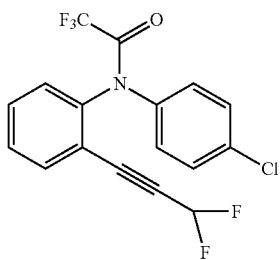 [SMILES: O=C(N(c1ccc(Cl)cc1)c1ccccc1C#CC(F)F)C(F)(F)F]

Step 5: N-(4-chlorophenyl)-N-(2-(3,3-difluoroprop-1-yn-1-yl)phenyl)-2,2,2-trifluoroacetamide To a solution of N-(4-chlorophenyl)-2,2,2-trifluoro-N-(2-(3-oxoprop-1-yn-1-yl)phenyl) acetamide (27 mg, 0.08 mmol) in dichloromethane (3 mL) was added DAST (25 mg, 0.15 mmol) at room temperature. The reaction mixture was stirred at RT for 1 h. The mixture was washed with H$_2$O. The organic layer was separated, dried (Na$_2$SO$_4$) and concentrated under reduced pressure. The residue was purified by preparative TLC (petroleum ether/ethyl acetate=10/1) to give N-(4-chlorophenyl)-N-(2-(3,3-difluoroprop-1-yn-1-yl)phenyl)-2,2,2-trifluoroacetamide (25 mg, 86%) as a yellow oil.

LCMS (Method B): 3.03 min m/z [MH]$^+$=374.2

82

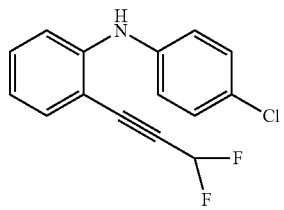 [SMILES: FC(F)C#Cc1ccccc1Nc1ccc(Cl)cc1]

Step 6: N-(4-chlorophenyl)-2-(3,3-difluoroprop-1-yn-1-yl)aniline

To a solution of N-(4-chlorophenyl)-N-(2-(3,3-difluoro-prop-1-yn-1-yl)phenyl)-2,2,2-trifluoroacetamide (25 mg, 0.07 mmol) in MeOH (5 mL) was added K$_2$CO$_3$ (19 mg, 0.14 mmol) in H$_2$O (1 mL) at room temperature. The reaction mixture was stirred at RT for 4 h. The solvent was removed under reduced pressure to give a residue which was diluted with ethyl acetate and washed with H$_2$O. The organic layer was separated, dried over sodium sulfate and concentrated under reduced pressure. The residue was purified by preparative TLC (petroleum ether/ethyl acetate=10/1) to give N-(4-chlorophenyl)-2-(3,3-difluoroprop-1-yn-1-yl)aniline (15 mg, 81%) as a white solid.

LCMS (Method B): 3.34 min m/z [MH]$^+$=278.1

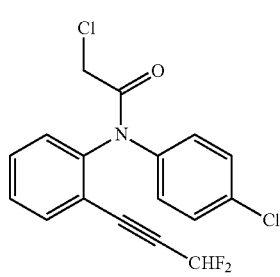 [SMILES: O=C(CCl)N(c1ccc(Cl)cc1)c1ccccc1C#CC(F)F]

Step 7: 2-chloro-N-(4-chlorophenyl)-N-(2-(3,3-difluoroprop-1-yn-1-yl)phenyl)acetamide To a solution of N-(4-chlorophenyl)-2-(3,3-difluoroprop-1-yn-1-yl)aniline (450 mg, 1.62 mmol) in toluene (10 mL) were added 2-chloroacetyl chloride (310 mg, 2.74 mmol) and K$_2$CO$_3$ (370 mg, 2.68 mmol) at 0° C. The mixture was heated to 80° C. for 4 h, cooled to RT and H$_2$O (10 mL) was added. The organic layer was separated, dried over sodium sulfate, and concentrated under reduced pressure to give a crude product which was purified by column chromatography (eluent:petroleum ether:ethyl acetate=50:1) to give 2-chloro-N-(4-chlorophenyl)-N-(2-(3,3-difluoroprop-1-yn-1-yl)phenyl)acetamide (100 mg, 47%) as a yellow oil.

LCMS (Method B): 2.89 min m/z [MH]$^+$=354.0.

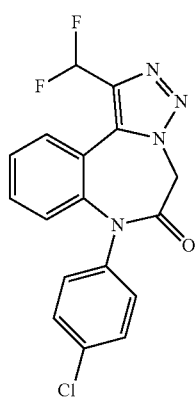 [SMILES: O=C1Cn2nnc(C(F)F)c2-c2ccccc2N1c1ccc(Cl)cc1]

Step 8: 7-(4-chlorophenyl)-1-(difluoromethyl)-5H-benzo[f][1,2,3]triazolo[1,5-d][1,4]diazepin-6(7H)-one 2-Chloro-N-(4-chlorophenyl)-N-(2-(3,3-difluoroprop-1-yn-1-yl)phenyl)acetamide (50 mg, 0.14 mmol) and NaN₃ (28 mg, 0.42 mmol) were added in DMF (5 mL) and the resulting mixture was stirred at room temperature overnight. The mixture was diluted with ethyl acetate (30 mL) and washed with H₂O (10 mL). The organic layer was separated, and concentrated under reduced pressure to give the azide intermediate. The azide intermediate (50 mg, 0.14 mmol) was redissolved in DMF (2.5 mL) and the mixture was heated to 155° C. for 6 h. Cooled to RT, the mixture was diluted with ethyl acetate (10 mL) and washed with water (10 mL). The organic layer was separated, dried over sodium sulfate, and concentrated under reduced pressure. The crude oil was purified by preparative TLC (eluent:petroleum ether:ethyl acetate=4:1) to give 7-(4-chlorophenyl)-1-(difluoromethyl)-5H-benzo[f][1,2,3]triazolo[1,5-d][1,4]diazepin-6(7H)-one (25 mg, 50%) as a white solid.

LCMS (Method B): 2.67 min
m/z [MH]⁺=361.1.

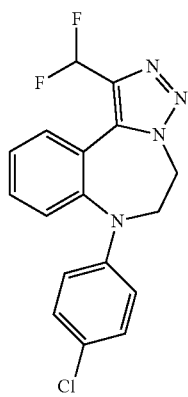 [SMILES: FC(F)c1nnn2c1-c1ccccc1N(c1ccc(Cl)cc1)CC2]

Step 9: 7-(4-chlorophenyl)-1-(difluoromethyl)-6,7-dihydro-5H-benzo[f][1,2,3]triazolo[1,5-d][1,4]diazepine To a solution of 7-(4-chlorophenyl)-1-(difluoromethyl)-5H-benzo[f][1,2,3]triazolo[1,5-d][1,4]diazepin-6(7H)-one (25 mg, 0.07 mmol) in THF (0.5 mL) was added a solution of BH₃ in THF (1M, 0.42 mL, 0.42 mmol). The mixture was stirred 4 h at room temperature, and then was quenched with methanol. The reaction mixture was concentrated to give a residue which was diluted with ethyl acetate (10 mL), washed with H₂O (5 mL). The organic layer was separated, dried over sodium sulfate, and concentrated under reduced pressure. The crude oil was purified by prep. TLC (eluent: petroleum ether:ethyl acetate=4:1) to give 7-(4-chlorophenyl)-1-(difluoromethyl)-6,7-dihydro-5H-benzo[f][1,2,3]triazolo[1,5-d][1,4]diazepine (12.5 mg, 50%) as a white solid.

LCMS (Method B): 2.93 min
m/z [MH]⁺=347.1;

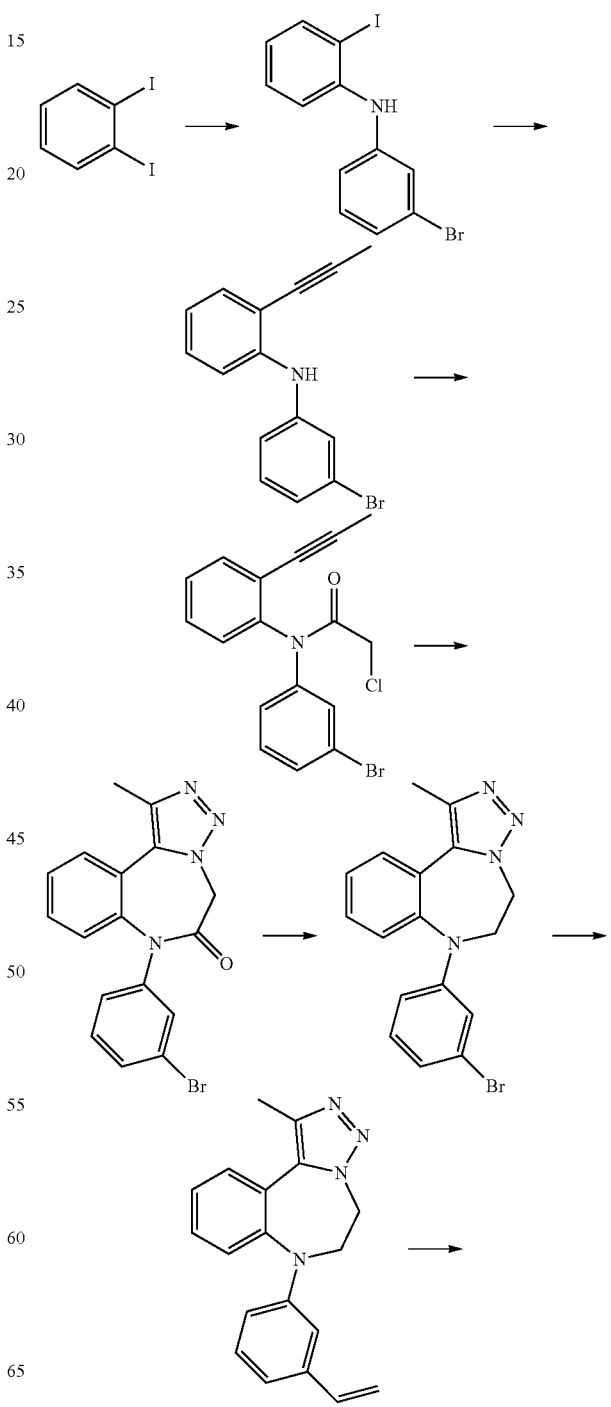

-continued

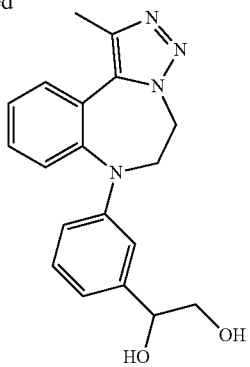

Step 1: 3-bromo-N-(2-iodophenyl)benzenamine

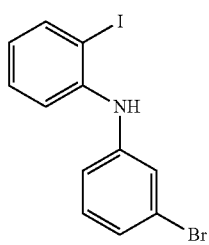 [SMILES: Brc1cccc(Nc2ccccc2I)c1]

To a mixture of 1,2-diiodobenzene (659.8 mg, 2.0 mmol) and 3-bromoaniline (344 mg, 2.0 mmol) in toluene (20 mL) were added cesium carbonate (759 mg, 2.5 mmol), Pd$_2$(dba)$_3$ (14 mg, 0.02 mmol) and Xantphos (57.8 mg, 0.1 mmol). The resultant mixture was stirred at 110° C. under nitrogen atmosphere overnight. The mixture was diluted with ethyl acetate (10 mL), washed with water (10 mL). The organic layer was separated, dried over sodium sulfate, and concentrated under reduced pressure. The crude product was purified by column chromatography (eluent:petroleum ether:ethyl acetate=10:1) to give 3-bromo-N-(2-iodophenyl)benzenamine (105 mg, 14%) as a yellow oil.

LCMS (Method B): 3.46 min
m/z [MH]$^+$=375; 377

Step 2: 3-bromo-N-(2-(prop-1-ynyl)phenyl)benzenamine

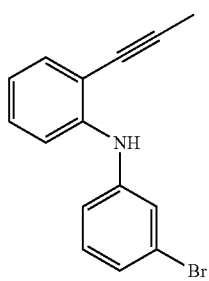 [SMILES: CC#Cc1ccccc1Nc1cccc(Br)c1]

A mixture of 3-bromo-N-(2-iodophenyl)benzenamine (4.0 g, 10.7 mmol), trimethyl(prop-1-yn-1-yl)silane (4.8 g, 42.8 mmol), Pd(PPh$_3$)$_4$(618 mg, 0.54 mmol), TBAF.H$_2$O (3.4 g, 10.7 mmol), Et$_3$N (323 mg, 3.2 mmol), CuI (61.1 mg, 0.32 mmol) in toluene (100 mL) and THF (50 mL) was stirred at RT overnight under N$_2$. The mixture was diluted with ethyl acetate (10 mL) and washed with H$_2$O (10 mL). The organic layer was separated, dried over sodium sulfate, and concentrated under reduced pressure. The crude product was purified by column chromatography (eluent:petroleum ether:ethyl acetate=50:1) to give 3-bromo-N-(2-(prop-1-ynyl)phenyl)benzenamine (85 mg, 29%) as a yellow oil.

LCMS (Method B): 3.57 min
m/z [MH]$^+$=286; 288.

Step 3: N-(3-bromophenyl)-2-chloro-N-(2-(prop-1-ynyl)phenyl)acetamide

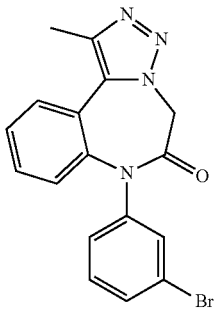 [SMILES: Cc1nnn2c1-c1ccccc1N(c1cccc(Br)c1)C(=O)C2]

To a solution of 3-bromo-N-(2-(prop-1-ynyl)phenyl)benzenamine (400 mg, 1.4 mmol) in toluene (15 mL) was added 2-chloroacetyl chloride (630 mg, 5.6 mmol) and triethylamine (430 mg, 4.2 mmol) at 0° C. The resultant mixture was stirred at 110° C. under nitrogen atmosphere for 4 h. The mixture was quenched with water. The organic layer was separated, dried over sodium sulfate, and concentrated under reduced pressure. The crude product was purified by column chromatography (eluent: petroleum ether:ethyl acetate=10:1) to give N-(3-bromophenyl)-2-chloro-N-(2-(prop-1-ynyl)phenyl)acetamide (115 mg, 23%) as a yellow oil.

LCMS (Method B): 2.93 min
m/z [MH]$^+$=362; 364.

Step 4: 7-(3-bromophenyl)-1-methyl-5H-benzo[f][1,2,3]triazolo[1,5-d][1,4]diazepin-6(7H)-one To a solution of N-(3-bromophenyl)-2-chloro-N-(2-(prop-1-ynyl)phenyl)acetamide (60.0 mg, 0.18 mmol) in DMF (5 mL) was added NaN$_3$ (33 mg, 0.54 mmol). The resultant mixture was stirred at RT for 2 h under nitrogen atmosphere. Then the reaction mixture was filtered and DMF (5 mL) was added. The resultant mixture was stirred at 150° C. for 4 h under nitrogen atmosphere. Water and ethyl acetate were added to the mixture. The organic layer was separated and the aqueous layer was extracted with ethyl acetate (2×). The organic layers were dried and concentrated to give a residue which was purified by column chromatography (eluent: dichloromethane:MeOH=30:1) to afford 7-(3-bromophenyl)-1-methyl-5H-benzo[f][1,2,3]triazolo[1,5-d][1,4]diazepin-6(7H)-one (39 mg 59%) as yellow oil LCMS (Method B): 2.52 min
m/z [MH]$^+$=369; 371.

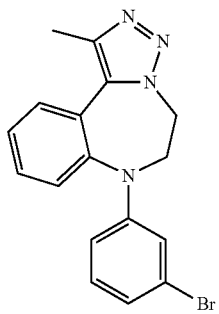 [SMILES: Cc1nnn2c1-c1ccccc1N(c1cccc(Br)c1)CC2]

Step 5: 7-(3-Bromophenyl)-1-methyl-6,7-dihydro-5H-benzo[f][1,2,3]triazolo[1,5-d][1,4]diazepine To a solution of 7-(3-bromophenyl)-1-methyl-5H-benzo[f][1,2,3]triazolo[1,5-d][1,4]diazepin-6(7H)-one (150 mg, 0.4 mmol) in THF (8 mL) was added a solution of BH$_3$ in THF (1M, 6.1 ml, 6.1 mmol) at 0° C. The resultant mixture was stirred at room temperature for 4 h and partitioned between water and ethyl acetate. The organic layer was separated and the aqueous layer was extracted with ethyl acetate (2×). The organic layers was dried and concentrated under reduced pressure. The residue was purified by column chromatography (eluent:petroleum ether:ethyl acetate=1:1) to afford 7-(3-bromophenyl)-1-methyl-6,7-dihydro-5H-benzo[f][1,2,3]triazolo[1,5-d][1,4]diazepine (100 mg, 69%) as grey oil.

LCMS (Method B): 2.93 min
m/z [MH]$^+$=355.0, 357.0;

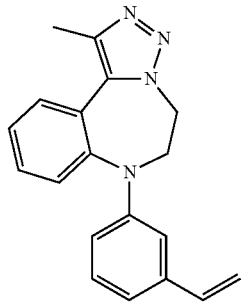 [SMILES: C=Cc1cccc(N2CCn3nnc(C)c3-c3ccccc32)c1]

Step 6: 1-Methyl-7-(3-vinylphenyl)-6,7-dihydro-5H-benzo[f][1,2,3]triazolo[1,5-d][1,4]diazepine To a solution of 7-(3-bromophenyl)-1-methyl-6,7-dihydro-5H-benzo[f][1,2,3]triazolo[1,5-d][1,4]diazepine (100.0 mg, 0.28 mmol) in THF (3 mL) and n-PrOH (10 mL) was added potassium vinyltrifluoroborate (75.4 mg, 0.56 mmol), PdCl$_2$(dppf) (8.2 mg, 0.012 mmol) and triethylamine (56.6 mg, 0.56 mmol). The resultant mixture was stirred at 100° C. under nitrogen atmosphere overnight. TLC analysis indicated that the reaction was complete. The reaction mixture was partitioned between water and ethyl acetate. The organic layer was separated and the aqueous layer was extracted with ethyl acetate (2×). The organic layers was dried and concentrated under reduced pressure to give a residue which was purified by column chromatography ((eluent:petroleum ether:ethyl acetate=1:1) to give 1-methyl-7-(3-vinylphenyl)-6,7-dihydro-5H-benzo[f][1,2,3]triazolo[1,5-d][1,4]diazepine (70 mg, 70%) as a grey solid.

LCMS (Method B): 2.91 min
m/z [MH]$^+$=303;

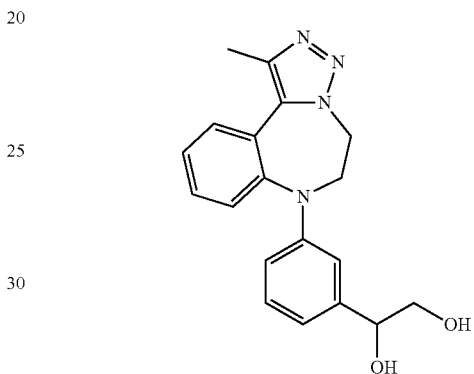

Step 7: 1-(3-(1-methyl-5H-benzo[f][1,2,3]triazolo[1,5-d][1,4]diazepin-7(6H)-yl)phenyl)ethane-1,2-diol A solution of AD-mix (327 mg) in t-BuOH (10 mL) and H$_2$O (10 mL) was stirred at rt for 15 min and then cooled to 0° C. 1-methyl-7-(3-vinylphenyl)-6,7-dihydro-5H-benzo[f][1,2,3]triazolo[1,5-d][1,4]diazepine (70.0 mg, 0.23 mmol) was added. The resultant mixture was stirred at 0° C. for 6 h and partitioned between water and ethyl acetate. The organic layer was separated and the aqueous layer was extracted with ethyl acetate (2×). The organic layers were dried and concentrated under reduced pressure to give a residue which was purified by column chromatography (dichloromethane-dichloromethane: MeOH=10:1) to afford 1-(3-(1-methyl-5H-benzo[f][1,2,3]triazolo[1,5-d][1,4]diazepin-7(6H)-yl)phenyl)ethane-1,2-diol (46 mg, 60%) as white solid.

LCMS (Method B): 2.26 min
m/z [MH]$^+$=337.2;

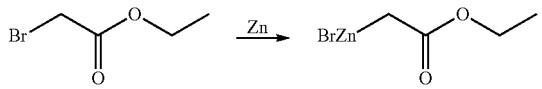

89
-continued

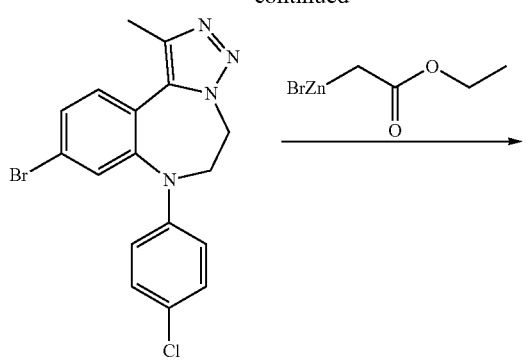

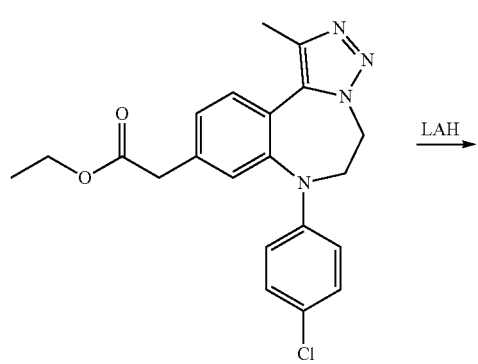

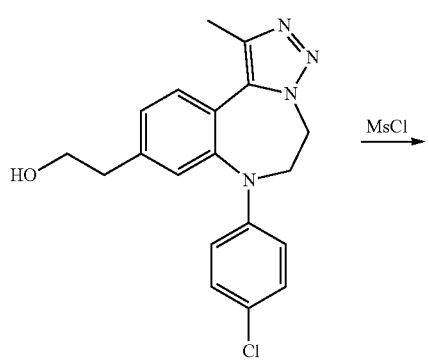

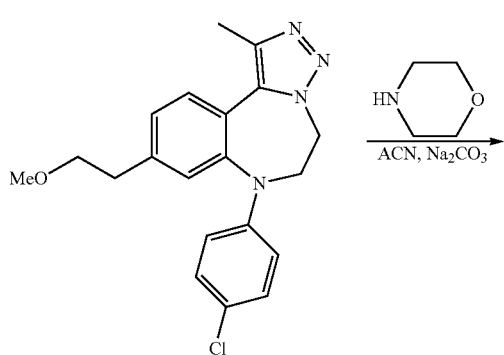

90
-continued

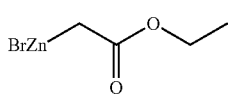

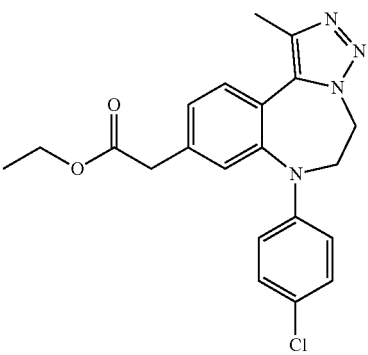 [SMILES: CCOC(=O)Cc1ccc2c(c1)N(c1ccc(Cl)cc1)CCn1nnc(C)c1-2]

Step 1: (2-ethoxy-2-oxoethyl)zinc(II) bromide

Under nitrogen atmosphere, zinc powder (50.0 g, 458 mmol) was suspended in THF (50 mL) and Me$_3$SiCl (3.0 mL, 22.9 mmol) was added dropwise at RT. The resultant mixture was stirred for 30 min at 40° C. A solution of ethyl 2-bromoacetate (25.4 mL, 229 mmol) in THF (100 mL) was added to the above reaction mixture at RT. The resultant mixture was stirred at RT overnight, and then allowed to stand at RT for 1 h. The mixture was filtered and the filtrate was used in the next step without further purification.

Step 2: ethyl 2-(7-(4-chlorophenyl)-1-methyl-6,7-dihydro-5H-benzo[f][1,2,3]triazolo[1,5-d][1,4]diazepin-9-yl)acetate To a solution of 9-bromo-7-(4-chlorophenyl)-1-methyl-6,7-dihydro-5H-benzo[f][1,2,3]triazolo[1,5-d][1,4]diazepine (500 mg, 1.3 mmol), XPhos (62 mg, 0.13 mmol), Pd$_2$(dba)$_3$ (118 mg, 0.13 mmol) in toluene (15 mL) was added a THF solution of (2-ethoxy-2-oxoethyl)zinc(II) bromide (1.5 M, 2.6 mL, 3.9 mmol) at RT under nitrogen atmosphere. The resulting mixture was stirred at 110° C. over 12 h. The mixture was diluted with ethyl acetate (20 mL) and washed with H$_2$O (20 mL). The organic layer was separated, dried and concentrated under reduced pressure. The residue was purified by column chromatography on silica gel (petroleum ether/ethyl acetate=10:1) to give ethyl 2-(7-(4-chlorophenyl)-1-methyl-6,7-dihydro-5H-benzo[f][1,2,3]triazolo[1,5-d][1,4]diazepin-9-yl)acetate (65 mg, 12%) as a colourless oil.

LCMS (Method B): 2.98 min
m/z [MH]$^+$=397.1.

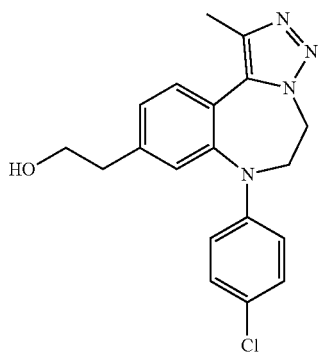 [SMILES: Cc1nnn2c1-c1ccc(CCO)cc1N(c1ccc(Cl)cc1)CC2]

Step 3: 2-(7-(4-chlorophenyl)-1-methyl-6,7-dihydro-5H-benzo[f][1,2,3]triazolo[1,5-d][1,4]diazepin-9-yl)ethanol To a solution of ethyl 2-(7-(4-chlorophenyl)-1-methyl-6,7-dihydro-5H-benzo[f][1,2,3]triazolo[1,5-d][1,4]diazepin-9-yl)acetate (65 mg, 0.16 mmol) in THF (5 mL) was added LiAlH$_4$ (25 mg, 0.64 mmol) at 0° C. under nitrogen atmosphere. The mixture was stirred for 6 h at RT. H$_2$O (1 mL) was added to quench the reaction, and the organic solvent was removed under reduced pressure. The residue was extracted with ethyl acetate. The organic layer was washed with water, brine, dried and concentrated under reduced pressure. The residue was purified by column chromatography on silica gel (petroleum ether/ethyl acetate=10:1) to give 2-(7-(4-chlorophenyl)-1-methyl-6,7-dihydro-5H-benzo[f][1,2,3]triazolo[1,5-d][1,4]diazepin-9-yl)ethanol (65 mg, 12%) as a colourless oil.

LCMS (Method B): 2.64 min
m/z [MH]$^+$=355.1.

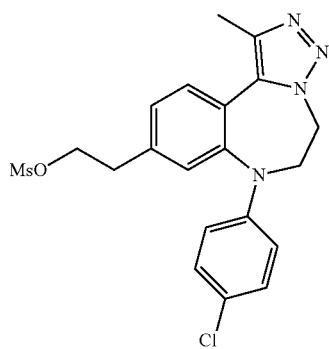 [SMILES: Cc1nnn2c1-c1ccc(CCOS(C)(=O)=O)cc1N(c1ccc(Cl)cc1)CC2]

Step 4: 2-(7-(4-chlorophenyl)-1-methyl-6,7-dihydro-5H-benzo[f][1,2,3]triazolo[1,5-d][1,4]diazepin-9-yl)ethyl methanesulfonate To a solution of 2-(7-(4-chlorophenyl)-1-methyl-6,7-dihydro-5H-benzo[f][1,2,3]triazolo[1,5-d][1,4]diazepin-9-yl)ethanol (30 mg, 0.085 mmol) in dichloromethane (5 mL) were added methanesulfonyl chloride (15 mg, 0.13 mmol) and TEA (17 mg, 0.17 mmol) at room temperature. The reaction mixture was stirred at RT for 4 h. LCMS and TLC analysis indicated that the reaction was complete. The mixture was diluted with ethyl acetate and washed with 1M HCl aqueous solution and saturated Na$_2$CO$_3$ aqueous solution. The resulting organic layer was dried over sodium sulfate and concentrated under reduced pressure to give 2-(7-(4-chlorophenyl)-1-methyl-6,7-dihydro-5H-benzo[f][1,2,3]triazolo[1,5-d][1,4]diazepin-9-yl)ethyl methanesulfonate (35 mg, 98%) as colourless oil.

LCMS (Method B): 2.6 min
m/z [MH]$^+$=433.1.

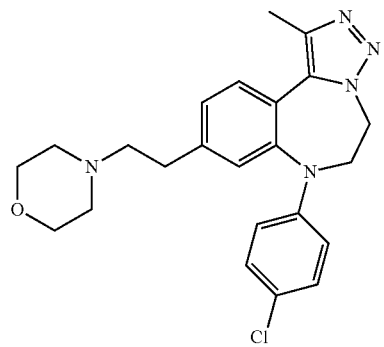 [SMILES: Cc1nnn2c1-c1ccc(CCN3CCOCC3)cc1N(c1ccc(Cl)cc1)CC2]

Step 5: 4-(2-(7-(4-chlorophenyl)-1-methyl-6,7-dihydro-5H-benzo[f][1,2,3]triazolo[1,5-d][1,4]diazepin-9-yl)ethyl)morpholine To a solution of 2-(7-(4-chlorophenyl)-1-methyl-6,7-dihydro-5H-benzo[f][1,2,3]triazolo[1,5-d][1,4]diazepin-9-yl)ethyl methanesulfonate (35 mg, 0.081 mmol) in CH$_3$CN (5 mL) were added morpholine (21 mg, 0.24 mmol) and Na$_2$CO$_3$ (26 mg, 0.24 mmol) at RT. The reaction mixture was stirred at RT overnight. The mixture was diluted with ethyl acetate and washed with water. The resulting organic layer was dried over sodium sulfate and concentrated under reduced pressure. The crude product was purified by preparative TLC (eluent: ethyl acetate) to give 4-(2-(7-(4-chlorophenyl)-1-methyl-6,7-dihydro-5H-benzo[f][1,2,3]triazolo[1,5-d][1,4]diazepin-9-yl)ethyl)morpholine (10 mg, 29%) as a white solid.

LCMS (Method B): 2.07 min
m/z [MH]$^+$=424.2.

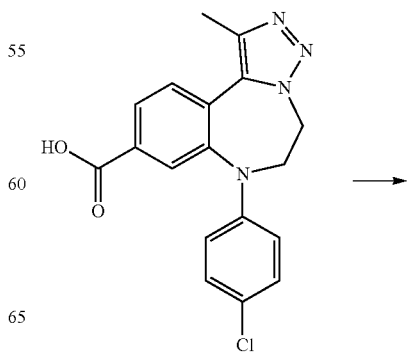

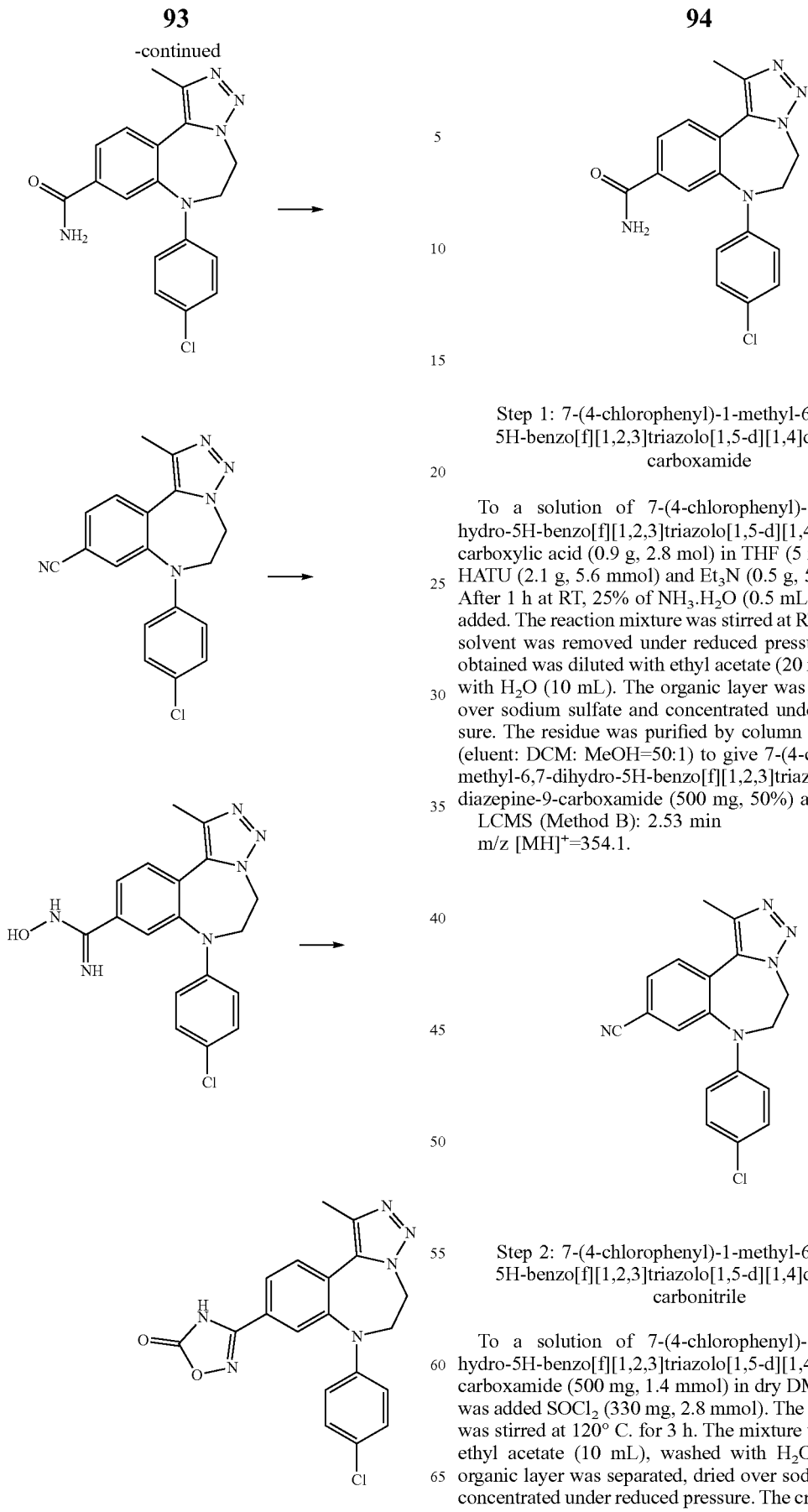

Step 1: 7-(4-chlorophenyl)-1-methyl-6,7-dihydro-5H-benzo[f][1,2,3]triazolo[1,5-d][1,4]diazepine-9-carboxamide To a solution of 7-(4-chlorophenyl)-1-methyl-6,7-dihydro-5H-benzo[f][1,2,3]triazolo[1,5-d][1,4]diazepine-9-carboxylic acid (0.9 g, 2.8 mol) in THF (5 mL) were added HATU (2.1 g, 5.6 mmol) and Et$_3$N (0.5 g, 5.6 mol) at 0° C. After 1 h at RT, 25% of NH$_3$.H$_2$O (0.5 mL, 7.5 mmol) was added. The reaction mixture was stirred at RT overnight. The solvent was removed under reduced pressure. The residue obtained was diluted with ethyl acetate (20 mL) and washed with H$_2$O (10 mL). The organic layer was separated, dried over sodium sulfate and concentrated under reduced pressure. The residue was purified by column chromatography (eluent: DCM: MeOH=50:1) to give 7-(4-chlorophenyl)-1-methyl-6,7-dihydro-5H-benzo[f][1,2,3]triazolo[1,5-d][1,4]diazepine-9-carboxamide (500 mg, 50%) as a white solid.

LCMS (Method B): 2.53 min
m/z [MH]$^+$=354.1.

Step 2: 7-(4-chlorophenyl)-1-methyl-6,7-dihydro-5H-benzo[f][1,2,3]triazolo[1,5-d][1,4]diazepine-9-carbonitrile To a solution of 7-(4-chlorophenyl)-1-methyl-6,7-dihydro-5H-benzo[f][1,2,3]triazolo[1,5-d][1,4]diazepine-9-carboxamide (500 mg, 1.4 mmol) in dry DMF (5 mL) at RT was added SOCl$_2$ (330 mg, 2.8 mmol). The reaction mixture was stirred at 120° C. for 3 h. The mixture was diluted with ethyl acetate (10 mL), washed with H$_2$O (10 mL). The organic layer was separated, dried over sodium sulfate, and concentrated under reduced pressure. The crude product was purified by column chromatography (eluent: DCM:

MeOH=100:1) to give 7-(4-chlorophenyl)-1-methyl-6,7-dihydro-5H-benzo[f][1,2,3]triazolo[1,5-d][1,4]diazepine-9-carbonitrile (210 mg, 45%) as a white solid.

LCMS (Method B): 2.79 min m/z [MH]$^+$=336.1.

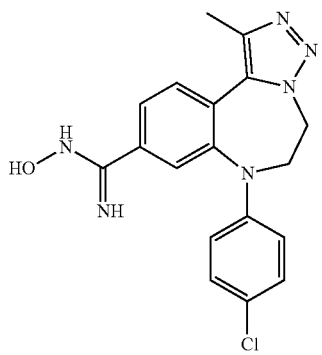

Step 3: 7-(4-chlorophenyl)-N-hydroxy-1-methyl-6,7-dihydro-5H-benzo[f][1,2,3]triazolo[1,5-d][1,4]diazepine-9-carboximidamide 7-(4-Chlorophenyl)-1-methyl-6,7-dihydro-5H-benzo[f][1,2,3]triazolo[1,5-d][1,4]diazepine-9-carbonitrile (200 mg, 0.6 mmol), hydroxylamine. HCl (63 mg, 1.2 mmol) and $K_2CO_3$ (124 mg, 0.9 mmol) were combined in MeOH (10 mL) and the mixture was stirred at 45° C. for 6 h. The solvent was removed under reduced pressure to give a residue which was diluted with ethyl acetate (20 mL) and washed with $H_2O$ (10 mL). The organic layer was dried over sodium sulfate and concentrated under reduced pressure. The residue was purified by column chromatography (eluent: DCM: MeOH=20:1) to give 7-(4-chlorophenyl)-N-hydroxy-1-methyl-6,7-dihydro-5H-benzo[f][1,2,3]triazolo[1,5-d][1,4]diazepine-9-carboximidamide (0.1 g, 45%) as a white solid.

LCMS (Method B): 2.42 min m/z [MH]$^+$=369.1.

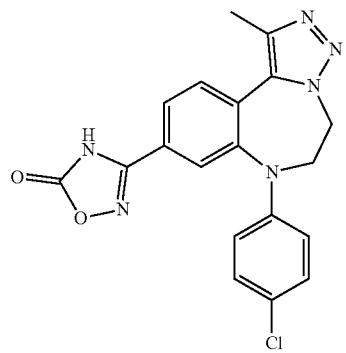 [SMILES: Cc1nnn2c1-c1ccc(-c3noc(=O)[nH]3)cc1N(c1ccc(Cl)cc1)CC2]

Step 4: 3-(7-(4-chlorophenyl)-1-methyl-6,7-dihydro-5H-benzo[f][1,2,3]triazolo[1,5-d][1,4]diazepin-9-yl)-1,2,4-oxadiazol-5(4H)-one 7-(4-chlorophenyl)-N-hydroxy-1-methyl-6,7-dihydro-5H-benzo[f][1,2,3]triazolo[1,5-d][1,4]diazepine-9-carboximidamide (100 mg, 0.27 mmol), CDI (53 mg, 0.33 mmol) and $K_2CO_3$ (56 mg, 0.4 mmol) were combined in DMSO (3 mL) and stirred at RT overnight. The mixture was diluted with ethyl acetate (20 mL), washed with $H_2O$ (10 mL) and the organic layer was dried over sodium sulfate and concentrated under reduced pressure. The residue was purified by column chromatography(eluent: DCM: MeOH=20:1) to give 3-(7-(4-chlorophenyl)-1-methyl-6,7-dihydro-5H-benzo[f][1,2,3]triazolo[1,5-d][1,4]diazepin-9-yl)-1,2,4-oxadiazol-5(4H)-one (60 mg, 56%) as a white solid.

LCMS (Method B): 2.75 min m/z [MH]$^+$=395.2.

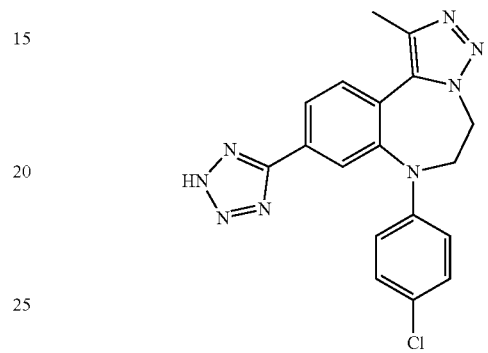

7-(4-chlorophenyl)-1-methyl-9-(2H-tetrazol-5-yl)-6,7-dihydro-5H-benzo[f][1,2,3]triazolo[1,5-d][1,4]diazepine A mixture of 7-(4-chlorophenyl)-1-methyl-6,7-dihydro-5H-benzo[f][1,2,3]triazolo[1,5-d][1,4]diazepine-9-carbonitrile (134 mg, 0.4 mol), $NaN_3$ (52 mg, 0.8 mmol) and $NH_4Cl$ (42 mg, 0.8 mol) in DMF (3 mL) were stirred at 150° C. for 24 h. The reaction mixture was cooled to RT and diluted with ethyl acetate (20 mL) and washed with $H_2O$ (10 mL). The organic layer was separated, dried over sodium sulphate and concentrated under reduced pressure. The residue was purified by preparative HPLC to give 7-(4-chlorophenyl)-1-methyl-9-(2H-tetrazol-5-yl)-6,7-dihydro-5H-benzo[f][1,2,3]triazolo[1,5-d][1,4]diazepine (12 mg, 8%) as a white solid.

LCMS (Method B): 2.65 min m/z [MH]$^+$=379.1

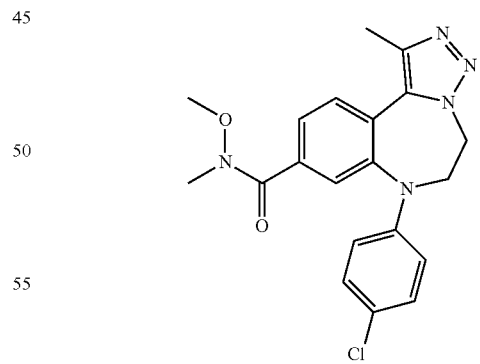

7-(4-Chlorophenyl)-N-methoxy-N, 1-dimethyl-6,7-dihydro-5H-benzo[f][1,2,3]triazolo[1,5-d][1,4]diazepine-9-carboxamide 7-(4-Chlorophenyl)-1-methyl-6,7-dihydro-5H-benzo[f][1,2,3]triazolo[1,5-d][1,4]diazepine-9-carboxylic acid (170 mg, 0.45 mmol) and HATU (256 mg, 0.67 mmol) were combined in THF (5 mL) and stirred at RT for 15 min. N-methoxymethanamine hydrochloride (38 mg, 0.7 mmol) and TEA (136.5 mg, 1.35 mmol) were then added. The resultant mixture was stirred for 4 h at RT. The mixture was filtered, partitioned between ethyl acetate and water and the organic phase was separated and dried over $Na_2SO_4$. The solvent was evaporated under reduced pressure and the residue was purified by flash chromatography (eluent: DCM:MeOH=20:1) to afford 7-(4-Chlorophenyl)-N-methoxy-N,1-dimethyl-6,7-dihydro-5H-benzo[f][1,2,3]triazolo[1,5-d][1,4]diazepine-9-carboxamide (30 mg, 16%) as yellow oil.

LCMS (Method B): 2.62 min m/z $[MH]^+$=398.3.

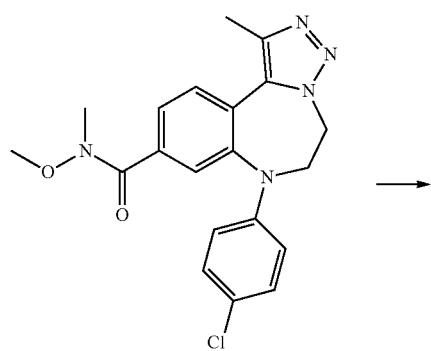

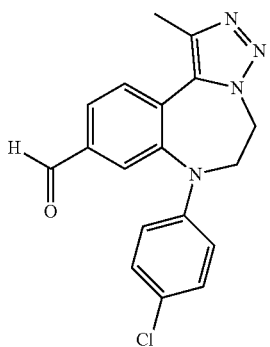 [SMILES: Cc1nnn2c1-c1ccc(C=O)cc1N(c1ccc(Cl)cc1)CC2]

Step 1: 7-(4-chlorophenyl)-1-methyl-6,7-dihydro-5H-benzo[f][1,2,3]triazolo[1,5-d][1,4]diazepine-9-carbaldehyde To a solution of 7-(4-chlorophenyl)-N-methoxy-N, 1-dimethyl-6,7-dihydro-5H-benzo[f][1,2,3]triazolo[1,5-d][1,4]diazepine-9-carboxamide (50 mg, 0.13 mmol) in THF (5 mL) was added $LiAlH_4$ (6 mg, 0.15 mmol). The reaction mixture was stirred at RT under $N_2$ overnight. The reaction was quenched with $H_2O$, then extracted with ethyl acetate and dried over $Na_2SO_4$. The solvent was evaporated under reduced pressure and the residue was purified by flash chromatography (eluent, DCM: MeOH=20:1) to afford 7-(4-chlorophenyl)-1-methyl-6,7-dihydro-5H-benzo[f][1,2,3]triazolo[1,5-d][1,4]diazepine-9-carbaldehyde (30 mg, 68%) as yellow oil.

LCMS (Method B): 2.75 min m/z $[MH]^+$=339.1.

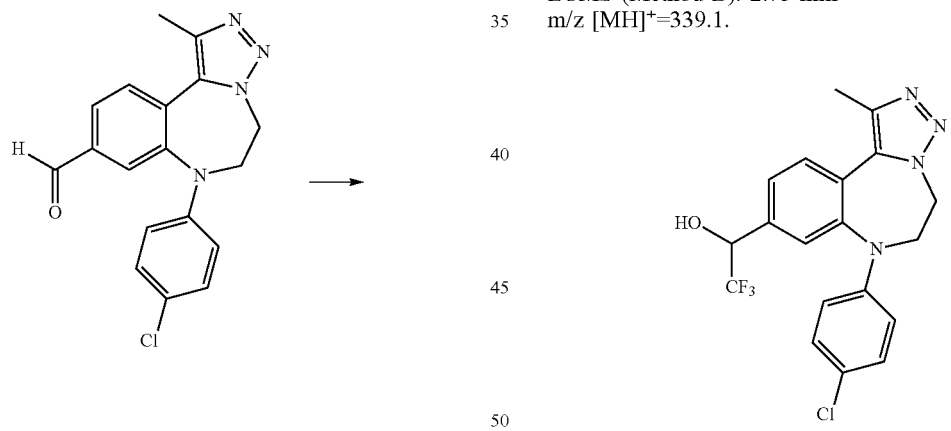

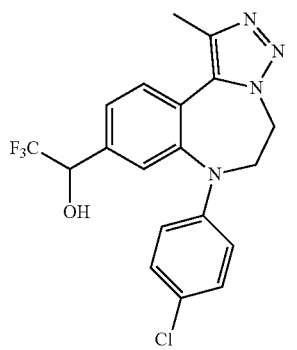 [SMILES: Cc1nnn2c1-c1ccc(C(O)C(F)(F)F)cc1N(c1ccc(Cl)cc1)CC2]

Step 2: 1-(7-(4-Chlorophenyl)-1-methyl-6,7-dihydro-5H-benzo[f][1,2,3]triazolo[1,5-d][1,4]diazepin-9-yl)-2,2,2-trifluoroethanol A solution of 7-(4-chlorophenyl)-1-methyl-6,7-dihydro-5H-benzo[f][1,2,3]triazolo[1,5-d][1,4]diazepine-9-carbaldehyde (60 mg, 0.18 mmol) and trimethyl(trifluoromethyl)silane (32 mg, 0.23 mmol) in anhydrous DCM (8 mL) was cooled at −78° C., and then a solution of tetrabutylammonium fluoride in THF (1 M, 0.1 mL) was added and the mixture was stirred overnight. The reaction was quenched with water and the aqueous layer extracted with ethyl acetate, dried over $Na_2SO_4$ and concentrated under reduced pressure. The residue was purified by flash chromatography (petroleum ether:ethyl acetate=5:1) to afford 1-(7-(4-chlorophenyl)-1-methyl-6,7-dihydro-5H-benzo[f][1,2,3]triazolo[1,5-d][1,4]diazepin-9-yl)-2,2,2-trifluoroethanol (20 mg, 27%) as yellow solid.

LCMS (Method B): 2.87 min m/z [MH]$^+$=409.1.

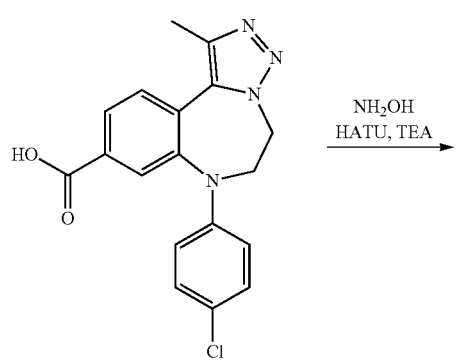

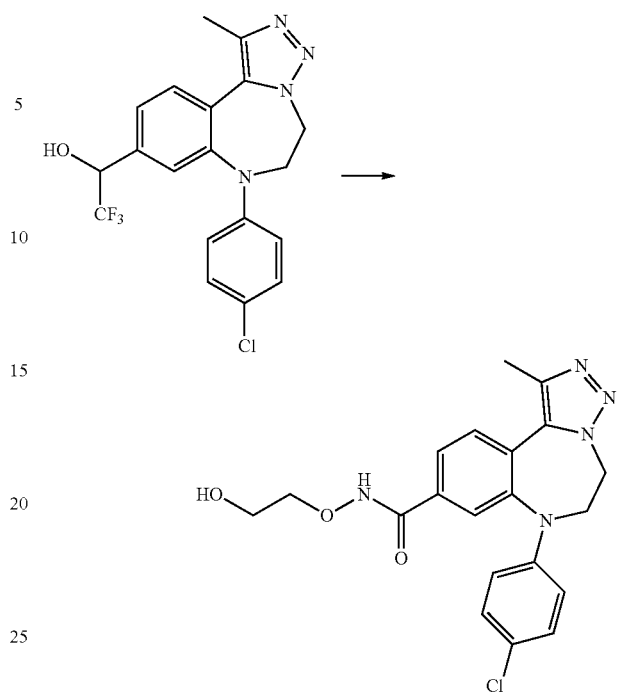

7-(4-Chlorophenyl)-N-(2-hydroxyethoxy)-1-methyl-6,7-dihydro-5H-benzo[f][1,2,3]triazolo[1,5-d][1,4]diazepine-9-carboxamide To a solution of 7-(4-chlorophenyl)-1-methyl-6,7-dihydro-5H-benzo[f][1,2,3]triazolo[1,5-d][1,4]diazepine-9-carboxylic acid (55.6 mg, 0.157 mmol) in THF (4 mL) was added HATU (89.4 mg, 0.235 mmol) at 0° C. and the reaction mixture was stirred for 30 min. Triethylamine (47.4 mg, 0.470 mmol) and 2-(aminooxy)ethanol (18.1 mg, 0.235 mmol) were then added. The resulting mixture was stirred at RT overnight and partitioned between water and DCM. The organics was extracted with DCM (3×20 mL) and the combined organic layer were washed with brine (2×30 mL), dried and concentrated under reduced pressure. The crude product was purified by preparative TLC (DCM: MeOH=10:1) to give 7-(4-chlorophenyl)-N-(2-hydroxyethoxy)-1-methyl-6,7-dihydro-5H-benzo[f][1,2,3]triazolo[1,5-d][1,4]diazepine-9-carboxamide (18 mg, 28%) as a yellow solid.

LCMS (Method B): RT 2.48 min m/z 414.1 [M+H]$^+$

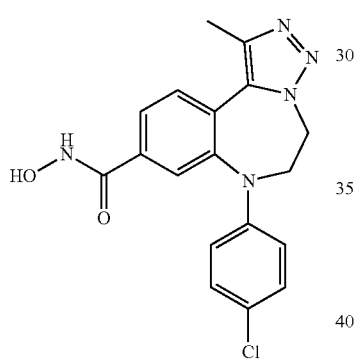

7-(4-Chlorophenyl)-N-hydroxy-1-methyl-6,7-dihydro-5H-benzo[f][1,2,3]triazolo[1,5-d][1,4]diazepine-9-carboxamide To a solution of 7-(4-chlorophenyl)-1-methyl-6,7-dihydro-5H-benzo[f][1,2,3]triazolo[1,5-d][1,4]diazepine-9-carboxylic acid (93.1 mg, 0.26 mmol) in THF (4 mL) was added HATU (149.7 mg, 0.394 mmol) at 0° C. and the reaction mixture was stirred for 30 min. Triethylamine (79.6 mg, 0.788 mmol) and hydroxylamine hydrochloride (27.4 mg, 0.394 mmol) were then added. The resulting mixture was stirred at RT overnight and partitioned between water and DCM. The organics was extracted with DCM (3×20 mL) and the combined organic layer were washed with brine (2×30 mL), dried and concentrated under reduced pressure. The crude product was purified by preparative TLC (DCM: MeOH=10:1) to give 7-(4-chlorophenyl)-N-hydroxy-1-methyl-6,7-dihydro-5H-benzo[f][1,2,3]triazolo[1,5-d][1,4]diazepine-9-carboxamide (20 mg, 21%) as a yellow solid.

LCMS (Method B): RT 2.40 min m/z 370.3 [M+H]$^+$.

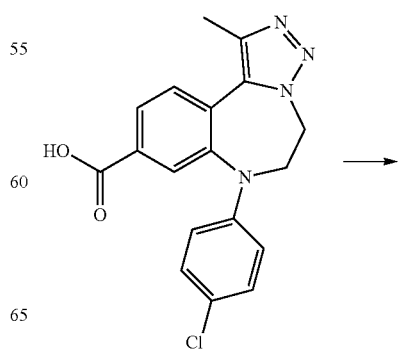

-continued

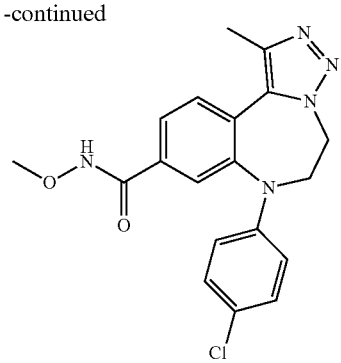

7-(4-chlorophenyl)-N-methoxy-1-methyl-6,7-di-hydro-5H-benzo[f][1,2,3]triazolo[1,5-d][1,4]diazepine-9-carboxamide To a solution of 7-(4-chlorophenyl)-1-methyl-6,7-dihydro-5H-benzo[f][1,2,3]triazolo[1,5-d][1,4]diazepine-9-carboxylic acid (81.1 mg, 0.229 mmol) in DCM (4 mL) was added HATU (130.4 mg, 0.343 mmol) at 0° C. and the mixture was stirred for 30 min. To the mixture was added triethylamine (69.3 mg, 0.686 mmol) and O-methylhydroxylamine hydrochloride (28.6 mg, 0.343 mmol). The resulting mixture was stirred at RT overnight and partitioned between water and DCM. The organics was extracted with DCM (3×20 mL) and the combined organic layer were washed with brine (2×30 mL), dried and concentrated under reduced pressure. The crude product was purified by preparative TLC (DCM: MeOH=10:1) to give 7-(4-chlorophenyl)-N-methoxy-1-methyl-6,7-dihydro-5H-benzo[f][1,2,3]triazolo[1,5-d][1,4]diazepine-9-carboxamide (30 mg, 34%) as a yellow solid.

LCMS (Method B): RT 2.55 min
m/z 384.1 [M+H]$^+$.

General Method for the Amidation Reaction

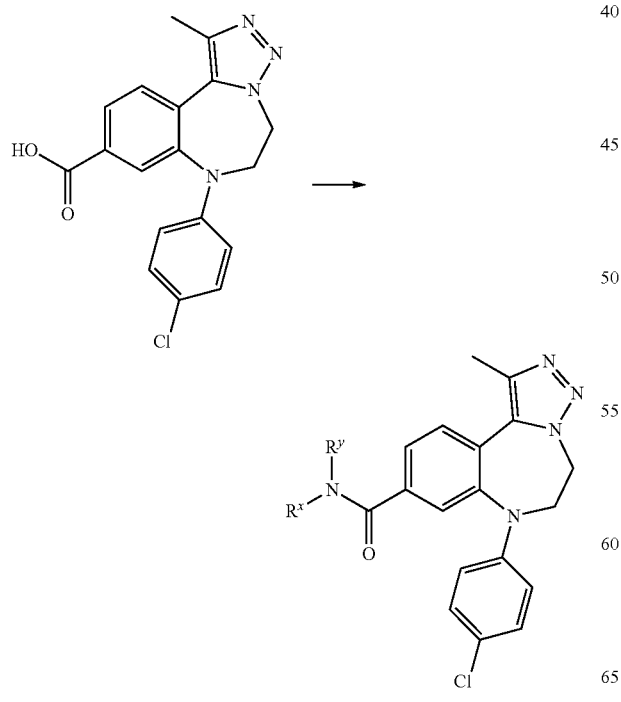

7-(4-Chlorophenyl)-1-methyl-6,7-dihydro-5H-benzo[f][1,2,3]triazolo[1,5-d][1,4]diazepine-9-carboxylic acid (0.1 mmol), TEA (0.3 mmol) and HATU (0.2 mmol) were combined and dissolved in DCM (2 mL). The reaction mixture was stirred at RT for 20 min and a solution of amine (0.2 mmol) in DCM (0.5 mL) was added. The reaction mixture was stirred at RT for 16 h or upon completion (assessed by HPLC). A saturated aqueous solution of NH$_4$Cl was added and the organics were separated, and concentrated under reduced pressure. The crude oil was purified by preparative HPLC to afford the titled compound.

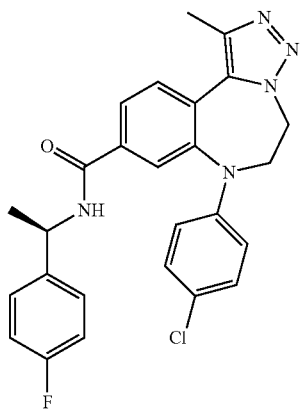 [SMILES: Cc1nnn2c1-c1ccc(C(=O)N[C@H](C)c3ccc(F)cc3)cc1N(c1ccc(Cl)cc1)CC2]

7-(4-chlorophenyl)-N—((R)-1-(4-fluorophenyl)ethyl)-1-methyl-6,7-dihydro-5H-benzo[f][1,2,3]triazolo[1,5-d][1,4]diazepine-9-carboxamide LCMS (Method A): 6.53 min
m/z [MH]$^+$=476.25.

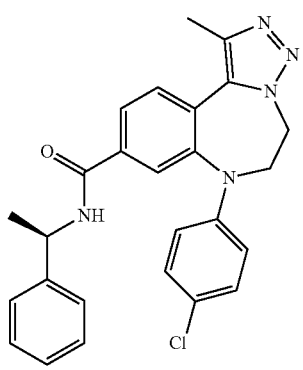 [SMILES: Cc1nnn2c1-c1ccc(C(=O)N[C@H](C)c3ccccc3)cc1N(c1ccc(Cl)cc1)CC2]

7-(4-chlorophenyl)-1-methyl-N—((R)-1-phenylethyl)-6,7-dihydro-5H-benzo[f][1,2,3]triazolo[1,5-d][1,4]diazepine-9-carboxamide LCMS (Method A): 5.55 min
m/z [MH]$^+$=458.0

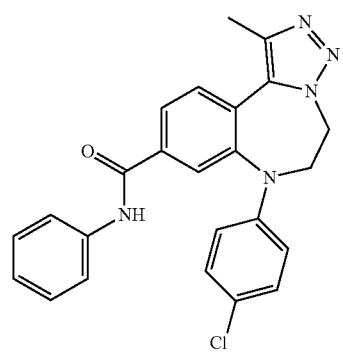 [SMILES: Cc1nnn2c1-c1ccc(C(=O)Nc3ccccc3)cc1N(c1ccc(Cl)cc1)CC2]

7-(4-chlorophenyl)-1-methyl-N-phenyl-6,7-dihydro-5H-benzo[f][1,2,3]triazolo[1,5-d][1,4]diazepine-9-carboxamide LCMS (Method A): 5.60 min
m/z [MH]$^+$=430.1

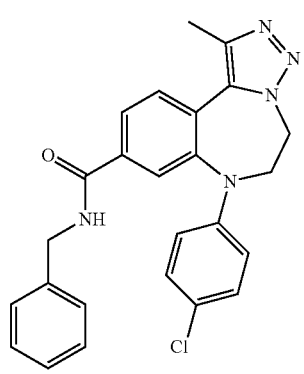 [SMILES: Cc1nnn2c1-c1ccc(C(=O)NCc3ccccc3)cc1N(c1ccc(Cl)cc1)CC2]

N-benzyl-7-(4-chlorophenyl)-1-methyl-6,7-dihydro-5H-benzo[f][1,2,3]triazolo[1,5-d][1,4]diazepine-9-carboxamide LCMS (Method A): 5.49 min
m/z [MH]$^+$=444.0

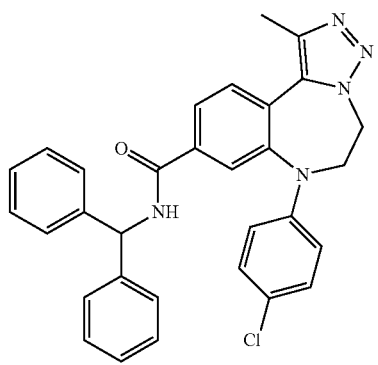 [SMILES: Cc1nnn2c1-c1ccc(C(=O)NC(c3ccccc3)c3ccccc3)cc1N(c1ccc(Cl)cc1)CC2]

N-benzhydryl-7-(4-chlorophenyl)-1-methyl-6,7-dihydro-5H-benzo[f][1,2,3]triazolo[1,5-d][1,4]diazepine-9-carboxamide LCMS (Method A): 5.49 min
m/z [MH]$^+$=444.0

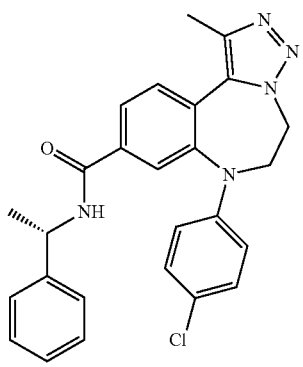 [SMILES: Cc1nnn2c1-c1ccc(C(=O)N[C@@H](C)c3ccccc3)cc1N(c1ccc(Cl)cc1)CC2]

7-(4-chlorophenyl)-1-methyl-N—((S)-1-phenylethyl)-6,7-dihydro-5H-benzo[f][1,2,3]triazolo[1,5-d][1,4]diazepine-9-carboxamide LCMS (Method A): 5.56 min
m/z [MH]$^+$=458.0

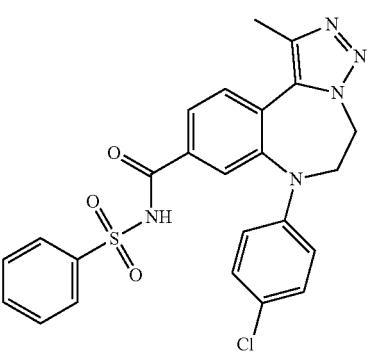 [SMILES: Cc1nnn2c1-c1ccc(C(=O)NS(=O)(=O)c3ccccc3)cc1N(c1ccc(Cl)cc1)CC2]

7-(4-chlorophenyl)-1-methyl-N-(phenylsulfonyl)-6,7-dihydro-5H-benzo[f][1,2,3]triazolo[1,5-d][1,4]diazepine-9-carboxamide LCMS (Method A): 5.60 min
m/z [MH]$^+$=494.0

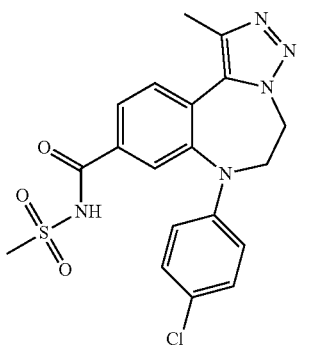 [SMILES: Cc1nnn2c1-c1ccc(C(=O)NS(C)(=O)=O)cc1N(c1ccc(Cl)cc1)CC2]
7-(4-chlorophenyl)-1-methyl-N-(methylsulfonyl)-6,
7-dihydro-5H-benzo[f][1,2,3]triazolo[1,5-d][1,4]
diazepine-9-carboxamide
LCMS (Method A): 5.56 min
m/z [MH]⁺=430.1
| Example | Structure | 1H-NMR |
|---|---|---|
| 1 | 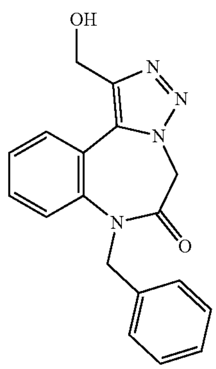 [SMILES: O=C1Cn2nnc(CO)c2-c2ccccc2N1Cc1ccccc1] | (600 MHz, CD$_3$OD): δ 7.28 (dt, J = 17.7, 8.4 Hz, 4H), 7.19-7.16 (m, 2H), 7.08 (d, J = 7.3 Hz, 1H), 6.69 (t, J = 7.4 Hz, 1H), 6.60 (d, J = 8.3 Hz, 1H), 4.76 (q, J = 18.0 Hz, 2H), 4.54 (q, J = 17.2 Hz, 2H), 4.28 (s, 2H). |
| 2 | 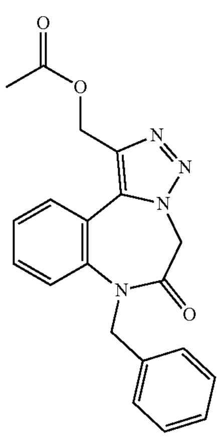 [SMILES: CC(=O)OCc1nnn2c1-c1ccccc1N(Cc1ccccc1)C(=O)C2] | (600 MHz, CDCl$_3$): δ 7.56 (dd, J = 7.8, 0.9 Hz, 1H), 7.49-7.45 (m, 2H), 7.37-7.34 (m, 1H), 7.16 (dt, J = 3.1, 1.6 Hz, 3H), 6.90-6.88 (m, 2H), 5.52 (d, J = 14.2 Hz, 1H), 5.42 (d, J = 12.9 Hz, 1H), 5.23 (d, J = 15.5 Hz, 1H), 5.04 (d, J = 12.9 Hz, 1H), 4.88 (d, J = 15.5 Hz, 1H), 4.64 (d, J = 14.2 Hz, 1H), 2.07 (s, 3H). |

| Example | Structure | 1H-NMR |
|---|---|---|
| 3 | 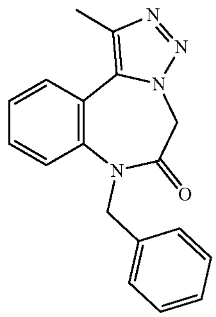 [SMILES: Cc1nnn2c1-c1ccccc1N(Cc1ccccc1)C(=O)C2] | (600 MHz, CDCl₃): δ 7.46-7.43 (m, 3H), 7.35-7.33 (m, 1H), 7.18-7.16 (m, 3H), 6.90 (dd, J = 6.4, 2.4 Hz, 2H), 5.47 (d, J = 14.1 Hz, 1H), 5.19 (d, J = 15.5 Hz, 1H), 4.90 (d, J = 15.5 Hz, 1H), 4.62 (d, J = 14.1 Hz, 1H), 2.46 (s, 3H). |
| 4 | 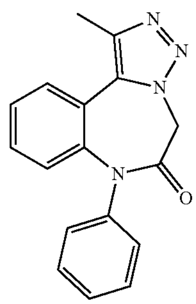 [SMILES: Cc1nnn2c1-c1ccccc1N(c1ccccc1)C(=O)C2] | |
| 5 | 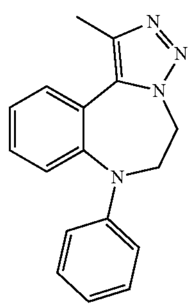 [SMILES: Cc1nnn2c1-c1ccccc1N(c1ccccc1)CC2] | (400 MHz, Chloroform-d) δ ppm 2.55 (s, 3 H) 4.17 (t, J = 6.0 Hz 2 H) 4.63 (t, J = 6.0 Hz 2 H) 6.73 (dd, J = 8.8 Hz 2 H) 6.86 (m, 1 H) 7.18 (m, 2 H) 7.35 (m, 3 H) 7.52 (dd, J = 8.4 Hz 1 H). |
| 6 | 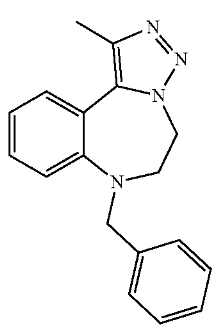 [SMILES: Cc1nnn2c1-c1ccccc1N(Cc1ccccc1)CC2] | (600 MHz, CDCl₃): δ 7.41-7.38 (m, 1H), 7.36-7.31 (m, 1H), 7.30-7.22 (m, 3H), 7.18-7.12 (m, 2H), 7.11-7.07 (m, 1H), 4.51-4.47 (m, 2H), 4.40-4.38 (m, 1H), 3.58-3.56 (m, 2H), 2.53 (s, 3H). |

| Example | Structure | 1H-NMR |
|---|---|---|
| 7 | 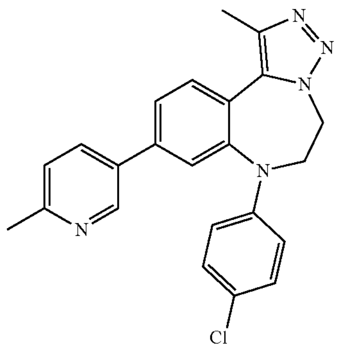 [SMILES: Cc1ccc(-c2ccc3c(c2)N(c2ccc(Cl)cc2)CCn2nnc(C)c2-3)cn1] | (400 MHz, CD$_3$OD) δ ppm 2.52 (s, 3 H) 2.57 (s, 3 H) 4.18 (t, J = 6.0 Hz 2 H), 4.5-5.5 (m, 2 H, covered by water) 6.75 (dd, J = 6.8, 2.0 Hz, 2 H) 7.14 (dd, J = 6.8, 2.0 Hz, 2 H) 7.38 (d, J = 8.0 Hz, 1 H) 7.53 (d, J = 2.0 Hz, 1 H) 7.73 (dd, J = 8.0, 1.6 Hz, 1 H) 7.78 (d, J = 8.0 Hz, 1 H) 7.96 (dd, J = 8.0, 2.8 Hz, 1 H) 8.59 (d, J = 2.0 Hz, 1 H). |
| 8 | 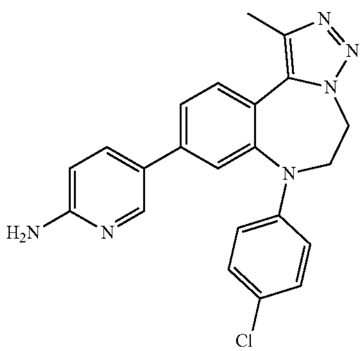 [SMILES: Cc1nnn2c1-c1ccc(-c3ccc(N)nc3)cc1N(c1ccc(Cl)cc1)CC2] | (400 MHz, CD$_3$OD) δ ppm 2.50 (s, 3 H) 4.14 (t, J = 6.0 Hz 2 H) 4.67(t, J = 6.0 Hz 2 H) 6.75 (dd, J = 6.8 Hz, 2.0 Hz 2 H) 7.10 (d, J = 9.6 Hz 1 H) 7.15 (dd, J = 6.8 Hz, 2.0 Hz 2 H) 7.55 (d, J = 8.00 Hz 1 H) 7.65 (d, J = 2.00 Hz 1 H) 7.75 (d, J = 2.00 Hz 1 H) 8.07 (d, J = 1.60 Hz 1 H) 8.20 (dd, J = 9.6 Hz, 2.4 Hz 1 H). |
| 9 | 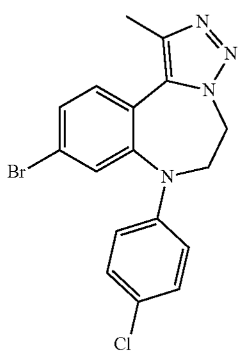 [SMILES: Cc1nnn2c1-c1ccc(Br)cc1N(c1ccc(Cl)cc1)CC2] | (400 MHz, CD$_3$OD) δ ppm 2.49 (s, 3 H) 4.14 (t, J = 6.0 Hz 2 H) 4.67 (t, J = 6.0 Hz 2 H) 6.77 (dd, J = 6.8 Hz, 2.0 Hz 2 H) 7.20 (dd, J = 6.8 Hz, 2.0 Hz 2 H) 7.42 (s, 1 H) 7.56 (d, J = 1.6 Hz 2 H). |
| 10 | 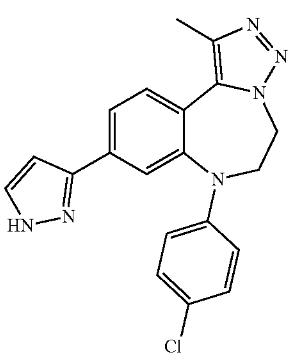 [SMILES: Cc1nnn2c1-c1ccc(-c3cc[nH]n3)cc1N(c1ccc(Cl)cc1)CC2] | (400 MHz, CD$_3$OD) δ ppm 2.53 (s, 3 H) 4.19 (t, J = 6.0 Hz 2 H) 4.69 (t, J = 6.0 Hz 2 H) 6.69 (d, J = 2.4 Hz 1 H) 6.76 (d, J = 9.2 Hz 2 H) 7.15 (d, J = 9.2 Hz 2 H) 7.69 (d, J = 2.4 Hz 1 H) 7.71 (s, 1 H) 7.77 (d, J = 2.4 Hz 1 H) 7.86 (dd, J = 8 Hz, 2 Hz 1 H). |

-continued
| Example | Structure | 1H-NMR |
|---|---|---|
| 11 | 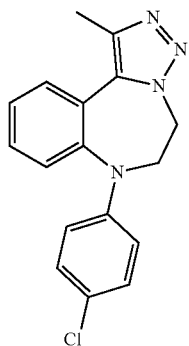 [SMILES: Cc1nnn2c1-c1ccccc1N(c1ccc(Cl)cc1)CC2] | (400 MHz, CD₃OD) δ ppm 2.49 (s, 3 H) 4.14 (t, J = 6.0 Hz 2 H) 4.64 (t, J = 6.0 Hz 2 H) 6.77 (d, J = 9.2 Hz, 2 H) 7.12 (d, J = 9.2 Hz, 2 H) 7.33 (dd, J = 8.0 Hz, 2.0 Hz 1 H) 7.47 (m, 2 H) 7.65 (dd, J = 8.0 Hz, 2.0 Hz 1 H). |
| 12 | 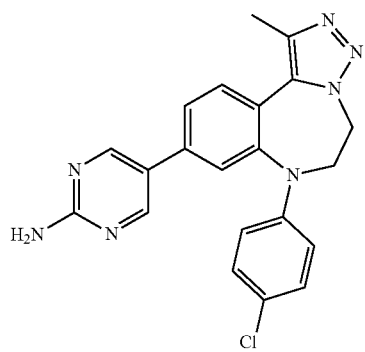 [SMILES: Cc1nnn2c1-c1ccc(-c3cnc(N)nc3)cc1N(c1ccc(Cl)cc1)CC2] | (400 MHz, Chloroform-d) δ ppm 2.60 (s, 3 H) 4.19 (t, J = 6.0 Hz 2 H) 4.69 (t, J = 6.0 Hz 2 H) 6.74 (d, J = 8.8 Hz 2 H) 7.19 (d, J = 8.8 Hz 2 H) 7.37 (d, J = 1.6 Hz 1 H) 7.44 (dd, J = 8 Hz 2 Hz 1 H) 7.50 (br s 2 H) 7.67 (d, J = 8.0 Hz 1 H) 8.55 (s, 2 H). |
| 13 | 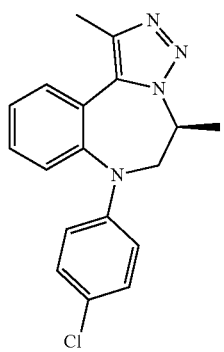 [SMILES: Cc1nnn2c1-c1ccccc1N(c1ccc(Cl)cc1)C[C@@H]2C] | (400 MHz, Chloroform-d) δ ppm 1.83 (d, J = 6.4 Hz 3 H) 2.53 (s, 3 H) 3.77 (t, J = 11.6 Hz 1 H) 4.14 (dd, J = 12.0 Hz 4.0 Hz 1 H) 4.66 (m, 1 H) 6.65 (d, J = 8.4 Hz 2 H) 7.12 (d, J = 8.4 Hz 2 H) 7.26-7.39 (m, 3 H) 7.52 (d, J = 7.2 Hz 1 H) |
| 14 | 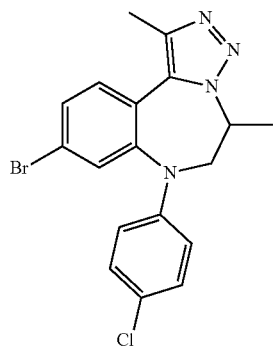 [SMILES: Cc1nnn2c1-c1ccc(Br)cc1N(c1ccc(Cl)cc1)CC2C] | ¹H NMR (400 MHz, Chloroform-d) δ ppm 1.83 (d, J = 6.7 Hz, 1H), 2.52 (s, 1H), 3.76 (m, 1H), 4.14 (dd, J = 12.1, 4.2 Hz, 0H), 4.67 (m, 1H), 6.73 (d, J = 9.0 Hz, 1H), 7.19 (d, J = 9.0 Hz, 1H), 7.39 (m, 1H), δ 7.45 (dd, J = 8.3, 1.9 Hz, 1H). |

-continued

| Example | Structure | 1H-NMR |
|---|---|---|
| 15 | 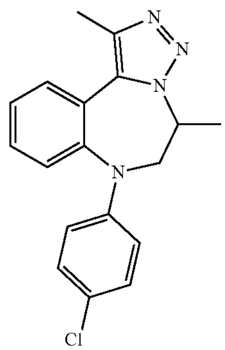 [SMILES: Cc1nnn2c1-c1ccccc1N(c1ccc(Cl)cc1)CC2C] | ¹H NMR (400 MHz, Chloroform-d) δ ppm 1.88 (br s, 3 H) 2.75 (br s, 3 H) 3.88 (br s, 1 H) 4.24 (br s, 1 H) 4.79 (br s, 1 H) 7.71 (d, J = 8.0 Hz 2 H) 7.18 (d, J = 8.0 Hz 2 H) 7.35 (m, 1 H) 7.49-7.57 (m, 3 H) |
| 16 | 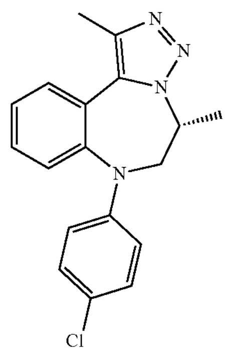 [SMILES: Cc1nnn2c1-c1ccccc1N(c1ccc(Cl)cc1)C[C@H]2C] | ¹H NMR (400 MHz, Methanol-d₄) δ ppm 1.77 (d, J = 6.8 Hz 3 H) 2.49 (s, 3 H) 3.78 (dd, J = 12.4, 11.2 Hz 1 H) 4.26 (dd, J = 12.4, 4.8 Hz 1 H) 4.76 (m, 1 H) 6.73 (m, 2 H) 7.14 (m, 2 H) 7.30 (m, 1 H) 7.47 (m, 2 H) 7.66 (dd, J = 7.6, 1.6 Hz 1 H) |
| 17 | 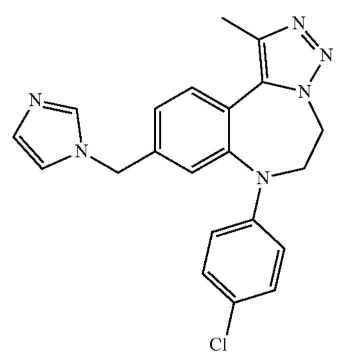 [SMILES: Cc1nnn2c1-c1ccc(Cn3ccnc3)cc1N(c1ccc(Cl)cc1)CC2] | ¹H NMR (400 MHz, CD₃OD) δ ppm 2.50 (s, 3 H) 4.15 (t, J = 6.0 Hz 2 H) 4.68 (t, J = 6.0 Hz 2 H) 5.46 (s, 2 H) 6.74 (d, J = 8.8 Hz, 2 H) 7.14 (d, J = 8.8 Hz, 2 H) 7.36 (d, J = 1.6 Hz, 1 H) 7.46 (dd, J = 8.0 Hz, 1.6 Hz 1 H) 7.61 (s, 1 H) 7.64 (s, 1 H) 7.72 (d, J = 8.0 Hz, 1 H) 9.05 (s, 1 H). |
| 18 | 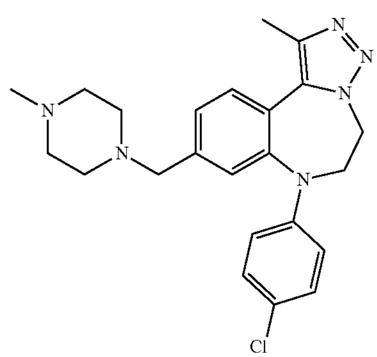 [SMILES: Cc1nnn2c1-c1ccc(CN3CCN(C)CC3)cc1N(c1ccc(Cl)cc1)CC2] | ¹H NMR (400 MHz, CD₃OD) δ ppm 2.50 (s, 3 H) 2.90 (s, 3 H) 3.00 (br, 4 H) 3.40 (br, 4 H) 3.80 (s, 2 H) 4.13 (t, J = 6.0 Hz 2 H) 4.66 (t, J = 6.0 Hz 2 H) 6.72 (d, J = 8.8 Hz, 2 H) 7.16 (d, J = 8.8 Hz, 2 H) 7.37 (s, 1 H) 7.46 (dd, J = 8.0 Hz, 1.2 Hz 1 H) 7.66 (d, J = 8.0 Hz, 1 H). |

| Example | Structure | 1H-NMR |
|---|---|---|
| 19 | 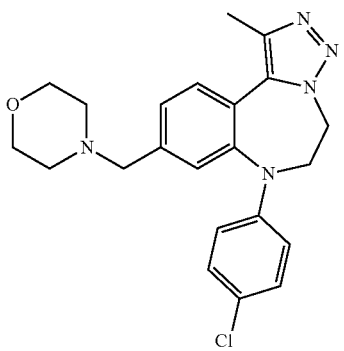 [SMILES: Cc1nnn2c1-c1ccc(CN3CCOCC3)cc1N(c1ccc(Cl)cc1)CC2] | (400 MHz, CD$_3$OD) δ ppm 2.52 (s, 3 H) 3.20 (s, 2 H) 3.37 (s, 2 H) 3.75 (s, 2 H) 4.06 (s, 2 H) 4.19 (t, J = 6.0 Hz 2 H) 4.36 (s, 2 H) 4.69 (t, J = 6.0 Hz 2 H) 6.79 (d, J = 7.2 Hz, 2 H) 7.18 (d, J = 7.2 Hz, 2 H) 7.46 (d, J = 1.2 Hz, 1 H) 7.55 (dd, J = 8.0 Hz, 1.6 Hz 1 H) 7.76 (d, J = 8.0 Hz, 1 H). |
| 20 | 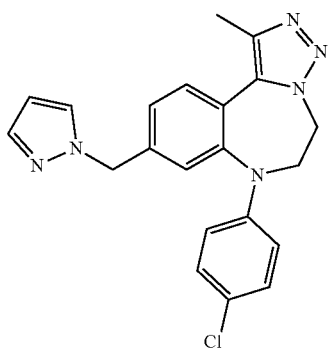 [SMILES: Cc1nnn2c1-c1ccc(Cn3cccn3)cc1N(c1ccc(Cl)cc1)CC2] | (400 MHz, CD$_3$OD) δ ppm 2.48 (s, 3 H) 4.13 (t, J = 6.0 Hz 2 H) 4.62 (t, J = 6.0 Hz 2 H) 5.37 (s, 2 H) 6.33 (t, J = 2.0 Hz 1 H) 6.69 (d, J = 6.8 Hz, 2 H) 7.12 (d, J = 6.8 Hz, 2 H) 7.26 (dd, J = 8.0 Hz, 1.6 Hz 1 H) 7.52 (d, J = 1.6 Hz, 1 H) 7.62 (d, J = 8.0 Hz, 1 H) 7.72 (d, J = 2.4 Hz, 1 H). |
| 21 | 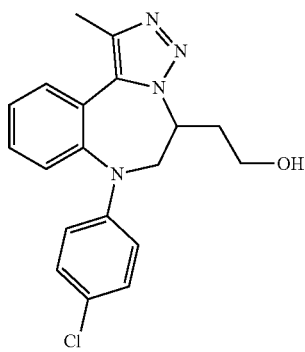 [SMILES: Cc1nnn2c1-c1ccccc1N(c1ccc(Cl)cc1)CC2CCO] | (400 MHz, Methanol-d$_4$) δ ppm 2.18 (m, 1 H) 2.47 (s, 3 H) 2.63 (m, 1 H) 3.71 (m, 2 H) 3.87 (dd, J = 12.40 Hz 10.8 Hz 1 H) 4.27 (dd, J = 12.40 Hz 5.2 Hz 1 H) 4.85 (m, 1 H, covered by water) 6.70 (m, 2 H) 7.12 (m, 2 H) 7.30 (dd, J = 8.00 Hz 5.2 Hz 1 H) 7.47 (m, 2 H) 7.63 (d, J = 7.60 Hz 1 H). |
| 22 | 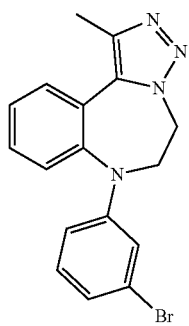 [SMILES: Cc1nnn2c1-c1ccccc1N(c1cccc(Br)c1)CC2] | (400 MHz, Chloroform-d) δ ppm 2.42 (s, 3 H), 4.11 (t, J = 6.0 Hz, 2 H), 4.59 (t, J = 6.0 Hz, 2 H), 6.63 (m, 1 H), 6.80 (d, J = 2.0 Hz, 1 H), 6.92 (d, J = 8.4 Hz, 1 H), 7.08 (t, J = 8.0 Hz, 1 H), 7.34 (m, 1 H), 7.49 (m, 2 H), 7.67 (dd, J = 7.5, 1.6 Hz, 1 H). |

| Example | Structure | 1H-NMR |
|---|---|---|
| 23 | 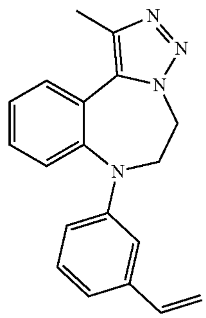 [SMILES: C=Cc1cccc(N2CCn3nnc(C)c3-c3ccccc32)c1] | (400 MHz, Chloroform-d) δ ppm 2.56 (s, 3 H), 4.18 (t, J = 6.0 Hz, 2 H), 4.64 (t, J = 6.0 Hz, 2 H), 5.22 (d, J = 11.0 Hz, 1 H), 5.66 (d, J = 17.6 Hz, 1 H), 6.62 (m, 2 H), 6.76 (s, 1 H), 6.94 (d, J = 7.6 Hz, 1 H), 7.14 (t, J = 7.9 Hz, 1 H), 7.38 (m, 3 H), 7.54 (m, 1H). |
| 24 | 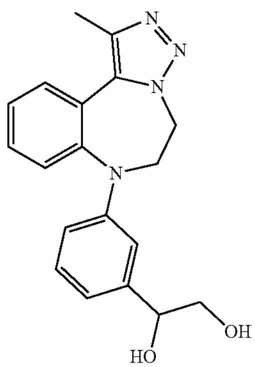 [SMILES: Cc1nnn2c1-c1ccccc1N(c1cccc(C(O)CO)c1)CC2] | (400 MHz, Chloroform-d) δ ppm 2.29 (s, 1 H), 2.53 (s, 3 H), 2.79 (s, 1 H), 3.62 (m, 1 H), 3.72 (m, 1 H), 4.17 (t, J = 6.0 Hz, 2 H), 4.62 (t, J = 6.0 Hz, 2 H), 4.73 (m, 1 H), 6.62 (dd, J = 8.0, 2.2 Hz, 1 H), 6.75 (s, 1 H), 6.80 (d, J = 8.0 Hz, 1 H), 7.14 (t, J = 8.0 Hz, 1 H), 7.37 (m, 3 H), 7.52 (dd, J = 7.4, 1.7 Hz, 1 H). |
| 25 | 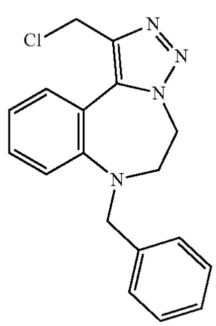 [SMILES: ClCc1nnn2c1-c1ccccc1N(Cc1ccccc1)CC2] | |
| 26 | 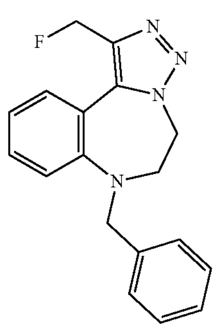 [SMILES: FCc1nnn2c1-c1ccccc1N(Cc1ccccc1)CC2] | (600 MHz, CDCl$_3$): δ 7.62 (dd, J = 7.6, 1.1 Hz, 1H), 7.40-7.37 (m, 1H), 7.29-7.23 (m, 4H), 7.18 (d, J = 8.2 Hz, 1H), 7.16-7.11 (m, 2H), 5.55 (d, J$_{H-F}$ = 49.4 Hz, 2H), 4.56 (t, J = 5.8 Hz, 2H), 4.41 (s, 2H), 3.62 (t, J = 5.8 Hz, 2H). |

-continued

| Example | Structure | 1H-NMR |
|---|---|---|
| 27 | 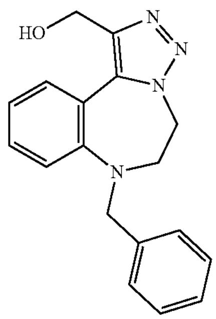 [SMILES: OCc1nnn2c1-c1ccccc1N(Cc1ccccc1)CC2] | (600 MHz, CDCl$_3$): δ 7.67 (dd, J = 7.7, 1.5 Hz, 1H), 7.42-7.39 (m, 1H), 7.31 (t, J = 7.3 Hz, 2H), 7.28-7.26 (m, 2H), 7.20-7.18 (m, 2H), 7.15-7.13 (m, 1H), 4.92 (s, 2H), 4.57 (t, J = 5.8 Hz, 2H), 4.44 (s, 2H), 3.63 (t, J = 5.8 Hz, 2H). |
| 28 | 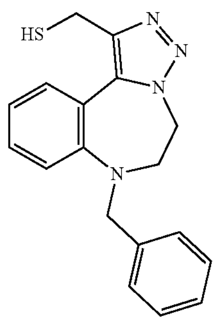 | (600 MHz, CDCl$_3$): δ 7.54 (dd, J = 7.6, 1.6 Hz, 1H), 7.37-7.34 (m, 1H), 7.26-7.24 (m, 3H), 7.21 (t, J = 7.2 Hz, 1H), 7.16 (d, J = 8.2 Hz, 1H), 7.13-7.10 (m, 2H), 4.50 (t, J = 6.0 Hz, 2H), 4.38 (s, 2H), 3.97 (d, J = 7.5 Hz, 2H), 3.59 (t, J = 5.9 Hz, 2H). |
| 29 | 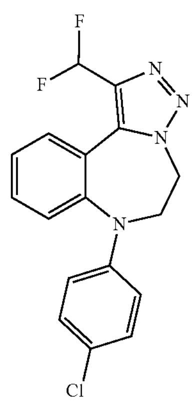 [SMILES: FC(F)c1nnn2c1-c1ccccc1N(c1ccc(Cl)cc1)CC2] | (400 MHz, DMSO-d$_6$) δ ppm 4.17 (t, J = 6.0 Hz 2 H) 4.67 (t, J = 6.0 Hz 2 H) 6.63 (dd, J = 6.8 Hz, 2.0 Hz 2 H) 6.88 (s, 0.4 H) 7.01 (s, 0.6 H) 7.14 (dd, J = 6.8 Hz, 2.4 Hz 2 H) 7.30 (d, J = 7.2 Hz 1 H) 7.40 (t, J = 7.6 Hz, 2.0 Hz 1 H) 7.48 (td, J = 7.6 Hz, 2.0 Hz 1 H) 7.75 (d, J = 7.0 Hz 1 H). |
| 30 | 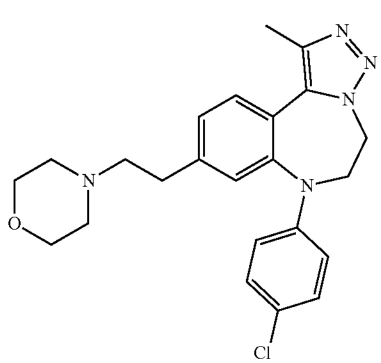 [SMILES: Cc1nnn2c1-c1ccc(CCN3CCOCC3)cc1N(c1ccc(Cl)cc1)CC2] | (400 MHz, DMSO-d$_6$) δ ppm 2.50 (s, 3 H) 2.66 (m, 6 H) 2.82 (m, 2 H) 3.77 (m, 4 H) 4.11 (t, J = 6.0 Hz 2 H) 4.61 (t, J = 6.0 Hz 2 H) 6.64 (d, J = 8.6 Hz 2 H) 7.13 (m, 3 H) 7.20 (dd, J = 7.9 Hz, 1.6 Hz 1 H) 7.44 (d, J = 8.0 Hz 1 H). |

-continued

| Example | Structure | 1H-NMR |
|---|---|---|
| 31 | 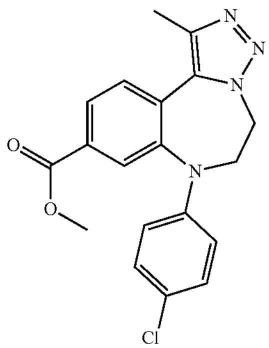 [SMILES: COC(=O)c1ccc2c(c1)N(c1ccc(Cl)cc1)CCn1nnc(C)c1-2] | (600 MHz, chloroform-d): δ ppm 2.53 (s, 3H), 3.89 (s, 3H), 4.12 (t, J = 6.1 Hz, 2H), 4.60 (t, J = 6.1 Hz, 2H), 6.62 (d, J = 9.1 Hz, 2H), 7.58 (d, J = 9.1 Hz, 2H), 7.92 (d, J = 8.1 Hz, 1H), 7.95 (d, J = 1.5 Hz, 1H), 7.97 (dd, J = 8.1 Hz and 1.5 Hz, 1H). |
| 32 | 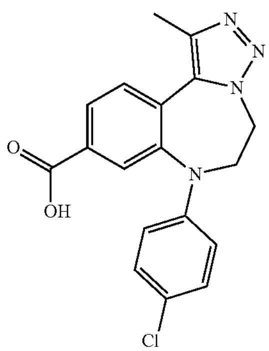 [SMILES: Cc1nnn2c1-c1ccc(C(=O)O)cc1N(c1ccc(Cl)cc1)CC2] | (600 MHz, MeOH-d4): δ ppm 2.50 (s, 3H), 4.15 (t, J = 6.1 Hz, 2H), 4.85 (t, J = 6.1 Hz, 2H), 6.73 (d, J = 9.1 Hz, 2H), 7.14 (d, J = 9.1 Hz, 2H), 7.70 (d, J = 7.7 Hz, 1H), 7.88 (d, J = 1.5 Hz, 1H), 7.99 (dd, J = 7.7 Hz and 1.5 Hz, 1H). |
| 33 | 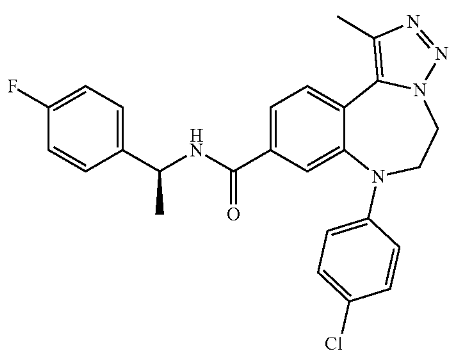 [SMILES: Cc1nnn2c1-c1ccc(C(=O)N[C@@H](C)c3ccc(F)cc3)cc1N(c1ccc(Cl)cc1)CC2] | (600 MHz, chloroform-d): δ ppm 1.58 (d, J = 6.96 Hz, 3H), 2.51 (s, 3H), 4.11 (t, J = 7.0 Hz, 2H), 4.61 (t, J = 7.0 Hz, 2H), 5.25 (q, J = 7.1 Hz, 1H), 6.26 (br s, 1H) 6.62 (d, J = 9.1 Hz, 2H), 7.02 (m, 2H) 7.12 (d, J = 9.1 Hz, 2H), 7.32 (m, 2H), 7.63 (dd, J = 8.1 Hz, J = 1.8 Hz 1H), 7.69 (d, J = 1.8 Hz, 1H). |
| 34 | 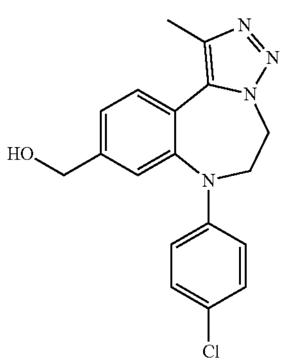 [SMILES: Cc1nnn2c1-c1ccc(CO)cc1N(c1ccc(Cl)cc1)CC2] | (600 MHz, chloroform-d): δ ppm 2.49 (s, 3H), 4.08 (t, J = 6.1 Hz, 2H), 4.57 (t, J = 6.1 Hz, 2H), 4.88 (s, 2H), 6.62 (d, J = 9.1 Hz, 2H), 7.09 (d, J = 9.1 Hz, 2H), 7.29 (s, 1H), 7.32 (d, J = 8.9 Hz, 1H), 7.47 (d, J = 8.9 Hz 1H). |

| Example | Structure | 1H-NMR |
|---|---|---|
| 35 | 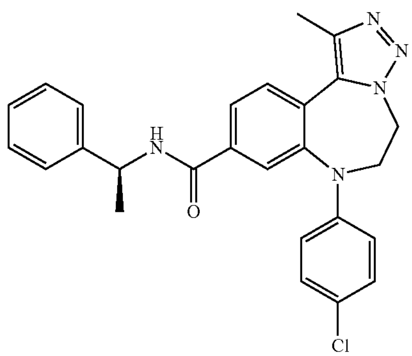 [SMILES: Cc1nnn2c1-c1ccc(C(=O)N[C@@H](C)c3ccccc3)cc1N(c1ccc(Cl)cc1)CC2] | (600 MHz, chloroform-d): δ ppm 1.58 (d, J = 6.9 Hz, 3H), 2.50 (s, 3H), 4.10 (t, J = 7.0 Hz, 2H), 4.58 (t, J = 7.0 Hz, 2H), 5.28 (q, J = 6.9 Hz, 1H), 6.28 (br s, 1H), 6.62 (d, J = 9.1 Hz, 2H), 7.12 (d, J = 9.1 Hz, 2H) 7.28 (m, 1H), 7.34-7.36 (m, 4H), 7.54 (d, J = 8.1 Hz, 1H), 7.69 (dd, J = 8.1 Hz, J = 1.7 Hz, 1H). 7.70 (d, J = 1.8 Hz, 1H) |
| 36 | 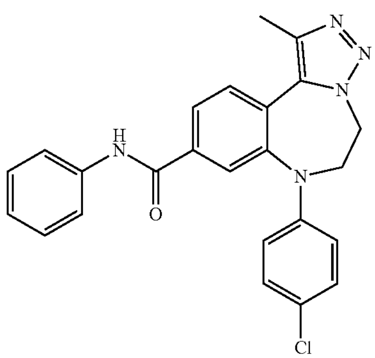 [SMILES: Cc1nnn2c1-c1ccc(C(=O)Nc3ccccc3)cc1N(c1ccc(Cl)cc1)CC2] | (600 MHz, chloroform-d): δ ppm 2.54 (s, 3H), 4.14 (t, J = 6.1 Hz, 2H), 4.62 (t, J = 6.1 Hz, 2H), 6.88 (d, J = 9.1 Hz, 2H) 7.14 (d, J = 9.1 Hz, 2H), 7.36 (m, 2H), 7.59 (d, J = 7.6 Hz 2H), 7.62 (d, J = 7.6 Hz 1H), 7.72 (br s, 1H) 7-76-7.79 (m, 2H). |
| 37 | 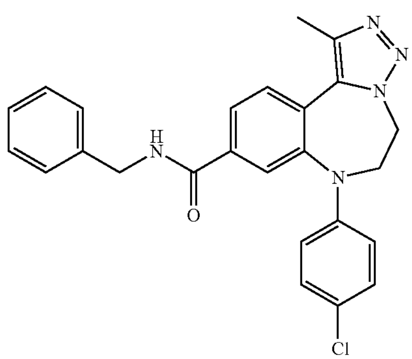 [SMILES: Cc1nnn2c1-c1ccc(C(=O)NCc3ccccc3)cc1N(c1ccc(Cl)cc1)CC2] | (600 MHz, chloroform-d): δ ppm 2.51 (s, 3H), 4.10 (t, J = 6.1 Hz, 2H), 4.57 (t, J = 6.1 Hz, 2H), 4.61 (br d, J = 5.7 Hz, 2H), 6.38 (br d, J = 5.7 Hz, 1H), 6.62 (d, J = 9.1 Hz, 2H) 7.11 (d, J = 9.1 Hz, 2H), 7.28-7.34 (m, 5H), 7.55 (d, J = 8.0 Hz, 1H), 7.69 (d, J = 8.0 Hz 1H), 7.71 (s, 1H). |
| 38 | 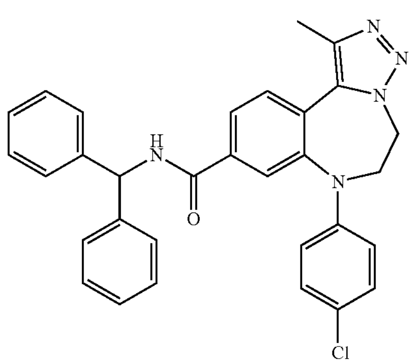 [SMILES: Cc1nnn2c1-c1ccc(C(=O)NC(c3ccccc3)c3ccccc3)cc1N(c1ccc(Cl)cc1)CC2] | (600 MHz, chloroform-d): δ ppm 2.50 (s, 3H), 4.11 (t, J = 6.1 Hz, 2H), 4.59 (t, J = 6.1 Hz, 2H), 6.39 (d, J = 9.1 Hz, 2H), 6.64 (d, J = 9.1 Hz, 2H), 7.11 (d, J = 9.1 Hz, 2H), 7.25-7.31 (m, 6H), 7.32-7.36 (m, 4H), 7.55 (d, J = 7.7 Hz 1H), 7.69 (dd, J = 7.7 Hz J = 1.7 Hz 1H), 7.75 (d, J = 1.7 Hz, 1H). |

| Example | Structure | 1H-NMR |
|---|---|---|
| 39 | 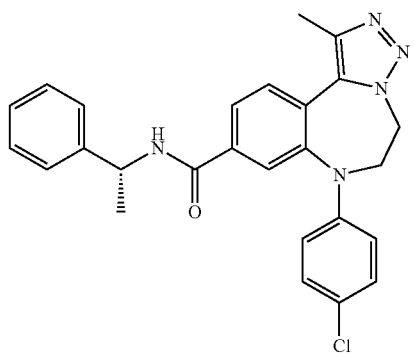 [SMILES: Cc1nnn2c1-c1ccc(C(=O)N[C@H](C)c3ccccc3)cc1N(c1ccc(Cl)cc1)CC2] | (600 MHz, chloroform-d): δ ppm 1.58 (d, J = 6.9 Hz, 3H), 2.50 (s, 3H), 4.10 (t, J = 7.0 Hz, 2H), 4.58 (t, J = 7.0 Hz, 2H), 5.28 (q, J = 6.9 Hz, 1H), 6.28 (br s, 1H), 6.62 (d, J = 9.1 Hz, 2H), 7.12 (d, J = 9.1 Hz, 2H) 7.28 (m, 1H), 7.34-7.36 (m, 4H), 7.54 (d, J = 8.1 Hz, 1H), 7.69 (dd, J = 8.1 Hz, J = 1.7 Hz, 1H). 7.70 (d, J = 1.8 Hz, 1H) |
| 40 | 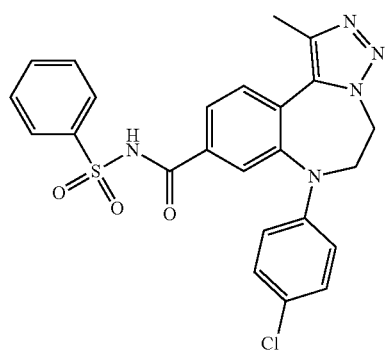 [SMILES: Cc1nnn2c1-c1ccc(C(=O)NS(=O)(=O)c3ccccc3)cc1N(c1ccc(Cl)cc1)CC2] | (400 MHz, chloroform-d) δ ppm 2.51 (s, 3 H), 4.09 (t, J = 6.1 Hz 2 H) 4.57 (t, J = 6.1 Hz 2 H), 6.61 (d, J = 8.9 Hz 2 H) 7.09 (d, J = 8.9 Hz 2 H) 7.54-7.58 (m, 3 H) 7.65-7.71 (m, 3 H), 8.11 (d, J = 8.1 Hz, 2H). |
| 41 | 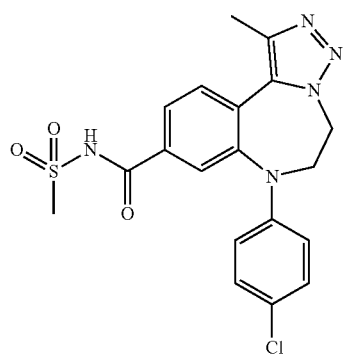 [SMILES: Cc1nnn2c1-c1ccc(C(=O)NS(C)(=O)=O)cc1N(c1ccc(Cl)cc1)CC2] | (400 MHz, chloroform-d) δ ppm 2.54 (s, 3 H) 3.38 (s, 3H), 4.13 (t, J = 6.0 Hz 2 H) 4.61 (t, J = 6.0 Hz 2 H), 6.65 (d, J = 8.8 Hz 2 H) 7.14 (d, J = 8.8 Hz 2 H) 7.62 (d, J = 8.0 Hz 1 H) 7.74-7.79 (m, 2 H). |
| 42 | 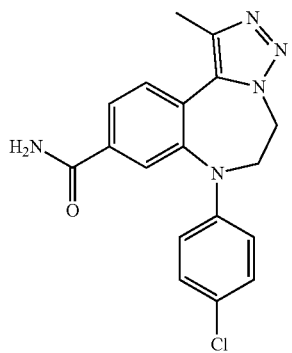 [SMILES: Cc1nnn2c1-c1ccc(C(N)=O)cc1N(c1ccc(Cl)cc1)CC2] | (400 MHz, CD$_3$OD) δ ppm 2.51 (s, 3 H) 4.16 (t, J = 6.0 Hz 2 H) 4.67 (t, J = 6.0 Hz 2 H) 6.73 (d, J = 8.8 Hz 2 H) 7.14 (d, J = 8.8 Hz 2 H) 7.74 (d, J = 8.0 Hz 1 H) 7.84 (d, J = 1.6 Hz 1 H) 7.91 (dd, J = 8.4, 2.0 Hz 1 H). |

| Example | Structure | 1H-NMR |
|---|---|---|
| 43 | 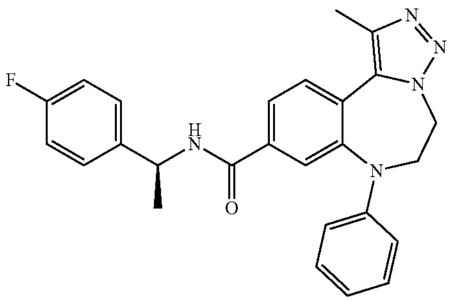 [SMILES: Cc1nnn2c1-c1ccc(C(=O)N[C@@H](C)c3ccc(F)cc3)cc1N(c1ccccc1)CC2] | (600 MHz, chloroform-d): δ ppm 1.57 (d, J = 6.96 Hz, 3H), 2.51 (s, 3H), 4.15 (t, J = 6.1 Hz, 2H), 4.61 (t, J = 6.1 Hz, 2H), 5.26 (q, J = 7.2 Hz, 2H), 6.18 (br s, 1H) 6.72 (d, J = 7.9 Hz, 2H), 6.87 (t, J = 7.4 Hz 1H) 7.02 (t, J = 8.7 Hz, 2H), 7.18 (t, J = 8.7 Hz 2H), 7.32 (dd, J = 5.1 Hz, J = 3.4 Hz 1H), 7.56 (d, J = 8.1 Hz, 1H), 7.64 (dd, J = 8.1 Hz, J = 1.6 Hz 1H), 7.70 (d, J = 1.6 Hz 1H). |
| 44 | 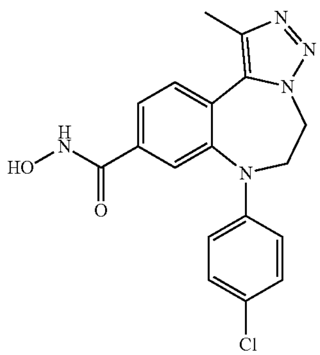 [SMILES: Cc1nnn2c1-c1ccc(C(=O)NO)cc1N(c1ccc(Cl)cc1)CC2] | (400 MHz, Methanol-d$_4$) δ 7.79-7.73 (m, 2H), 7.72 (s, 1H), 7.17 (d, J = 8.8 Hz, 2H), 6.75 (d, J = 8.8 Hz, 2H), 4.68 (m, 2H), 4.18 (m, 2H), 2.52 (s, 3H). |
| 45 | 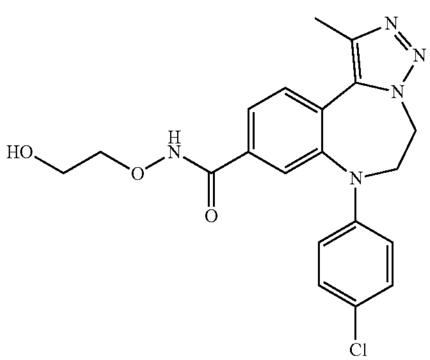 [SMILES: Cc1nnn2c1-c1ccc(C(=O)NOCCO)cc1N(c1ccc(Cl)cc1)CC2] | (400 MHz, CD3Cl) δ 7.74 (m, 1 H), 7.71 (s, 1H), 7.61 (d, J = 7.6 Hz, 1H), 7.16 (d, J = 8.8 Hz, 2H), 6.67 (d, J = 8.8 Hz, 2H), 4.63 (m, 2H), 4.15 (m, 2H), 4.09 (m, 2H), 3.80 (m, 2H), 3.50 (s, 1H), 2.55 (s, 3H). |
| 46 | 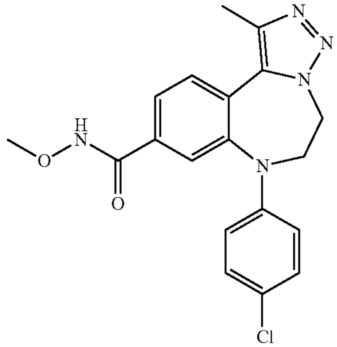 [SMILES: CONC(=O)c1ccc2c(c1)N(c1ccc(Cl)cc1)CCn1nnc(C)c1-2] | (400 MHz, CDCl$_3$) δ 7.74 (m, 2H), 7.58 (d, J = 8.0 Hz, 1H), 7.12 (d, J = 8.8 Hz, 2H), 6.65 (d, J = 8.8 Hz, 2H), 4.61 (t, J = 5.6 Hz, 2H), 4.14 (t, J = 5.6 Hz, 2H), 3.87 (s, 3H), 2.53 (s, 3H). |

| Example | Structure | 1H-NMR |
|---|---|---|
| 47 | 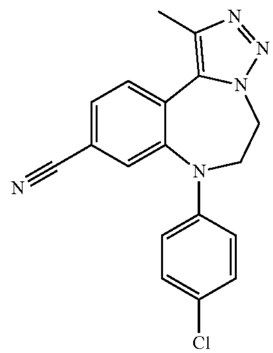 [SMILES: Cc1nnn2c1-c1ccc(C#N)cc1N(c1ccc(Cl)cc1)CC2] | (400 MHz, CDCl3) δ ppm 2.57 (s, 3 H) 4.16 (t, J = 6.0 Hz 2 H) 4.69 (t, J = 6.0 Hz 2 H) 6.75 (d, J = 8.8 Hz 2 H) 7.24 (d, J = 8.8 Hz 2 H) 7.53 (s, 1 H) 7.56 (d, J = 8.0 Hz 1 H) 7.63 (d, J = 8.0 Hz 1 H). |
| 48 | 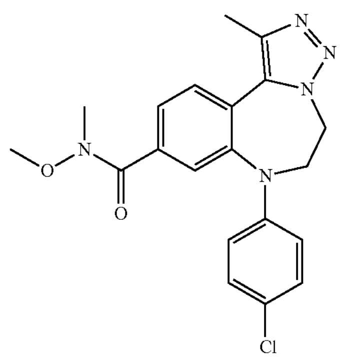 [SMILES: CON(C)C(=O)c1ccc2c(c1)N(c1ccc(Cl)cc1)CCn1nnc(C)c1-2] | (400 MHz, CDCl3) δ ppm 2.62 (s, 3H), 3.36 (s, 3H), 3.56 (s, 3H), 4.16 (br s, 2H), 4.66 (br s, 2H), 6.68 (d, J = 8.8 Hz, 2H), 7.15 (d, J = 8.8 Hz, 2H), 7.56-7.67 (m, 3H). |
| 49 | 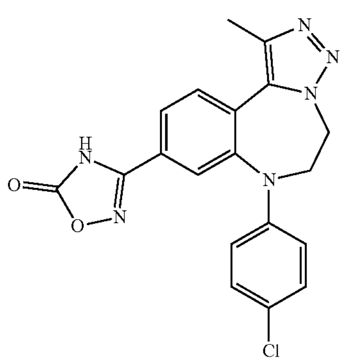 [SMILES: Cc1nnn2c1-c1ccc(-c3noc(=O)[nH]3)cc1N(c1ccc(Cl)cc1)CC2] | (400 MHz, DMSO-d6) δ ppm 2.54 (s, 3 H) 4.16 (t, J = 6.0 Hz 2 H) 4.67 (t, J = 6.0 Hz 2 H) 6.79 (d, J = 8.8 Hz 2 H) 7.24 (d, J = 8.8 Hz 2 H) 7.73 (d, J = 1.6 Hz 1 H) 7.81 (dd, J = 8.4, 1.6 Hz 1 H) 7.87 (d, J = 8.4 Hz 1 H). |
| 50 | 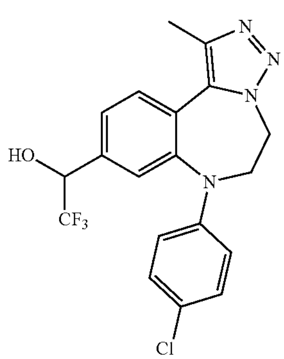 [SMILES: Cc1nnn2c1-c1ccc(C(O)C(F)(F)F)cc1N(c1ccc(Cl)cc1)CC2] | (400 MHz, CDCl3) δ ppm 2.58 (s, 3H), 4.17 (t, J = 5.6 Hz, 2H), 4.64-4.68 (m, 2H), 5.01-5.06 (m, 1H), 6.67 (d, J = 8.8 Hz, 2H), 7.15 (d, J = 8.8 Hz, 2H), 7.44 (s, 1H), 7.47(d, J = 8.0 Hz, 1H), 7.57 (d, J = 8.0 Hz, 1H). |

| Example | Structure | 1H-NMR |
|---|---|---|
| 51 | 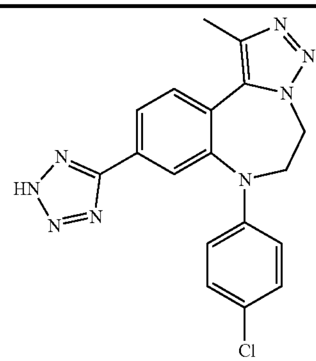 | (400 MHz, DMSO-$d_6$) δ ppm 2.47 (s, 3 H) 4.16 (t, J = 6.0 Hz 2 H) 4.67 (t, J = 6.0 Hz 2 H) 6.82 (d, J = 9.2 Hz 2 H) 7.24 (d, J = 9.2 Hz 2 H) 7.90 (d, J = 8.0 Hz 1 H) 7.96 (d, J = 1.6 Hz 1 H) 8.04 (dd, J = 8.0 Hz, 1.6 Hz 1 H). |

Biological Characterization

Assay Conditions

Binding Assay

BRD binding and inhibition was assessed by measuring the interaction of biotinylated acetyl-histone H4 peptide (Anaspec #64989) with the BRD target protein utilising AlphaScreen® technology (Perkin Elmer). In a white 384-well low volume plate (Greiner #784076), 100 nL of compound series in DMSO (0.5% final concentration) was added to the BRD target protein (80 nM final). After 30 min incubation at RT, H4 peptide was added to a final concentration of 2.5 nM. AlphaScreen streptavidin donor beads and AlphaScreen nickel chelate acceptor beads were added to a final concentration of 10 ug/mL each and allowed to incubate in a darkened environment for 1 h at RT. Plates were read on an EnVision plate reader (Perkin Elmer) and $IC_{50}$'s calculated using a four parameter non-linear curve fit.

These conditions are identical for all BRDs screened except BRD2D2 which uses 160 nM protein and 1.25 nM peptide.

Binding Affinity

| Example | BRD-2 (Domain 1) IC50 | BRD-2 (Domain 2) IC50 | BRD-3 (Domain 1) IC50 | BRD-4 (Domain 1) IC50 | BRD-4 (Domain 2) IC50 |
|---|---|---|---|---|---|
| 5 | B | A | A | A | A |
| 6 | C | C | ND | C | C |
| 7 | A | A | A | A | A |
| 8 | A | A | A | A | A |
| 10 | A | A | A | A | A |
| 11 | B | A | A | A | A |
| 12 | A | A | A | A | A |
| 13 | A | A | A | A | A |
| 16 | A | A | A | A | A |
| 20 | B | B | A | A | A |
| 21 | B | A | A | A | A |
| 22 | B | A | A | A | A |
| 23 | B | A | A | A | A |
| 24 | A | A | A | A | A |
| 29 | C | B | ND | B | B |
| 30 | B | B | B | B | B |
| 31 | B | A | A | A | A |
| 32 | B | A | A | A | A |
| 33 | A | A | A | A | A |
| 34 | B | A | A | A | A |
| 35 | A | A | A | A | A |
| 36 | A | A | A | A | A |
| 37 | B | A | A | A | A |
| 38 | B | A | A | A | A |
| 39 | A | A | A | A | A |
| 40 | A | A | A | A | A |
| 41 | A | A | ND | A | A |
| 42 | A | A | ND | A | A |
| 43 | A | A | ND | A | A |
| 44 | A | A | ND | A | A |
| 45 | A | A | ND | A | A |
| 46 | A | A | ND | A | A |
| 47 | A | A | ND | A | A |
| 48 | A | A | ND | A | A |
| 49 | A | A | ND | A | A |
| 50 | B | B | ND | A | A |
| 51 | A | A | ND | A | A |

Where A <100 nM;
B is 100 nM – 1 μM;
C is >1 μM;
ND = Not determined

Cell Proliferation Assay

The cells were prepared in the required fashion (suspension or adherent). The cells were initially washed once in the culture medium that they would be finally treated in. Following this 10 ml of the test medium was added and the cells. The mixture was pipetted gently several times.

The cells were counted and then the volume was spun down to the volume necessary for the total number of cells needed. The cells were then resuspended in the appropriate test medium to the desired concentration. In general, the final concentration of non-adherent cells was $2 \times 10^5$ cells/ml i.e. 10,000 cells per 50 μl. Once the desired concentration had been reached, 50 μl of the cells were added to the appropriate wells and the cells were incubated for 72 h at 37° C.

CellTiter-Glo Luminescent Assay (Kit G7571—See Promega's Instruction Manual for Additional Details):

Both reagents were pre-warmed to RT. The buffer was thawed in a 37° C. water bath until it had just completely thawed. It was then left on a bench at RT for at least 30 min.

Following this the substrate and buffer were mixed together. To ensure that the substrate was dissolved, the mixture was inverted several times.

The cell culture plates were removed from the incubator and were then allowed to adjust to RT for at least 30 min.

Afterwards 40 μL of the reagent was added to 100 μL of the culture medium. These were mixed on an orbital plate shaker for 2 min at RT, with due care to ensure that the media did not spill out of each well. The plates were then incubated for 10 min on the bench. The luminescence could then be read using a luminescence plate reader.

Cellular Activity

| Example | HL-60 IC$_{50}$ (μM) | MV4; 11 IC$_{50}$ (μM) |
|---|---|---|
| 7 | A | A |
| 8 | A | A |
| 10 | A | A |
| 11 | B | ND |
| 12 | A | ND |
| 13 | A | ND |
| 14 | A | ND |
| 16 | A | ND |
| 21 | B | ND |
| 22 | B | ND |
| 23 | B | ND |
| 24 | B | ND |
| 30 | B | ND |
| 31 | A | A |
| 32 | C | A |
| 35 | A | A |
| 36 | A | A |
| 39 | A | A |
| 40 | C | B |
| 41 | B | A |
| 43 | A | A |
| 45 | A | A |
| 46 | A | A |
| 49 | C | A |
| 51 | C | A |

Where A <1 μM;
B is 1 μM – 5 μm;
C is >5 μM;
ND = Not determined

In Vivo Assessment of Activity

Bone marrow and spleen cells are harvested from Eμ-myc mice as they become sick (enlarged spleen and lymph nodes). Single cell suspensions are prepared and one million BM cells are transplanted into each WT C57/BL6 mice by intravenous injection. Mice are administered daily doses of compound by intra-peritoneal injection starting from day 3. When mice become sick, they are euthanized and spleen and liver are weighed and examined by histology, Blood is taken for hematological analysis.

Hematological Analysis: Analysis of peripheral blood is performed by using an ADVIA 120 blood analyzer equipped with a mouse analysis software module (Bayer, Tarrytown, N.Y.).

Histological analysis: Spleens and livers from drug or vehicle treated mice are collected at sacrifice and stored in formalin. Paraffin-embedded sections and haematoxylin plus eosin (H&E) staining is performed. Photographs are taken on a Nikon Eclipse E600 microscope with ZEISS AxioCam MRC5 camera using Axiovision (Ver4.8) software.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A compound of Formula I or a pharmaceutically acceptable derivative, polymorph, salt or prodrug thereof

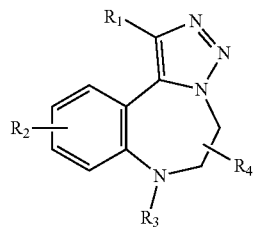

I wherein:

R$_1$ is selected from the group consisting of H, C$_{1-4}$alkyl, CF$_3$, CF$_2$H, C$_{1-4}$alkylXH, C$_{1-4}$alkylOCOR$_5$; wherein X=O, S;

R$_2$ is 0-3 substituents independently selected from the group consisting of C$_{1-4}$alkyl, CN, Cl, Br, I, C$_{3-10}$heterocyclyl, OC$_{1-4}$alkyl, C$_{5-10}$heteroaryl, C$_{1-4}$alkyl C$_{6-10}$aryl, C$_{1-4}$alkylC$_{5-10}$heteroaryl, hydroxyl, nitro, COR$_6$, CO$_2$R$_6$, CONR$_5$R$_6$, CONHSO$_2$R$_5$, SO$_2$NHCOR$_5$, CONR$_5$OR$_6$, C$_{1-4}$alkylNR$_5$R$_6$, C$_{1-4}$alkylOR$_6$, NR$_5$R$_6$, NR$_5$COR$_6$, NR$_7$CONR$_5$R$_6$ and NR$_5$CO$_2$R$_6$;

R$_3$ is selected from the group consisting of C$_{1-4}$alkyl, C$_{3-10}$cycloalkyl, C$_{3-10}$heterocyclyl, C$_{6-10}$aryl, C$_{1-4}$alkylC$_{6-10}$ aryl;

R$_4$ is 1 to 2 groups on the same or adjacent carbons selected from oxo, C$_{1-4}$alkyl, C$_{1-4}$alkylOH, C$_{1-4}$alkylOCOR$_5$, C$_{1-4}$alkylCONR$_5$R$_6$, C$_{1-4}$alkylC$_{6-10}$aryl, C$_{1-4}$alkylC$_{5-10}$heteroaryl;

R$_5$ and R$_6$ are independently selected from the group consisting of hydrogen, C$_{1-4}$alkyl, C$_{3-10}$cycloalkyl, C$_{3-10}$heterocyclyl, C$_{6-10}$aryl, C$_{5-10}$heteroaryl, C$_{1-4}$alkylC$_{6-10}$aryl and C$_{1-4}$alkylC$_{5-10}$heteroaryl;

alternatively R$_5$ and R$_6$ are bound to the same atom and form an optionally substituted ring that is 4 to 10 carbon atoms in size wherein optionally one or more carbon atoms are replaced with O, S, S(O), SO$_2$, or NR$_7$; and R$_7$ is selected from the group consisting of hydrogen and C$_{1-4}$alkyl and further wherein, unless otherwise stated, each alkyl, cycloalkyl, heterocycyl, heteroaryl, and aryl is optionally substituted.

2. A compound according to claim 1 of Formula II or a pharmaceutically acceptable derivative, polymorph, salt or prodrug thereof

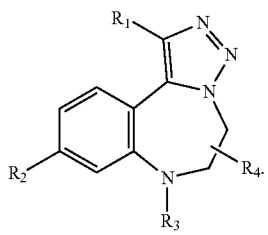

II

3. A compound according to claim 1 of Formula III or a pharmaceutically acceptable derivative, polymorph, salt or prodrug thereof

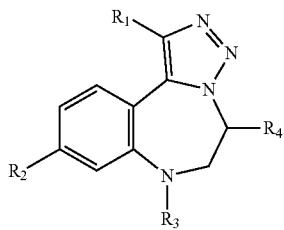

III provided that $R_4$ is limited to 0 to 1 groups.

4. A compound according to claim 1 or a pharmaceutically acceptable derivative, polymorph, salt or prodrug thereof wherein $R_1$ is selected from the group consisting of H or $C_{1-4}$alkyl;

$R_2$ is 0-3 substituents independently selected from the group consisting of $C_{1-4}$alkyl, CN, Cl, Br, I, $C_{3-10}$heterocyclyl, $OC_{1-4}$alkyl, $C_{5-10}$heteroaryl, $C_{1-4}$alkyl$C_{6-10}$aryl, $C_{1-4}$alkyl$C_{5-10}$heteroaryl, hydroxyl, nitro, $COR_6$, $CO_2R_6$, $CONR_5R_6$, $CONHSO_2R_5$, $SO_2NHCOR_5$, $CONR_5OR_6$, $C_{1-4}$alkyl$NR_5R_6$, $C_{1-4}$alkyl$OR_6$, $NR_5R_6$, $NR_5COR_6$, $NR_7CONR_5R_6$, and $NR_5CO_2R_6$;

$R_3$ is $C_{6-10}$aryl;

$R_4$ is 0 to 2 groups on the same or adjacent carbons selected from $C_{1-4}$alkyl, $C_{1-4}$alkylOH, $C_{1-4}$alkylO-$COR_5$, $C_{1-4}$alkyl$CONR_5R_6$, $C_{1-4}$alkyl$C_{6-10}$aryl, $C_{1-4}$alkyl$C_{5-10}$heteroaryl;

$R_5$ and $R_6$ are independently selected from the group consisting of hydrogen, $C_{1-4}$alkyl, $C_{3-10}$cycloalkyl, $C_{3-10}$heterocyclyl, $C_{6-10}$aryl, $C_{5-10}$heteroaryl, $C_{1-4}$alkyl$C_{6-10}$aryl and $C_{1-4}$alkyl$C_{5-10}$heteroaryl;

alternatively $R_5$ and $R_6$ are bound to the same atom and form an optionally substituted ring that is 4 to 10 carbon atoms in size wherein optionally one or more carbon atoms are replaced with O, S, S(O), $SO_2$, or $NR_7$; and $R_7$ is selected from the group consisting of hydrogen and $C_{1-4}$alkyl and further wherein, unless otherwise stated, each alkyl, cycloalkyl, heterocycyl, heteroaryl, and aryl is optionally substituted.

5. A compound according to claim 1 wherein $R_3$ is $C_6$aryl.

6. A compound according to claim 5 wherein $R_3$ is meta or para substituted.

7. A compound according to claim 6 wherein $R_3$ is para substituted.

8. A compound according to claim 6 wherein the substituent is selected from the group consisting of Cl, F, Br, CN, CH(OH)CRR'(OH), where R and R'=H or $C_{1-4}$alkyl.

9. A compound according to claim 1 or a pharmaceutically acceptable derivative, polymorph, salt or prodrug thereof wherein $R_1$ is $C_{1-4}$alkyl.

10. A compound according to claim 9 or a pharmaceutically acceptable derivative, polymorph, salt or prodrug thereof wherein $R_1$ is methyl.

11. A compound according to claim 1 wherein $R_4$ is selected from the group consisting of H, alkyl, $CH_2CONR_2$ (R=H, alkyl), $CH_2CO_2R$ (R=H, alkyl), $CH_2NHCOR$, $(CH_2)_n$hetaryl (wherein n=1-4).

12. A compound according to claim 1 wherein $R_2$ is selected from the group consisting of CN, $C_{5-10}$heteroaryl, $CO_2R_6$, $CONR_5R_6$, $CONHSO_2R_5$, $CONR_5OR_6$, $C_{1-4}$alkyl$NR_5R_6$.

13. A compound according to claim 12 wherein $R_2$ is selected from the group consisting of CN, $CONR_5R_6$, $CONHSO_2R_5$, $CONR_5OR_6$ and $C_{5-10}$heteroaryl.

14. A compound according to claim 12 wherein $R_2$ is $CONR_5R_6$, $R_5$ is H and $R_6$ is $C_{1-4}$alkyl$C_{6-10}$aryl.

15. A compound according to claim 14 wherein $R_6$ is 1,1-ethylbenzene.

16. A compound according to claim 12 wherein $R_2$ is $C_{5-10}$heteroaryl.

17. A compound according to claim 16 wherein $R_2$ is tetrazole or 3-oxo-1,2,4-isoxazole.

18. A composition comprising a compound according to claim 1 and a pharmaceutically acceptable excipient.

19. A method for treating a bromodomain-containing protein-mediated disorder in a patient in need thereof, comprising the step of administering to said patient a composition according to claim 18.

20. A compound according to claim 1 for use in the treatment of a bromodomain-containing protein-mediated disorder in a patient in need thereof.

* * * * *

UNITED STATES PATENT AND TRADEMARK OFFICE
CERTIFICATE OF CORRECTION

PATENT NO.          : 10,167,292 B2
APPLICATION NO.     : 15/749950
DATED               : January 1, 2019
INVENTOR(S)         : Chris Burns et al.

It is certified that error appears in the above-identified patent and that said Letters Patent is hereby corrected as shown below:

In the Claims

At Column 134, Claim number 1, Line numbers 19-21:
"group consisting of $C_{1-4}$alkyl, CN, Cl, Br, I, $C_{3-10}$heterocyclyl, $OC_{1-4}$alkyl, $C_{5-10}$heteroaryl, $C_{1-4}$alkyl $C_{6-10}$aryl, $C_{1-4}$alkyl$C_{5-10}$heteroaryl, hydroxyl, nitro,"
Should read:
-- group consisting of $C_{1-4}$alkyl, CN, Cl, Br, I, 3- to 10-membered heterocyclyl, $OC_{1-4}$alkyl, 5- 10-membered heteroaryl, $C_{1-4}$alkyl $C_{6-10}$aryl, $C_{1-4}$alkyl(5- 10-membered heteroaryl), hydroxyl, nitro, --

At Column 134, Claim number 1, Line number 27:
"$C_{3-10}$cycloalkyl, $C_{3-10}$heterocyclyl, $C_{6-10}$aryl,"
Should read:
-- $C_{3-10}$cycloalkyl, 3- to 10-membered heterocyclyl, $C_{6-10}$aryl, --

At Column 134, Claim number 1, Line number 29:
"$R_4$ is 1 to 2 groups on the same or adjacent carbons"
Should read:
-- $R_4$ is 0 to 2 groups on the same or adjacent carbons --

At Column 134, Claim number 1, Line number 33:
"$C_{1-4}$alkyl$C_{5-10}$heteroaryl;"
Should read:
-- $C_{1-4}$alkyl(5- 10-membered heteroaryl); --

At Column 134, Claim number 1, Line numbers 36-37:
"$C_{3-10}$heterocyclyl, $C_{6-10}$aryl, $C_{5-10}$heteroaryl, $C_{1-4}$alkyl$C_{6-10}$aryl and $C_{1-4}$alkyl$C_{5-10}$heteroaryl;"

Signed and Sealed this
Fifth Day of January, 2021

Andrei Iancu
*Director of the United States Patent and Trademark Office*

CERTIFICATE OF CORRECTION (continued)
U.S. Pat. No. 10,167,292 B2

Should read:
-- 3- to 10-membered heterocyclyl, $C_{6-10}$aryl, 5- to 10-membered heteroaryl, $C_{1-4}$alkyl$C_{6-10}$aryl and $C_{1-4}$alkyl(5- to 10-membered heteroaryl); --

At Column 135, Claim number 4, Line numbers 19-21:
"group consisting of $C_{1-4}$alkyl, CN, Cl, Br, I, $C_{3-10}$heterocyclyl, $OC_{1-4}$alkyl, $C_{5-10}$heteroaryl, $C_{1-4}$alkyl$C_{6-10}$aryl, $C_{1-4}$alkyl$C_{5-10}$heteroaryl, hydroxyl, nitro,"
Should read:
-- group consisting of $C_{1-4}$ alkyl, CN, Cl, Br, I, 3- to 10-membered heterocyclyl, $OC_{1-4}$alkyl, 5- 10-membered heteroaryl, $C_{1-4}$alkyl$C_{6-10}$aryl, $C_{1-4}$alkyl(5- to 10-membered heteroaryl), hydroxyl, nitro, --

At Column 135, Claim number 4, Line number 30:
"$C_{1-4}$alkyl$C_{5-10}$heteroaryl;"
Should read:
-- $C_{1-4}$alkyl(5- to 10-membered heteroaryl); --

At Column 135, Claim number 4, Line numbers 33-34:
"$C_{3-10}$heterocyclyl, $C_{6-10}$aryl, $C_{5-10}$heteroaryl, $C_{1-4}$alkyl$C_{6-10}$aryl and $C_{1-4}$alkyl$C_{5-10}$heteroaryl;"
Should read:
-- 3- to 10-membered heterocyclyl, $C_{6-10}$aryl, 5- to 10-membered heteroaryl, $C_{1-4}$alkyl$C_{6-10}$aryl and $C_{1-4}$alkyl(5- to 10-membered heteroaryl); --

At Column 136, Claim number 8, Line number 7:
"stituent is selected from the group consisting of Cl, F, Br,"
Should read:
-- stituent of $R_3$ is selected from the group consisting of Cl, F, Br, --

At Column 136, Claim number 11, Line numbers 17-19:
"selected from the group consisting of H, alkyl, $CH_2CONR_2$ (R=H, alkyl), $CH_2CO_2R$ (R=H, alkyl), $CH_2NHCOR$, $(CH_2)_n$hetaryl (wherein n = 1-4)."
Should read:
-- selected from the group consisting of -H, alkyl, $CH_2CON(R)_2$ (R=H, alkyl), $CH_2CO_2R$ (R=H, alkyl), $CH_2NHCOR$, $(CH_2)_n$(5- to 10-membered heteroaryl) (wherein n = 1-4). --

At Column 136, Claim number 12, Line number 21:
"selected from the group consisting of CN, $C_{5-10}$heteroaryl,"
Should read:
-- selected from the group consisting of CN, 5- to 10-membered heteroaryl, --

At Column 136, Claim number 13, Line number 26:
"$CONHSO_2R_5$, $CONR_5OR_6$ and $C_{5-10}$heteroaryl."

Should read:
-- CONHSO$_2$R$_5$, CONR$_5$OR$_6$ and 5- to 10-membered heteroaryl. --

At Column 136, Claim number 16, Line number 32:
"C$_{5-10}$heteroaryl."
Should read:
-- 5- to 10-membered heteroaryl. --